United States Patent [19]
Bullough et al.

[11] Patent Number: 5,777,100
[45] Date of Patent: Jul. 7, 1998

[54] AICA RIBOSIDE ANALOGS

[75] Inventors: David A. Bullough; Harry E. Gruber, both of San Diego; Ernest K. Metzker; Kevin M. Mullane, both of Del Mar; Bheemarao G. Ugarkar, Escondido; Clinton E. Browne, Vista, all of Calif.

[73] Assignee: Gensia Inc., San Diego, Calif.

[21] Appl. No.: 485,665

[22] Filed: Jun. 7, 1995

Related U.S. Application Data

[63] Continuation of Ser. No. 732,182, Jul. 17, 1991, abandoned, which is a continuation-in-part of Ser. No. 566,196, Aug. 10, 1990, abandoned.

[51] Int. Cl.$^6$ .................... C07H 19/052; A61K 31/70
[52] U.S. Cl. .................. 536/26.9; 536/28.6; 536/28.7; 536/28.8; 514/43; 514/44
[58] Field of Search ................... 536/28.6, 28.7, 536/26.9, 28.8; 514/43, 44

[56] References Cited

U.S. PATENT DOCUMENTS

| | | | |
|---|---|---|---|
| 4,912,092 | 3/1990 | Gruber | 514/46 |
| 5,082,829 | 1/1992 | Gruber et al. | 514/43 |

OTHER PUBLICATIONS

G. Robert Greenberg, *Preparation of 5'-Phosphoribosyl-5-Amino-4-Imidazolecarboxamide, J. Biol. Chem.*, 219:423–433, 1956.

Michael P. Groziak, et al., *Nonenzymatic Synthesis of 5-Aminoimidazole Ribonucleoside And Recognition Of Its Facile Rearrangements, Proc. Natl. Acad. Sci. USA* vol. 85, pp. 7174–7176, Oct. 1988.

George A. Ivanovics, et al., *The Synthesis of 2–Substituted Derivatives of 5–Amino–1–β–D–Ribofuranosylimidazole–4–carboxamide. Ring Opening Reactions of 2–Azapurine Nucleosies, J. Org. Chem.*, vol. 39, No. 25, 1974.

Kiyomi Kikugawa et al., *Platelet Aggregation Inhibitors, Chem. Pharm. Bull*, 25(8) pp. 1959–1969, 1977.

Ryuji Marumoto, et al., *Synthesis And Coronary Vasodilating Activity Of 2–Substituted Adenosines, Chem. Pharm. Bull.*, 23(4), pp. 759–774, 1975.

Teiichi Murakami, et al., *Synthesis Of 2–Formyladenoise Using Diethoxyacetonitrile As A Synthon, Heterocycles*, vol. 16, No. 8, 1981.

Kiyoshi Omura, et al., *Synthesis of 2–Phenylaminoadenosine From Imidazole Nucleosides, Chem. Pharm. Bull.*, 29(7) 1870–1875, 1981.

Elliot Shaw, *5–Amino–4–Imidazolecarboxamide Riboside From Inosine. Ring–opeing Reactions Of Purine Nucleosides, Organic And Biological Chemistry*, vol. 80, pp. 3899–3902, Aug. 5, 1958.

Prem C. Srivastava, et al., *Synthesis of 5–Amino–1–(5–deoxy–β–D–Ribofuranosyl) Imidazole–4–Carboxamide And Related 5'–Deoxyimidazole Ribonucleosides, Journal of Medicinal Chemistry*, vol. 18, No. 12, pp. 1237–1240, 1975.

Jennifer A. Suggs, et al., *Synthesis And Biodistribution Of p–Iodophenyl Analogues Of A Naturally Occuring Imidazole Ribonucleoside, J. Heterocyclic Chem.*, 25, 1331, Sep.–Oct. 1988.

*Primary Examiner*—James O. Wilson
*Attorney, Agent, or Firm*—Darby & Darby

[57] ABSTRACT

Analogs of 5-amino-1-beta-D-ribofuranosylimidazole-4-carboxamide (AICA riboside) are provided which are useful in increasing extracellular levels of adenosine.

16 Claims, 5 Drawing Sheets

AICA RIBOSIDE ANALOGS

CROSS REFERENCE TO RELATED APPLICATIONS

This application is a continuation of U.S. Ser. No. 07/732,182, filed Jul. 17, 1991, now abandoned, which is a continuation-in-part of U.S. Ser. No. 07/566,196, filed Aug. 10, 1990, now abandoned; the disclosures of which are incorporated herein by reference.

FIELD OF INVENTION

The present invention generally relates to nucleoside analogs, specifically to 5-amino-1-beta-D-ribofuranosyl-imidazole-4-carboxamide ("AICA riboside") analogs. The present invention also relates to the preparation and use of these compounds in the treatment of cardiovascular, cerebrovascular, other ischemic disorders, and other diseases which can be regulated by local increase of extracellular adenosine such as inflammatory or thrombotic conditions.

BACKGROUND OF THE INVENTION

The present invention is directed to novel compounds which are analogs of AICA riboside. AICA riboside enters cells and is phosphorylated to AICA riboside monophosphate ("ZMP"), a naturally occurring intermediate in purine biosynthesis. AICA riboside increases extracellular adenosine levels under conditions of net ATP breakdown and, therefore, in light of the cardioprotective and neuroprotective properties of adenosine it may have potential therapeutic uses. However, AICA riboside has a relatively low potency and short half life. Also, we have found that AICA riboside does not cross the blood-brain barrier well and is inefficiently absorbed from the gastrointestinal tract. These characteristics of limited potency, limited oral bioavailability and limited brain penetration decrease its potential for use as a therapeutic agent.

AICA riboside treatment has been reported to have beneficial effects in a number of experimental models of myocardial ischemia. In a dog model, in which pacing induced a profound progressive decline in wall thickening and endocardial blood flow and an increase in ST segment deviation of the intramyocardial EKG, AICA riboside markedly attenuated these changes to maintain contractile function [Young and Mullane, Am. J. Physio., in press (1991)]. In another dog model, in which ischemia was induced by coronary artery occlusion, AICA riboside was reported to be beneficial by significantly decreasing ischemia-induced arrhythmias and improving blood flow to the ischemic region of the myocardium (Gruber et al, Circulation 80 (5): 1400–1410 (1990)). An effect of AICA riboside to increase regional blood flow and maintain contractile function was also reported in a dog model of coronary embolization in which ischemia was induced by administration of microspheres directly into the coronary circulation (Takashima et al, Heart and Vessels 5 (Supplement 4): 41 (1990)). A potential consequence of this reported redistribution in blood flow by AICA riboside was said to be a reduction of infarct size (McAllister et al, Clinical Research 35: 303A (1987)). Treatment with AICA riboside has been reported to have favorable consequences in other experimental models of myocardial ischemia. For instance, Mitsos et al (Pharmacology 31: 121–131 (1985)) reported that AICA riboside improved the recovery of post-ischemic function in the isolated blood-perfused cat heart and Bullough et al. (Jap. J. Pharmacol 52: 85p (1990)) reported improved recovery in an isolated buffer-perfused guinea pig heart. Thus, AICA riboside has been reported to alleviate ischemia-induced injury to the heart in various experimental models.

AICA riboside has also been reported to protect brain tissue from damage in two different experimental models of cerebral ischemia. In a gerbil model of global ischemia, AICA riboside was reported to prevent the degeneration of hippocampal CA-1 cells, which in control animals were virtually completely destroyed (Phillis and Clough-Helfman, Heart and Vessels 5 (Supplement 4): 36 (1990)). In a rat model of focal ischemia, AICA riboside treatment was reported to provide a significant reduction in infarct size. The protective effects of AICA riboside have also been reported in other models of ischemia, including rat skin flap survival (Qadir et al, Fed Proc. A626 (1988); Salerno et al in Proceedings of 35th Annual Meeting of the Plastic Surgery Research Council, pp.117–120 (1990)) and gastrointestinal ischemia-reperfusion injury (Kaminski & Proctor, Circulation Res. 66 (6): 1713–1729 (1990)).

A number of studies suggest that the beneficial effects of AICA riboside can be ascribed, at least in part, to an increase in local levels of adenosine, which has similar cardioprotective (Olafsson et al, Circulation 76: 1135–1145 (1987) ) and neuroprotective properties (Dragunow & Faull, Trends in Pharmacol. Sci. 7: 194 (1988); Marangos, Medical Hypothesis 32: 45 (1990)). Evidence for AICA riboside-induced enhancement of adenosine levels is both direct i.e. a consequence of measurement of adenosine itself in both animal and cell culture models (Gruber et al, Circulation 80(5): 1400–1410 (1990); Barankiewicz et al, Arch. Biochem. Biophys., 283: 377–385, (1990)) and indirect i.e. implicated by reversal of the anti-ischemic properties of AICA riboside by removal of exogenous adenosine using adenosine deaminase (Young & Mullane, Am.J. Physio., in press (1991)). In hearts subjected to ischemia and reperfusion, cellular damage has been, in part, attributed to plugging of the microvessels by neutrophils. Adenosine has been reported to inhibit neutrophil adhesion to coronary endothelial cells and hence neutrophil accumulation (Cronstein et al., J. Clin. Invest. 78: 760–770 (1986)). Consequently, another feature of the adenosine-mediated protective effects of AICA riboside in the heart can be through prevention of neutrophil-dependent tissue injury in some models of ischemia and reperfusion. This is supported by evidence for decreased accumulation of neutrophils in the ischemic region of the heart by AICA riboside (Gruber et al, Circulation 80: 1400–1410 (1990)).

A recognition of the cardioprotective and neuroprotective properties of adenosine have led to attempts to explore the therapeutic use of exogenously administered adenosine itself. However the short half life of adenosine in blood (<10 secs) necessitates the use of high doses and continuous infusions to maintain levels appropriate for most treatments. Adenosine itself causes hypotension, i.e. reduces blood pressure; it is also a negative chronotropic and dromotropic agent, i.e. reduces heart rate and electrical conduction in the heart, respectively. Adenosine would therefore exert marked systemic hemodynamic effects at concentrations that would be required to elicit cardioprotective or neuroprotective properties. These systemic cardiovascular actions are frequently contraindicated in most clinical conditions where adenosine could be useful. In contrast, as a result of its local effects on adenosine levels, AICA riboside administration does not produce such side-effects, even at doses considerably higher than the expected therapeutic levels (Gruber et al; Circulation 80: 1400–1410, (1990); Young & Mullane, Am.J. Physio., in press, (1991)).

Adenosine receptor agonists have also been studied and effects similar to adenosine have been reported in a number of experimental models. (Daly, *J. Med. Chem.* 25(3): 197 (1982). Again, because most cell types have adenosine receptors, exogenously administered adenosine agonists exhibit profound actions on a variety of tissues and organs, outside of the target organ, thereby limiting their therapeutic potential.

Other ways of potentially achieving the effect of a high local extracellular level of adenosine have been studied. They include: a) interference with the uptake of adenosine with reagents that specifically block adenosine transport, as described by Paterson et al., in the *Annals of the New York Academy of Sciences*, Vol. 255, p. 402 (1975); b) prevention of the degradation of adenosine, as described by Carson and Seegmiller in *The Journal of Clinical Investigation*, Vol. 57, p. 274 (1976); and c) the use of analogs of adenosine constructed to bind to adenosine cell plasma membrane receptors.

There are a repertoire of chemicals that reportedly can inhibit the cellular uptake of adenosine. Some have been reported to do so specifically, and are believed to be essentially competitive inhibitors of adenosine uptake, and others are believed to inhibit nonspecifically. p-nitrobenzylthioinosine appears to be a competitive inhibitor, while dipyridamole and a variety of other chemicals, including colchicine, phenethylalcohol and papaverine appear to inhibit uptake nonspecifically.

U.S. Pat. No. 4,115,641 to Fischer et al. is directed to certain ribofuranosyl derivatives which are said to have cardiac and circulatory-dynamic properties. In particular, Fischer et al. are directed to certain compounds which are said to have intrinsic adenosine-like modes of action as determined by measuring decreased heart rate and blood pressure.

In contrast, AICA riboside and AICA riboside-like compounds lead to enhanced adenosine levels at the specific time and location of a pathological event and thus permit increased adenosine levels to be selectively targeted without the detrimental side effects.

The present invention is directed to AICA riboside analogs which exhibit and, in many cases, improve upon, the positive biological effects of AICA riboside. The novel compounds typically exhibit one or more of the following improvements over AICA riboside: 1) functional benefits at lower doses; 2) more potent adenosine regulating actions; 3) increased half-lives or; 4) increased oral bioavailability and/or brain penetration.

SUMMARY OF THE INVENTION

The present invention is directed to certain new analogs of AICA riboside which exhibit enhanced potency, efficacy or improved pharmacokinetics or metabolism compared to AICA riboside. In particular, the present invention is directed to four series of novel analogs having chemical modification at the following positions: N-4 (Series I), C-2 (Series II), 5'-C (Series III) and 2'-C (Series IV). A number of compounds in these preferred series provide improved functional recovery of post ischemic function at lower concentrations than AICA riboside. The beneficial effects of these compounds result, at least in part, from their ability to increase extracellular adenosine levels more effectively than AICA riboside. Moreover, some of these compounds are inhibitors of adenosine transport and individual adenosine-regulating enzymes.

The AICA riboside analogs of this invention are useful in treating a variety of clinical situations where increased extracellular levels of adenosine would be beneficial. Accordingly, the present invention is directed to the prophylactic and affirmative treatment of such conditions as heart attack, angina, PTCA, cardioplegia, stroke and other ischemia-related diseases, as well as seizures and inflammatory disorders. This invention is also directed to pharmacological compositions comprising an effective amount of the analog of the present invention and a pharmaceutically acceptable carrier.

Definitions

As used herein, the following terms have the following meanings, unless expressly stated to the contrary.

The term "hydrocarbyl" refers to an organic radical comprised of primarily carbon and hydrogen and includes alkyl, alkenyl and alkynyl groups, as well as aromatic groups including aryl and aralkyl groups and groups which have a mixture of saturated and unsaturated bonds, alicyclic (carbocyclic or cycloalkyl) groups or such groups substituted with aryl (aromatic) groups or combinations thereof and may refer to straight-chain, branched-chain or cyclic structures or to radicals having a combination thereof.

The term "alkyl" refers to saturated aliphatic groups, including straight, branched and carbocyclic groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "aryl" refers to aromatic groups having from about 6 to 14 carbon atoms and includes cyclic aromatic systems such as phenyl and naphthyl.

The term "aralkyl" refers to an alkyl group of about 1 to 4 carbon atoms substituted with an aryl group of from 6 to 10 carbon atoms and includes, for example, benzyl, p-chlorobenzyl, p-methylbenzyl and 2-phenylethyl.

The term "alkenyl" refers to unsaturated alkyl groups having at least one double bond [e.g. $CH_3CH=CH(CH_2)_2-$] and includes both straight and branched-chain alkenyl groups.

The term "alkynyl" refers to unsaturated groups having at least one triple bond [e.g. $CH_3C\equiv C(CH_2)_2-$] and includes both straight chain and branched-chain groups.

The term "halo" or "halogen" refers to fluorine, chlorine, bromine and iodine.

The term "acyl" refers to the group

wherein $R^1$ is hydrocarbyl.

The term "alkylene" refers to straight, branched-chain and carbocyclic alkylene groups which are biradicals, and includes, for example, groups such as ethylene, propylene, 2-methylpropylene (e.g.

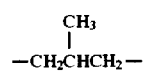

1,6-n-hexylene, 3-methylpentylene (e.g.

1,4-cyclohexylene, and the like.

The term "amide" or "amido" refers to the group

wherein each R" is independently hydrogen or hydrocarbyl, or to compounds having at least one such group.

The term "carboxamide" refers to the group

wherein each R" is independently hydrogen or hydrocarbyl. The term "unsubstituted carboxamide" refers to the group

The term "acylamino" refers to the group

wherein R' is hydrocarbyl. The term "lower acylamino" refers to acylamino groups wherein R' is alkyl of 1 to 6 carbon atoms.

The term "carbonate ester" refers to the group

wherein R' is hydrocarbyl or to compounds having at least one such group.

The term "acyl ester" refers to the group

wherein R' is hydrocarbyl or to compounds having at least one such group.

The term "phosphate ester" refers to the group

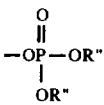

wherein R" is independently hydrogen or hydrocarbyl and/ or to compounds having at least one such group, and includes salts thereof.

The term "mixed ester" refers to compounds having at least one carbonate ester group and at least one acyl ester group or to compounds having combinations of different acyl ester or carbonate ester groups.

The term "carboxylic acid ester" or "carboxy ester" refers to the group

wherein R' is hydrocarbyl or to compounds having at least one such group.

The term "carbocyclic AICA riboside" refers to an analog of AICA riboside wherein the oxygen atom in the ribosyl ring has been replaced by a methylene (—CH$_2$—).

The term "hydrocarbyloxy" refers to the group R'O— wherein R' is hydrocarbyl.

The term "alkoxy" refers to the group R'O— wherein R' is alkyl.

The term "hydrocarbylthio" refers to the group having the formula R'S— wherein R' is hydrocarbyl.

The term "hydrocarbylamino" refers to the groups —NHR' or —NR'$_2$ where R' is an independently selected hydrocarbyl group.

The term "hydrocarbylimidate" refers to the group

wherein R" is hydrocarbyl.

The term "carboxamideoxime" refers to the group

The term "hydrocarbyloxyamidine refers to the group

wherein R' is hydrocarbyl.

The term "hydrocarbyloxycarbonyl refers to the group

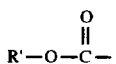

wherein R' is hydrocarbyl.

The term "hydrocarbyloxycarboxy" refers to the group

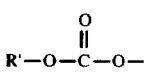

wherein R' is hydrocarbyl.

The term "thioester" refers to the group

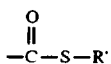

wherein R' is hydrocarbyl.

DETAILED DESCRIPTION OF THE INVENTION

Preferred AICA Riboside Analogs

Figure 1:
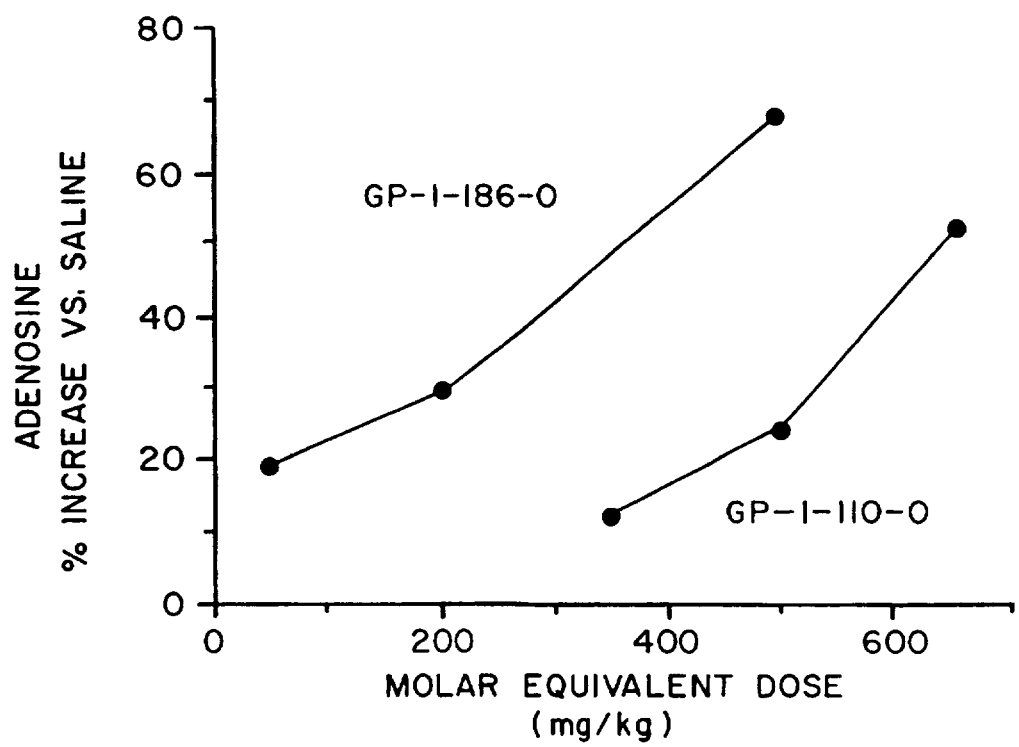
FIG. 1 depicts a comparison of the dose-dependent effects of AICA riboside (Compound No. 1 of Tables XII and XIII (1-110)) and an N-4 (Series I) substituted AICA riboside analog (Compound No. 10 (1-186)) on tissue adenosine levels in a rat heart ischemia model.

According to the present invention, preferred analogs of AICA riboside include compounds of the formula I

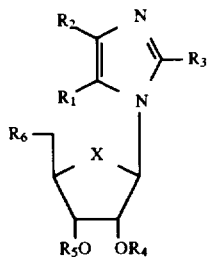

(I)

or a pharmaceutically acceptable salt thereof wherein X is —O— or —CH$_2$—; R$_1$ is hydrogen, amino, hydrocarbylamino, acylamino, or dihydrocarbylaminoalkyleneimino; R$_2$ is hydrogen, cyano, hydrocarbylimidate, carboxamideoxime, hydrocarbyloxyamidine, carboxamide, or carboxylic acid or an amide, ester, thioester or salt thereof; R$_3$ is hydrogen, hydrocarbyl, amino, hydrocarbylamino, halogen, hydroxy (including tautomeric 2-imidazolone), hydrocarbyloxy, sulfhydryl (including tautomeric 2-imidazolthione), or hydrocarbylthio; R$_4$ and R$_5$ are independently hydrogen, alkyl, acyl or hydrocarbyloxycarbonyl; R$_6$ is hydrogen, hydrocarbyl, halogen, hydroxy, hydrocarbyloxy, sulfhydryl, hydrocarbylthio, sulfamyloxy, amino, hydrocarbylamino, azido, acyloxy or hydrocarbyloxycarboxy or phosphate ester group or salts thereof; provided that when R$_1$ is amino, R$_2$ is unsubstituted carboxamide, R$_3$ is hydrogen; R$_4$ and R$_5$ are hydrogen, acyl or hydrocarboxycarbonyl; then R$_6$ is not hydroxy, acyloxy or hydrocarbyloxycarboxy.

Alternatively R$_2$ may be a group of the formula:

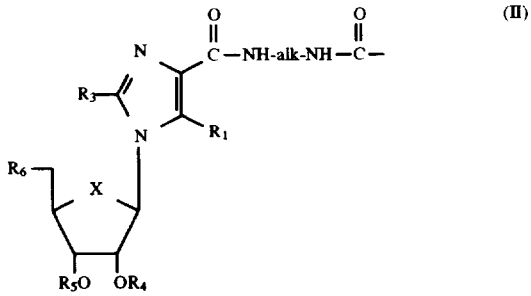

(II)

wherein R$_1$, R$_3$, R$_4$, and R$_5$ and R$_6$ are as previously defined in conjunction with formula (I) and alk is an alkylene group of from 2 to 8 carbon atoms. Suitable alk groups include n-hexylene and 1,4-cyclohexylene. Since compounds of the above formula wherein R$_3$ is hydroxy or sulfhydryl may exist in their isomeric (tautomeric) imidazole-2-one and imidazole-2-thione forms, these isomers are intended to be included in the ambit of Formula I.

Preferred compounds include those wherein (i) R$_1$ is amino, R$_2$ is carboxamide wherein one of the amide hydrogens is replaced by a hydrocarbyl group, more preferably an aralkyl group (such hydrocarbyl or aralkyl group is optionally substituted, suitable substituents include those set forth below); R$_3$ is hydrogen, R$_4$ and R$_5$ are hydrogen or hydrocarbyloxycarbonyl, more preferably and R$_6$ is hydroxy or amino (Series I); (ii) R$_1$ is amino, R$_2$ is carboxamide, R$_3$ is halogen or sulfhydryl, R$_4$ is hydrogen, R$_5$ is hydrogen and R$_6$ is hydroxy (Series II); (iii) R$_1$ is amino, R$_2$ is carboxamide; R$_3$, R$_4$ and R$_5$ are hydrogen and R$_6$ is amino (Series III) and (iv) R$_1$ is amino, R$_2$ is carboxamide, R$_3$ is hydrogen, R$_4$ is alkyl, R$_5$ is hydrogen and R$_6$ is hydroxy (Series IV).

In particular, in view of their demonstration of activity in various experimental models, preferred compounds include Compound Nos. 10, 23, 25, 29, 47, 52, 53 (Series I), 27, 43 (Series II), 21, 66 (Series III) and 20, 34 (GP-1-250) and 32 (GP-1-262) (Series IV) of Tables XII and XIII.

Preferred Novel AICA Riboside Analogs

One preferred group of compounds of formula I include certain novel AICA riboside analogs wherein X is —O— or —CH$_2$—; R$_1$ is amino, hydrocarbylamino or dihydrocarbylaminoalkyleneimino, R$_2$ is carboxamide wherein one of the amide hydrogens (attached to the nitrogen atom) is optionally replaced by alkyl, cycloalkyl, or aryl or aralkyl, optionally substituted with 1 to 3 substituents independently selected from halogen, alkyl, aryl, nitro, amino, hydrocarbylamino, sulfhydryl, hydrocarbylthio, hydroxy, hydrocarbyloxy, trifluoromethyl, or sulfonamide; R$_2$ is carboxamide wherein both amide hydrogens are replaced by alkyl or together by an alkylene or aralkylene group to form a ring; or R$_2$ is —C(O)—S—R$_7$ wherein R$_7$ is alkyl, cycloalkyl, aryl or aralkyl optionally substituted with 1 to 3 substituents independently selected from halogen, alkyl, aryl, nitro, amino, hydrocarbylamino, sulfhydryl, hydrocarbylthio, hydroxy, hydrocarbyloxy, trifluoromethyl or sulfonamide; or further, R$_2$ is a group of formula II wherein R$_1$, R$_3$, R$_4$, R$_5$ and R$_6$ are as defined with formula I and alk is alkylene of 2 to 8 carbon atoms; R$_3$ is hydrogen, amino, hydrocarbylamino, halogen, hydroxy (including tautomeric imidazolone), hydrocarbyl, sulfhydryl (including tautomeric 2-imidazolthione) or hydrocarbylthio; R$_4$ and R$_5$ are independently hydrogen, hydrocarbyl (of 1 to about 18 carbon atoms), acyl or hydrocarbyloxycarbonyl; and R$_6$ is hydroxy, hydrogen, hydrocarbyl, halogen, hydrocarbyloxy, sulfhydryl, hydrocarbylthio, sulfamyloxy, amino, hydrocarbylamino, azido, acyloxy, hydrocarbyloxycarboxy or phosphate ester or salt thereof; provided that when —X— is —O— or —CH$_2$—, R$_1$ is amino, R$_2$ is unsubstituted carboxamide, R$_3$ is hydrogen, R$_4$ and R$_5$ independently are hydrogen, acyl or hydrocarbyloxycarbonyl, then R$_6$ is not hydrogen, hydroxy, acyloxy or hydrocarbyloxycarboxy or when R$_4$ and R$_5$ are both hydrogen, then R$_6$ is not a phosphate ester; when X is oxygen, R$_1$ is amino, R$_2$ is unsubstituted carboxamide, R$_3$ is sulfhydryl, and R$_4$ and R$_5$ are both hydrogen, then R$_6$ is not acetoxy; when X is oxygen, R$_1$ is amino, R$_2$ is unsubstituted carboxamide and R$_3$ is chloro, bromo, amino or methoxy, and R$_4$ and R$_5$ both hydrogen, then R$_6$ is not hydroxy or when R$_4$ and R$_5$ are both acetyl, then R$_6$ is not acetoxy; and provided further that when X is oxygen, R$_1$ is amino, R$_2$ is benzylcarboxamide or p-iodophenylcarboxamide, R$_3$ is hydrogen, then R$_4$ and R$_5$ are not both hydrogen and R$_6$ is not hydroxy; or when R$_2$ is p-iodophenylcarboxamide, then R$_4$ and R$_5$ are not both acetyl and R$_6$ is not acetoxy.

Preferred compounds include those wherein R$_1$ is amino R$_2$ is carboxamide substituted with an aralkyl group, more preferably a benzyl group, having from 1 to 3 ring substitutions as described above, or cycloalkyl. In view of their activity in various experimental models, preferred compounds include Compound Nos. 23, 25, 29, 47, 52 and 53

One example of an especially preferred compound is a compound where X is oxygen, R$_1$ is amino, R$_2$ is p-chlorobenzylcarboxamide, R$_3$, R$_4$ and R$_5$ are hydrogen and R$_6$ is amino and salts thereof. One particularly preferred salt is the hydrochloride salt. Other particularly preferred salts are sodium and potassium salts, especially disodium and mono potassium.

Preparation of Preferred Novel AICA Riboside Analogs

The novel substituted imidazole analogs of the present invention can be synthesized by well known chemical reactions as demonstrated in the examples which follow. In general, compounds of formula (I) can be prepared from 4-methyl-5-nitro-1H-imidazole by the route described by Baker et al (Baker D., *J. Org. Chem.* 47: 3457 (1982)) to prepare 1-benzyl-5-nitro-1H-imidazole-4-carboxylic acid, followed by the additional step of reducing the nitro group to give the desired amino group at $R_1$. Alternatively, the elegant synthesis of AICA riboside reported by Ferris et al. (Ferris, J. P., *J. Org. Chem.* 50: 747 (1985), allows a versatile route to 4-substituted 5-aminoimidazoles starting with the appropriately protected riboside and diaminomaleonitrile. This route also allows for the introduction of the desired $R_3$ alkyl, hydrocarbyl and aryl groups by selection of the appropriate ortho ester in the cyclization reaction of the maleonitrile to the imidazole. Other desired $R_3$ substituents can be introduced by the methods described by Miyoshi et al. (Miyoshi T., *Chem. Pharm. Bull.* 24(9): 2089 (1976) for the preparation of 2-bromo and 5-amino-2-thio-1-(2,3-O-isopropylidene-β-D-ribofuranosyl)-4-imidazolecarboxamide or the method of Ivanovics et al. (Ivanovics. G. A. et al., *J. Org. Chem.* 25: 3631 (1974)) for the preparation of 2-alkoxy, 3-amino, and 2-hydroxy (as the tautomeric 2-imidazolones) substituted 5-amino imidazole-4-carboxamides. Compounds where the desired $R_1$ substituent is acylamino can be prepared by acylation of the corresponding appropriately protected $R_1$ amino compound with the desired acyl anhydride followed by de-O-acylation with ammonia or sodium methoxide. Compounds where $R_1$ is alkylamino or arylamino can be prepared by reductive alkylation of the corresponding appropriately protected $R_1$ amino compound with the desired hydrocarbyl amine as described by Sato et al. (*Chem. Pharm. Bull.* 37: 1604 (1989)).

Preparation of compounds where $R_6$ is acyloxy or hydrocarbyloxycarboxy can be prepared selectively by reaction of the appropriate hydrocarbyl acid anhydride or hydrocarbyl chloro carbonate with the 2',3'-O-isopropylidene protected riboside followed by removal of the isopropylidene group with dilute aqueous acid as described by Miyoshi et al. (vide supra). Compounds where $R_6$ is hydrocarbyloxy can be prepared from the protected 5-substituted pentoses (Snyder J. R., *Carbonhydr. Res.* 163: 169 (1987)), using the method of Ferris et al. (vide supra). Compounds according to formula (I) where $R_6$ is sulfhydryl, hydrocarbylthio or hydrocarbylamino can be prepared from the 5'-deoxy-5'-iodo-2,3'-isopropylidene imidazole riboside (Srivastava P. C., *J. Med. Chem.* 18: 1237 (1975)) by nucleophilic displacement of the halogen with the desired amine or mercaptan. Compounds according to formula (I) where $R_6$ is alkylamido or arylamido can be prepared from the corresponding 5-amino-5'-deoxyimidazole riboside by acylation with the desired alkyl or aryl acid anhydride followed by de-O-acylation with ammonia or sodium methoxide. Compounds according to formula (I) where $R_6$ is hydrocarbyl can be prepared from the 1-(2,3-O-isopropylidene-β-D-ribo-pento-1,5-dialdo-1,4-furanosyl)imidazoles by the Wittig reaction modification of nucleosides described by Montgomery et al. (*J. Het. Chem.* 11: 211 (1974)). Compounds according to formula (I) where $R_6$ is phosphate or a phosphate ester can be prepared by the general method of Khwaja et al. (*Tetrahedron* 27: 6189 (1971)) for nucleoside phosphates.

Utility

The AICA riboside analog compounds of this invention will be particularly useful in the reduction of injury during or prevention of ischemia-related events i.e. conditions that arise because of restriction of blood supply. This includes heart attack, or myocardial infarction, a situation that follows from obstruction of one or more of the coronary arteries supplying blood to the heart muscle, or myocardium, and which, if prolonged, leads to irreversible tissue damage. Compounds which, like AICA riboside, lead to increased local levels of adenosine, and thereby increasing blood flow to the ischemia myocardium, will ameliorate this tissue damage.

One current treatment for a heart attack is thrombolytic therapy, which involves administering a clot dissolving agent such as streptokinase or tissue plasminogen activator factor (tPA). However, these drugs must be used within a few hours (1–3) of the heart attack and their effectiveness decreases dramatically with longer delay. The compounds of the present invention, which can be administered prophylactically (i.e. before the event) to achieve a benefit, would therefore clearly be useful.

Angina pectoris is a condition in which the blood supply is sufficient to meet the normal needs of the heart but insufficient when the needs of the heart increase (e.g. during exercise), and/or when the blood supply becomes more limited (e.g. during coronary artery spasm). Patients with angina pectoris or with related conditions such as transient ischemic episodes or silent ischemia could similarly benefit from such an adenosinergic intervention.

In advanced coronary artery disease or persistent chest pain at rest, a number of clinical procedures are currently used to improve blood supply to the heart. These include percutaneous transluminal coronary angioplasty (PTCA), also known as angioplasty; percutaneous transluminal directional coronary atherectomy, laser atherectomy, intravascular stents and coronary artery bypass graft surgery. The compounds of this invention will also be useful as adjunctive therapies to these techniques.

Another factor lending to cardiovascular problems is abnormal heart rhythm, or arrhythmias, which lead to deficiencies in the ability of the heart to supply blood. The ability of these compounds, like AICA riboside, to reduce arrhythmias will also make them useful in suppressing this condition.

Stroke and central nervous system (CNS) trauma conditions resulting from reduced blood supply to the CNS and is thus amenable to an intervention that provides increased levels of adenosine to the compromised tissue to facilitate tissue survival. Other indications ameliorated by agents effecting regional blood flow include organ transplantation, skin flap grafting in reconstructive surgery, peripheral vascular disease, endotoxemia, hemorrhagic shock, pulmonary edema, pulmonary injury secondary to burns (thermal injury) or septicemia, pulmonary hypertension, microembolization, impotence, glomerulonephritis or progressive glomerulosclerosis, atherosclerosis, myocarditis, vasculitis and cardiomyopathies and cardiopulmonary arrest.

It is now clear that a significant component of the neurodegeneration resulting from stroke or CNS trauma is caused by increased excitatory amino acid release, which results in neurons being stimulated to death. Adenosine has been reported to inhibit excitatory amino acid release (Burke and Nadler J. *Neurochem.* 51: 1541 (1988)). The compounds of this invention which increase adenosine levels, therefore would also be useful in conditions where excitatory amino acids are implicated such as Huntington's chorea or Alzheimer's disease (Marangos et al. *Trends Neurosci.* 10: 65 (1987)) and Parkinson's disease (Sonsella et al. *Science* 243: 398 (1989)). These studies, together with results from experimental models of memory (Harris et al. *Brain Res.* 323: 132 (1984)) suggest additional utility of these compounds in treatment of disorders related to the effects of the aging process on CNS function.

Adenosine has been reported to be an endogenous modulator of inflammation by virtue of its effects on stimulated granulocyte function (Cronstein et al., *J. Clin. Invest.* 78: 760–770 (1986)) and on macrophage, lymphocyte and platelet function. The compounds of this invention will therefore be useful in conditions in which inflammatory processes are prevalent such as arthritis, osteoarthritis, autoimmune disease, adult respiratory distress syndrome (ARDS), inflammatory bowel disease, necrotizing enterocolitis, chronic obstructive pulmonary disease (COPD) and other inflammatory disorders.

Adenosine has been proposed to serve as a natural anticonvulsant (Lee et al., *Brain Res.* 321: 1650–1654 (1984); Dunwiddie, *Int. Rev. Neurobiol.* 27: 63–139 (1985)). Agents that enhance adenosine levels will therefore be useful for the treatment of seizure disorders. In a recent study, Marangos et al., *Epilepsia* 31: 239–246 (1990) reported that AICA riboside was an inhibitor of seizures in an experimental animal model.

AICA riboside analogs will also be useful in the treatment of patients who might have chronic low adenosine levels or who might benefit from enhanced adenosine, such as those suffering from autism, cerebral palsy, insomnia, anxiety, or other neuropsychiatric symptoms or those suffering from irritable bowel syndrome. Indeed, a number of studies (Komhuber and Fischer *Neurosci. Lett.* 34: 32 (1982); Kim et al. *Eur. Neurol.* 22: 367 (1983)) have linked excitatory amino acids with the pathophysiology of schizophrenia.

The compounds of this invention may also be useful in treating other conditions in which AICA riboside itself has beneficial effects. For instance, since AICA riboside has been reported to have anti-allergic actions in a guinea pig model of bronchospasm induced by antigen sensitization (Bergren et al., submitted to *J. of Allergy and Clinical Immunology* (1990)), AICA riboside analogs may have therapeutic benefit in the treatment of asthma, hayfever or allergic diseases.

The AICA riboside analogs of the present invention are therefore useful in the treatment of a variety of clinical situations where increasing extracellular adenosine levels and in some cases, at the same time, providing free radical scavenging and/or antioxidant activity are beneficial.

Compounds of the invention are administered to the affected tissue at the rate of from 0.01 to 3.0 µmole/min/kg, preferably from 0.1 to 1.0 µmol/min/kg. Under circumstances where longer infusions are desirable, the compounds may be administered at lower rates, e.g. 0.003 to 0.3 µmole/kg/min, preferably 0.01 to 0.1 µmole/kg/min. Such rates are easily maintained when these compounds are intravenously administered as discussed below. When other methods are used (e.g., oral administration), use of time-release preparations to control the rate of release of the active ingredient may be preferred. These compounds are administered in a dose of about 0.01 mg/kg/day to about 200 mg/kg/day, preferably from about 0.5 mg/kg/day to about 100 mg/kg/day. Exemplary preferred doses for oral administration are 0.3 to 30 mg/kg/day, most preferably 1 to 10 mg/kg/day.

For the purposes of this invention, the compounds of the invention may be administered by a variety of means including orally, parenterally, by inhalation spray, topically, or rectally in formulations containing conventional non-toxic pharmaceutically acceptable carriers, adjuvants and vehicles. The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including those from the group consisting of sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophylized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 200 μmoles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 20 to about 50 μmoles of the active ingredient per milliliter of solution in order that infusion of a suitable volume at a rate of about 30 ml/hr can occur.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Examples of use of the method of the invention includes the following. It will be understood that these examples are exemplary and that the method of the invention is not limited solely to these examples.

The method may be used following thrombolysis for coronary occlusion. The compound would be given as a sterile injectable preparation with water or isotonic sodium chloride as the solvent. The solution can be administered intravenously or directly into the coronary artery at the time of left heart catheterization or into a carotid artery. The rate of administration could vary from 0.2 to 1 μmole/min/kg with, for example, an infusion volume of 30 ml/hr. Duration of therapy would typically be about 96 hours.

Angina and early myocardial infarcts can be treated by intravenous administration using a sterile injectable preparation using the rates discussed above.

Compounds of the invention can also be administered to patients intravenously during cardiac bypass surgery or to other surgical patients at risk for a myocardial infarct. The compound can be added directly to the solution administered by the membrane oxygenation, or to the cardiac preservation solution, at the rates discussed above.

Organs can be preserved using the method of the invention by perfusing the organ with a solution containing a compound of the invention. The dosage administered would vary with the rate of perfusion of the organ, as is well understood to those skilled in the art. This method is particularly applicable to organs and tissues used in organ transplantation.

DESCRIPTION OF PREFERRED EMBODIMENTS

Figure 2A:
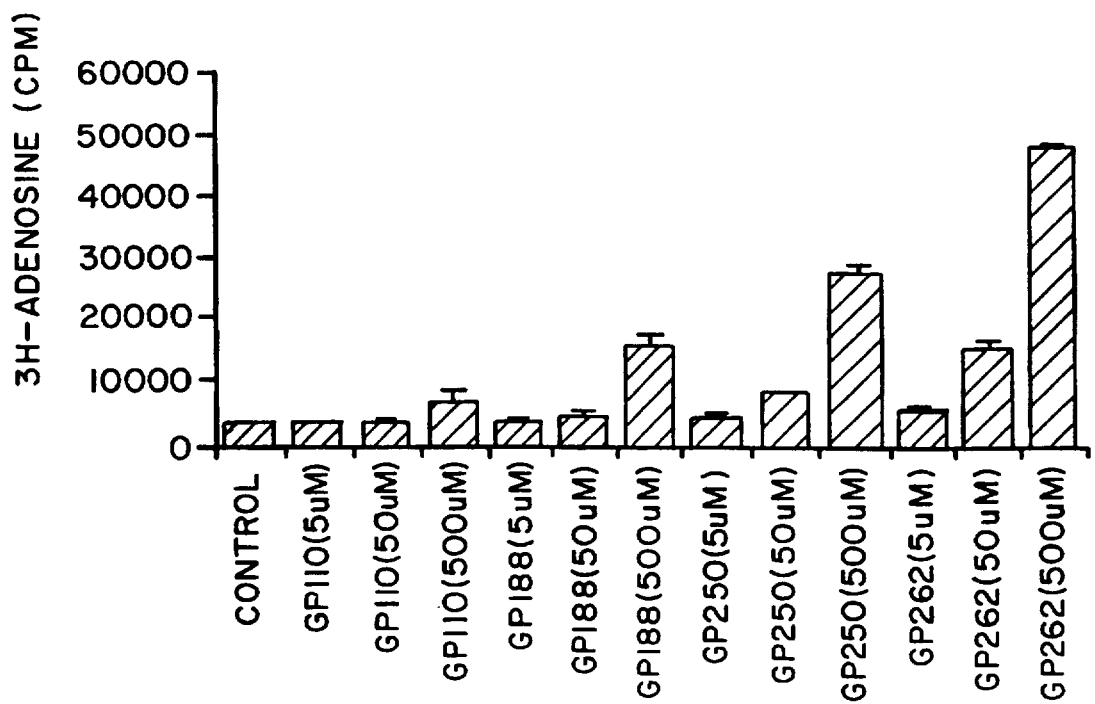
FIG. 2 depicts a comparison of the effect of AICA riboside (Compound No. 1 and a series of 2'-(Series IV) substituted AICA riboside analogs (Compound Nos. 20 (1-188), 34(1-250) and 32 (1-262)) on utilization of adenosine (together with inosine and hypoxanthine) in a cell culture model.
Figure 2B:
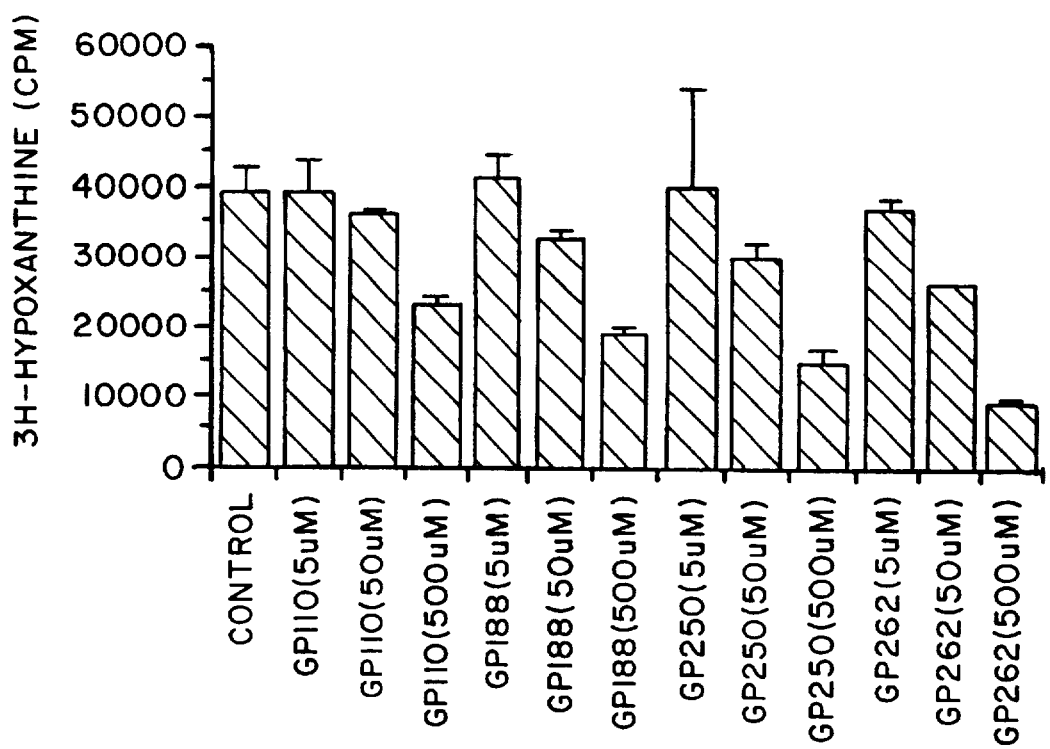
Figure 2C:
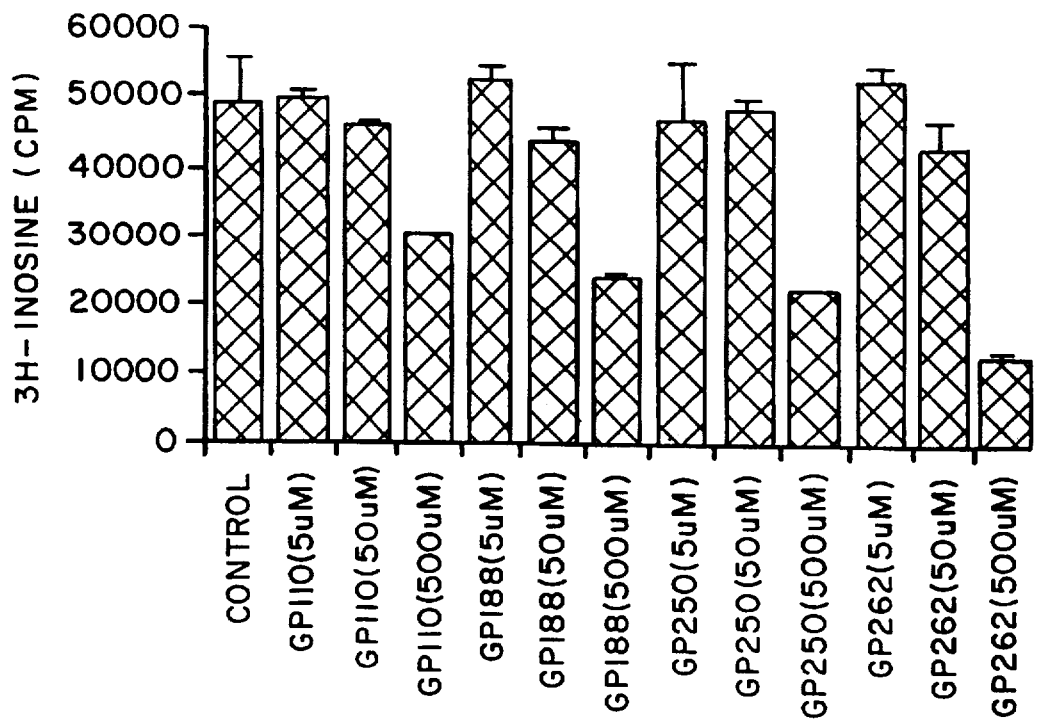

We have identified a number of analogs of AICA riboside that improve the recovery of post-ischemic function in experimental models of ischemia. As shown in Table I, the benefit that results from treatment with the preferred analogs is at least equal to AICA riboside (Compounds Nos. 11, 40 (Series I), and 19 (Series III)), and in many examples achieved at lower concentrations than AICA riboside (e.g. Compound Nos. 10, 23, 25, 29, 47, 52, 53 (Series I), 27 (Series II), 21, and 66 (Series III)). Preferred compounds include prodrugs, such as carboxylic acid esters of the 2' and 3' hydroxyls. For example, preferred prodrugs of Series IIII are those where $R^4$ and $R_5$ (Formula I) together form a cyclic carbonate. In functional assays, which specifically evaluate compounds for their ability to increase extracellular adenosine levels, many of these preferred analogs show markedly enhanced potency compared to AICA riboside. The results of evaluating the compounds for their ability to inhibit stimulated contraction in the isolated ileum, an adenosine-mediated functional response, showed that these compounds in each of the preferred series were more effective than AICA riboside (Table II). In addition, the N-4 substituted AICA riboside analogs (Series I) enhanced both tissue adenosine levels in ischemic rat hearts (Table III) and inhibited adenosine utilization in coronary endothelial cells (Table IV) to a significantly greater degree than AICA riboside. A number of compounds from this preferred series (I) also bind with greater affinity to the NBTI-specific adenosine transport site (Table V). These data suggest that the improved functional benefit of this preferred analog series compared to AICA riboside arises, at least in part, from their ability to increase extracellular adenosine levels and that this ability may be accounted for by inhibition of adenosine transport. (See Table V and FIGS. 4 and 5). The C-2 substituted AICA riboside analogs (Series II) also appear to augment adenosine release as exemplified by the effects of Compound No. 13 on adenosine production in cell culture (Table VI). Moreover, certain of these compounds are inhibitors of the adenosine metabolizing enzyme, adenosine kinase (see Table VII). The 2'-C substituted AICA riboside analogs (Series IV) profoundly modulate adenosine utilization in a cell culture model (FIGS. 2A, 2B and 2C). In this preferred series (IV), each of the test compounds is also an effective inhibitor of adenosine deaminase, another important adenosine-metabolizing enzyme (Table VII). Thus, these compounds increase extracellular adenosine levels more effectively than AICA riboside and this can be explained by enhanced inhibition of adenosine deaminase.

AICA riboside analogs have also been evaluated for their effects on platelet function. As shown in Table IX, certain compounds inhibit platelet aggregation in human whole blood. Inhibition of platelet aggregation by many of the test compounds is enhanced in the presence of a non-inhibitory concentration of adenosine. Adenosine has been reported to be a potent antiplatelet agent, but with a short half life in blood. Accordingly, the inhibition of platelet aggregation observed in the presence of these AICA riboside analogs may be due to the adenosine regulating activity of these compounds.

Figure 3:
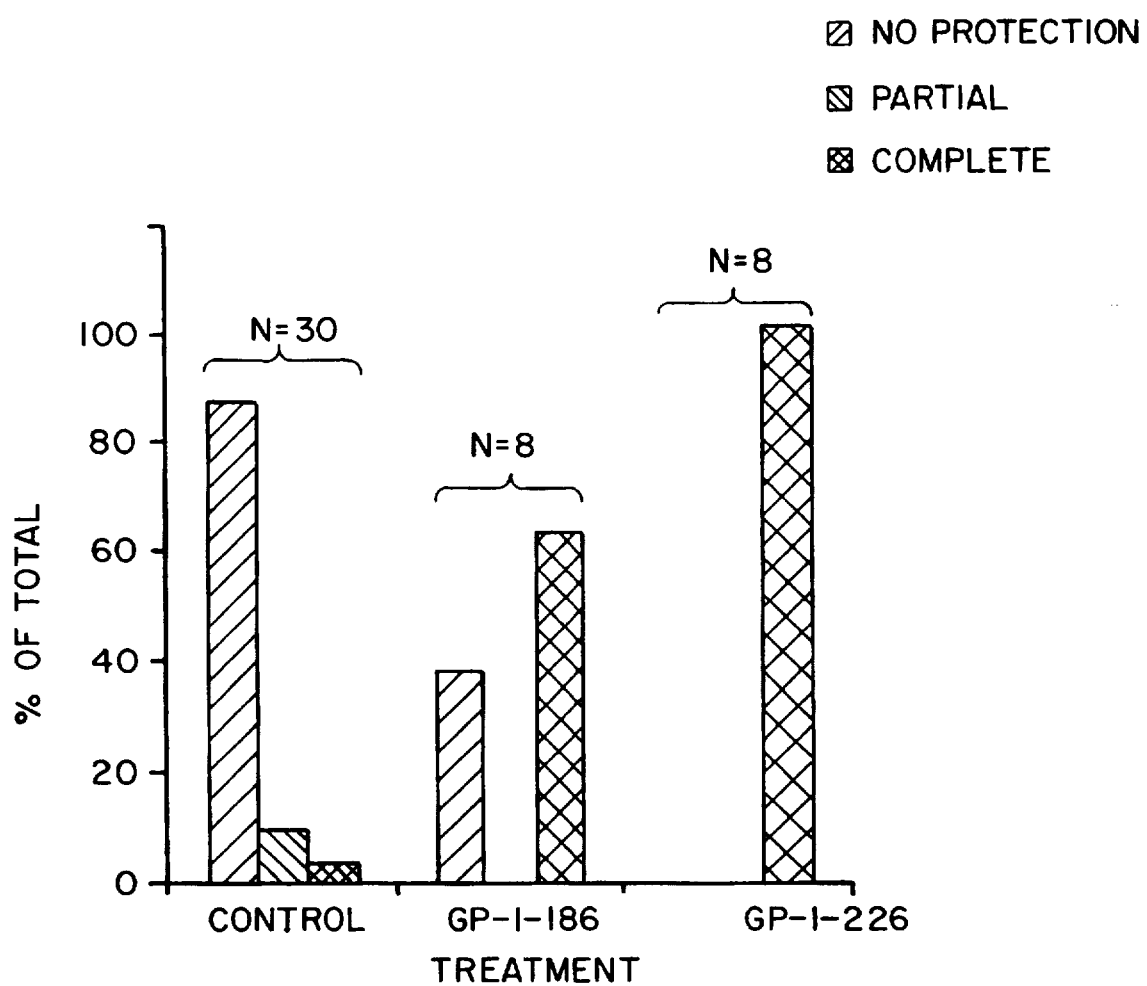
FIG. 3 depicts the effects of N-4 (Series I) substituted AICA riboside analogs (Compound Nos. 10(1-186) and 11(1-226)) in a gerbil brain ischemia model.

Certain preferred AICA riboside analogs (Compound No. 53 (1-468), Compound No. 21 (1-227)) are also orally bioavailable in the dog (see Table X). Furthermore, treatment with the AICA riboside analog Compound No. 53 (1-468), provided functional benefits in a canine model of stable angina (see Table XI). In addition to their cardiovascular benefits, certain AICA riboside analogs (Compound Nos. 10 (1-186) and 11 (1-226) (Series I)) also have demonstrated protective effects in a gerbil model of brain ischemia (FIG. 3).

To assist in understanding the invention, the results of a series of experiments are presented that demonstrate the benefit of these preferred analogs in models of ischemia and, moreover, provide a rationale for these analogs exhibiting enhanced potency compared to AICA riboside. Also presented are a series of Examples which exemplify the synthesis of these compounds. These examples should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

IMPROVED FUNCTIONAL RECOVERY IN ISOLATED HEARTS

The ability of a number of the preferred AICA riboside analogs to improve recovery of post-ischemic cardiac function was examined in an isolated rat heart model.

Isolated rat hearts were cannulated via the ascending aorta and attached to a perfusion apparatus according to the method of Langendorff. The hearts were perfused at a constant pressure of 100 cm of $H_2O$ with a modified Krebs-Henseleit buffer (pH 7.4) at 37° C. As a measure of heart function, left ventricular developed pressure (LVDP) was continuously monitored. Following equilibration of the hearts for a period of 30 min., the hearts were subjected to reduced flow i.e. ischemia, by reducing the pressure to 10 cm of $H_2O$ for 30 min. Flow was then restored by returning the pressure to its original level (100 cm of $H_2O$) for a further 30 min. Each of the AICA riboside analogs together with AICA riboside itself, for comparison, was added to the perfusion buffer to a final concentration of 5 µM or 20 µM. The results are shown in Table I.

TABLE I

| Series | Compound No. | Conc. (µM) | Function Recovery % Baseline LVDP (# of hearts) | P value |
|---|---|---|---|---|
| | Perfusion Buffer Control (Post Ischemia) | — | 64.9 ± 0.7 (125) | — |
| | 1 (1-110) | 20 | 79.4 ± 1.3 (34) | .0001 |
| | | 5 | 64.2 ± 1.5 (6) | NS[1] |
| I | 10 (1-186) | 20 | 84.5 ± 3.5 (2) | .0024 |
| | | 5 | 83.7 ± 0.7 (6) | .0001 |
| | 11 (1-226) | 20 | 85.7 ± 6.2 (3) | .0002 |
| | | 5 | 77.2 ± 5.8 (7) | NS[1] |
| | 16 (1-273)[2] | 5 | 83.1 ± 3.2 (5) | .0001 |
| | 23 (1-343) | 1 | 79.0 ± 2.3 (6) | .0002 |
| | 25 (1-360) | 5 | 86.8 ± 2.3 (6) | .0001 |
| | | | 72.4 ± 1.6 (6) | .0289 |
| | 37 (1-270) | 5 | 71.9 ± 3.0 (5) | .0500 |
| | 29 (1-349) | 1 | 76.7 ± 2.9 (7) | .0028 |
| | 40 (1-392)[2] | 20 | 78.5 ± 3.7 (8) | <.005 |
| | 47 (1-450) | 1 | 74.0 ± 2.8 (6) | .0045 |
| | 52 (1-467) | 5 | 86.0 ± 2.5 (5) | .0001 |
| | 53 (1-468) | 5 | 85.6 ± 1.8 (10) | .0001 |
| | 59 (1-506) | 1 | 75.8 ± 2.2 (7) | .0001 |
| | 68 (1-538) | 5 | 75.3 ± 2.2 (4) | .0033 |
| | 69 (1-549) | 5 | 77.0 ± 2.8 (6) | .0002 |
| | 74 (1-572) | 5 | 73.3 ± 3.3 (6) | .0012 |
| II | 27 (1-395) | 5 | 74.6 ± 3.7 (7) | .0060 |
| | 67 (1-535) | 5 | 77.4 ± 5.7 (3) | .0045 |
| III | 19 (1-154) | 20 | 85.5 ± 1.7 (5) | .0001 |
| | 21 (1-227) | 5 | 81.0 ± 3.2 (8) | .0001 |
| | | 1 | 77.0 ± 4.4 (10) | .0007 |
| | 26 (1-332) | 5 | 70.7 ± 4.1 (8) | .0466 |
| | 62 (1-510) | 5 | 75.5 ± 2.3 (4) | .0049 |
| | 63 (1-517) | 5 | 79.7 ± 4.8 (4) | .0001 |
| | 65 (1-522) | 5 | 72.3 ± 5.6 (4) | .0410 |
| | 66 (1-531) | 5 | 88.5 ± 1.8 (5) | .0001 |
| | 76 (1-578) | 5 | 74.0 ± 2.5 (6) | .0016 |

[1]NS = not significant
[2]Known compound

Example 2

INHIBITION OF CONTRACTION IN ISOLATED ILEUM

The ability of the preferred AICA riboside analogs to inhibit stimulated contraction of muscle strips from the isolated ileum has been compared.

Segments (~1 cm) of longitudinal muscle were stripped from the guinea pig ileum, connected to isotonic force transducers and suspended in jacketed tissue baths containing Krebs-Ringer Solution aerated with 95% $O_2$/5% $CO_2$. Parallel platinum electrodes were used to deliver electrical current at 1 minute intervals at a voltage adequate to induce contraction of 90% of maximal. Test compounds were added to the tissue baths and the concentrations which inhibited contraction by 50%, ($IC_{50}$) determined. These are detailed in Table II.

TABLE II

| Series | Compound No. | IC$_{50}$ (μM) |
|---|---|---|
|   | 1 (1-110) | >1000 |
| I | 11 (1-226) | 200 |
|   | 12 (1-232) | 400 |
|   | 23 (1-343) | 3 |
|   | 24 (1-354) | 400 |
|   | 25 (1-360) | 20 |
|   | 29 (1-349) | 60 |
|   | 35 (1-355) | 60 |
|   | 39 (1-390) | 500 |
|   | 41 (1-396) | 100 |
|   | 42 (1-431) | 6 |
|   | 44 (1-434) | 20 |
|   | 45 (1-438) | 100 |
|   | 47 (1-450) | 10 |
|   | 53 (1-468) | 70 |
|   | 30 (1-388) | 20 |
| II | 27 (1-395) | 500 |
|   | 43 (1-432) | 200 |
| III | 21 (1-227) | 800 |
|   | 26 (1-332) | 200 |
| IV | 32 (1-262) | 100 |

Example 3

EFFECT OF AICA RIBOSIDE ANALOGS (SERIES I) IN THE RAT HEART ISCHEMIA MODEL

Series I(N-4) substituted AICA riboside analogs were tested for their ability to enhance tissue adenosine levels in ischemic rat hearts.

Male rats were injected intraperitonealy with either the AICA riboside analog, AICA riboside or saline, as a control. After 60 minutes, the hearts were excised and incubated at 37° C. for a further 60 minutes. Tissue extracts were prepared and analyzed for adenosine by high performance liquid chromatography (HPLC). The ability of this preferred series of AICA riboside analogs to increase tissue adenosine levels compared to AICA riboside is shown in Table III. A more detailed comparison of the dose-dependent effects on tissue adenosine levels of a selected AICA riboside analog in this preferred series (Compound No. 10) compared to AICA riboside (Compound No. 1) is shown in FIG. 1.

TABLE III

| Compound No. | Tissue Adenosine Levels (% Increase vs. Saline) |
|---|---|
| 1 (1-110) | 30 |
| 10 (1-186) (Expt 1) | 79 |
| 10 (1-186) (Expt 2) | 68 |
| 11 (1-226) (Expt 1) | 53 |
| 11 (1-226) (Expt 2) | 45 |
| 12 (1-232) | 29 |
| 36 (1-207) | 34 |

Example 4

INHIBITION OF ADENOSINE UTILIZATION BY AICA RIBOSIDE ANALOGS (SERIES I) IN CELL CULTURE

Effects of Series I (N-4) substituted AICA riboside analogs on adenosine utilization were compared using coronary endothelial cells in culture. In this assay, endothelial cells were incubated with 5 μM or 50 μM of the test compound together with 1 μM [$^3$H] adenosine for 15 minutes. Inhibition of adenosine utilization was determined by measuring the concentration of extracellular adenosine by scintillation counting following separation by thin layer chromatography (TLC). The results of this evaluation are shown in Table IV.

TABLE IV

| | Inhibition of Adenosine Utilization (%) | |
|---|---|---|
| Compound No. | 5 μM | 50 μM |
| 1 (1-110) | 5 ± 2 | 10 ± 1 |
| 23 (1-343) | 27 ± 4 | 63 ± 2 |
| 28 (1-348) | 17 ± 3 | 47 ± 2 |
| 29 (1-349) | 41 ± 11 | 67 ± 8 |
| 25 (1-360) | 21 ± 1 | 56 ± 2 |
| 30 (1-388) | 21 ± 1 | 49 ± 4 |
| 38 (1-351)[2] | 16 ± 1 | 44 ± 0 |
| 39 (1-390) | 7 ± 4 | 29 ± 1 |
| 46 (1-445) | 19 ± 4 | 30 ± 9 |
| 47 (1-450) | 17 ± 3 | 19 ± 2 |
| 48 (1-452) | 23 ± 3 | 25 ± 2 |
| 49 (1-453) | 30 ± 4 | 33 ± 8 |
| 51 (1-466) | 27 ± 2 | 65 ± 2 |
| 52 (1-467) | 56 ± 2 | 71 ± 1 |
| 53 (1-468) | 34 ± 4 | 58 ± 2 |
| 56 (1-487) | 55 ± 7 | 65 ± 9 |
| 61 (1-509) | 37 ± 28 | 72 ± 5 |
| 71 (1-562) | 10 ± 3 | 31 ± 11 |
| 73 (1-566) | 16 ± 0 | 33 ± 9 |
| 75 (1-577) | 8 ± 0 | 30 ± 3 |

[2]Known compound

Example 5

EFFECT OF AICA RIBOSIDE ANALOGS (SERIES I) IN [$^3$H]-NBTI BINDING ASSAY

The ability of selected Series I (N-4) substituted AICA riboside analogs to effect the binding of [$^3$H]-nitrobenzyl-thioinosine (NBTI) to cell membranes was compared. Increasing concentrations of the test compounds were incubated for 30 minutes with 0.5 mg neuronal membrane protein together with 0.5 nM [$^3$H]-NBTI in a Tris buffer (pH 7.4) at room temperature. The assays were quenched and membranes collected by rapid filtration. Filters were then solubilized and radioactivity determined by scintillation counting. The concentration of each test compound which resulted in 50% displacement of bound [$^3$H]-NBTI, the ED$_{50}$'s, are detailed in Table V.

TABLE V

| Series | Compound No. | ED$_{50}$ (μM) |
|---|---|---|
|   | 1 (1-110) | >1000 |
| I | 10 (1-186) | 350 |
|   | 24 (1-354) | 300 |
|   | 35 (1-355) | 190 |
|   | 29 (1-349) | 100 |
|   | 25 (1-360) | 72 |
|   | 28 (1-348) | 15 |
|   | 23 (1-343) | 3 |
|   | 30 (1-388) | 225 |
|   | 39 (1-390) | 600 |
|   | 44 (1-434) | 100 |
|   | 45 (1-438) | 90 |
|   | 46 (1-445) | 8 |
|   | 47 (1-450) | 0.5 |
|   | 48 (1-452) | 22 |
|   | 49 (1-453) | 7 |
|   | 50 (1-459) | 28 |
|   | 51 (1-466) | 16 |
|   | 52 (1-467) | 80 |

TABLE V-continued

| Series | Compound No. | ED$_{50}$ (µM) |
|---|---|---|
| | 53 (1-468) | about 100 |
| | 55 (1-484) | 60 |
| | 56 (1-487) | 32 |
| | 57 (1-488) | 80 |
| | 58 (1-489) | 80 |
| | 59 (1-506) | 2 |
| | 60 (1-508) | 17 |
| | 61 (1-509) | 32 |
| | 64 (1-519) | 48 |
| II | 27 (1-395) | 344 |
| | 43 (1-432) | 71 |
| III | 54 (1-483) | 28 |

Example 5A
INHIBITION OF ADENOSINE TRANSPORT IN WI-L2 LYMPHOBLASTS

Inhibition of adenosine transport in WI-L2 lymphoblasts in the presence of one of the AICA riboside analogs of the present invention was determined according to the following procedure.

A 200 µl aliquot of WI-L2 lymphoblast cell suspension (0.5×106) was layered on top of 100 µl of a silicone oil: mineral oil mixture (8:2 by volume). Compound No. 53 (1-468) at concentrations of 5.0, 50.0 and 500.0 µM, respectively, was added to the cells and the resulting mixture was incubated for either 1 minute or 1 hour. Then, 5 µl of radiolabelled adenosine (2.5 µCi initial concentration of 1 µM) were added to the cell suspension and the mixture was incubated for 10 seconds. Cells were then centrifuged for 15 seconds at 13,000 rpm and the cell pellets were measured for radioactivity.

Figure 4:
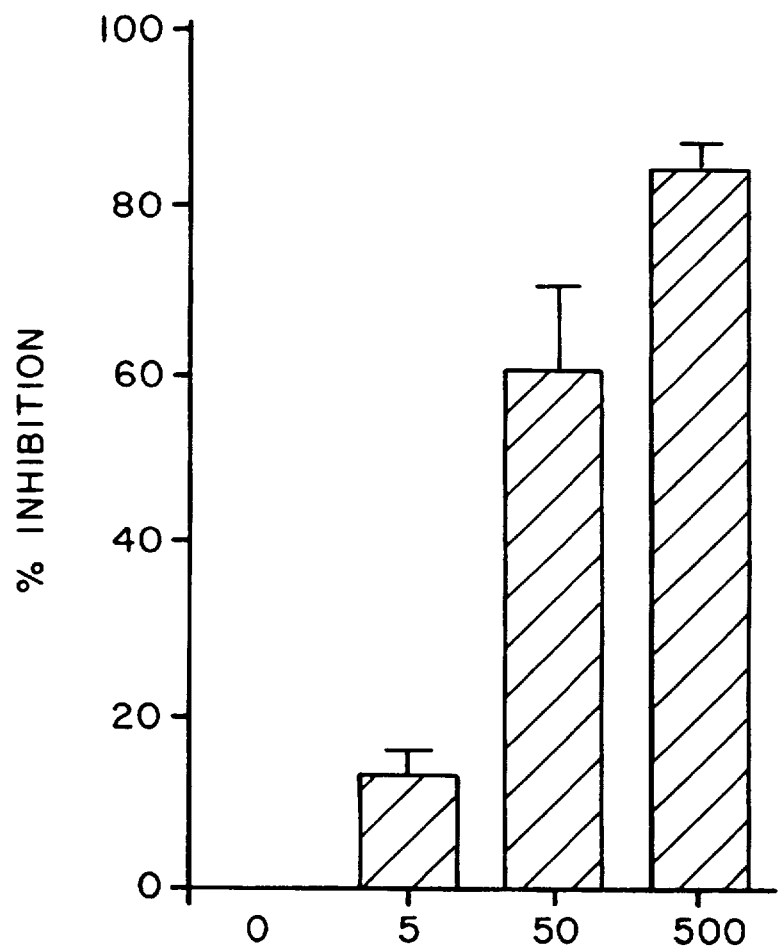
FIG. 4 depicts inhibition of adenosine transport in WI-L2 lymphoblasts after 1 minute preincubation with Compound No. 53 (1-468) at the noted concentrations.
Figure 5:
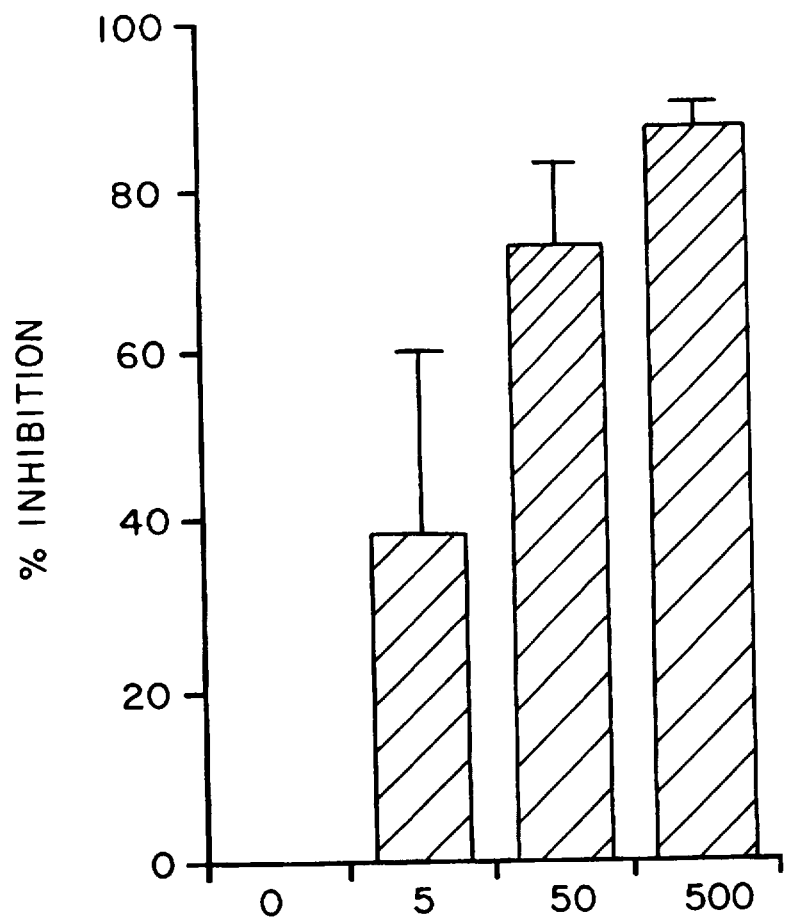
FIG. 5 depicts inhibition of adenosine transport in WI-L2 lymphoblasts after 1 hour preincubation with Compound No. 53 (1-468) at the noted concentrations.

FIG. 4 depicts inhibition of adenosine transport with 1 minute preincubation with compound No. 53 (1-468) and FIG. 5 depicts inhibition of adenosine transport with 1 hour preincubation with compound No. 53 (1-468).

Example 6
EFFECT OF AN AICA RIBOSIDE ANALOG (SERIES III) ON ADENOSINE RELEASE FROM ISOLATED CELLS A Series II (C-2)-substituted AICA riboside analog was compared with AICA riboside itself for its ability to influence adenosine release from coronary endothelial cells. In this experimental model the cells were treated with 50 µM of the test compound and incubated for 16 hours at 37° C. Cells were then washed with phosphate-buffered saline and resuspended in standard culture medium containing no glucose (to inhibit glycolysis), 50 µM antimycin A (to inhibit oxidative phosphorylation) and 20 µM deoxycoformycin (to inhibit adenosine utilization by adenosine deaminase). This treatment was designed to simulate ischemic condition by inducing net ATP breakdown. Media was then processed for HPLC. Adenosine values are given in Table VI.

TABLE VI

| Compound No. | Extracellular Adenosine Levels (µM) | Increase (%) |
|---|---|---|
| Control | 1.42 ± 0.17 | — |
| 1 (1-110) | 1.64 ± 0.12 | 15.5 |
| 13 (1-240) | 2.79 ± 0.19 | 96.5 |

Example 7
EFFECT OF AICA RIBOSIDE ANALOGS (SERIES II) ON ADENOSINE KINASE ACTIVITY Inhibition of enzyme activity was determined using a 0.1 ml assay mixture containing 50 mM Tris-maleate, pH 7.0, 0.1% (w/v) BSA, 1 mM ATP, 1 mM MgCl$_2$, 0.5 µM [U-$^{14}$C] adenosine (500 mCi/mmol) and 0.1 µg of purified pig heart adenosine kinase. Different concentrations of test compound were incubated in the assay mixture for 20 minutes at 37° C. From each reaction mixture, 20 µl portions were removed and spotted on 2 cm$^2$ pieces of Whatman DE81 filter paper. The papers were then washed to remove [$^{14}$C] adenosine in 1 mM ammonium formate followed by deionized water and finally 95% ethanol. The papers were dried, and [$^{14}$C] AMP measured by scintillation counting. Activities were determined from the amount of [$^{14}$C] AMP formed.

The results are shown in Table VII.

TABLE VII

| Compound No. | IC$_{50}$ (µM) |
|---|---|
| 1 (1-110) | >5000 |
| 27 (1-395) | 8 |
| 67 (1-535) | 23 |
| 70 (1-551) | 17 |

Example 8
EFFECT OF AICA RIBOSIDE ANALOGS (SERIES IV) ON ADENOSINE UTILIZATION IN ISOLATED CELLS Series IV 2'-substituted AICA riboside analogs were tested for their ability to inhibit adenosine utilization in human B lymphoblasts. In this assay, cells were preincubated with the test compound at a concentration of 5 µM, 50 µM or 500 µM together with [$^3$H]-adenosine (1 µM) for a period of 10 minutes. Inhibition of adenosine utilization was determined from the extracellular concentration of [$^3$H] adenosine measured by scintillation counting following separation of the nucleosides by TLC. Hypoxanthine and inosine levels were also measured. The results from a comparison of 2'-O-methyl (Compound No. 20) 2'-O-ethyl (Compound No. 34) and 2'-O-n-butyl (Compound No. 32) analogs of AICA riboside compared to AICA riboside are shown in FIG. 2A.

The effects of these AICA riboside analogs on hypoxanthine and inosine levels (shown in FIG. 2B and 2C respectively) mirror those effects on adenosine levels suggesting an augmented influence on adenosine utilization mediated by inhibition of adenosine deaminase. This interpretation is supported by direct measurement of the ability of the analogs to inhibit the isolated adenosine deaminase Inhibition of adenosine deaminase activity was determined spectrophotometrically using a 1 ml assay mixture containing 50 mM potassium phosphate, pH 7.0, 1 mM alphaketoglutarate, 15 units glutamic dehydrogenase, 0.125 mM NADH, 80 µM adenosine and 0.002 units of calf intestinal musosa adenosine deaminase. Different concentrations of the test compounds were incubated in the assay mixture for 10 minutes at 37° C. The reaction was monitored continuously for oxidation of NADH from the change in absorbance at 340 nm.

The results are shown in Table VIII.

TABLE VIII

| Compound No. | IC$_{50}$ (µM) |
|---|---|
| 1 (1-110) | >5000 |
| 20 (1-188) | 1400 |
| 34 (1-250) | 510 |
| 32 (1-262) | 175 |

Example 9

EFFECT OF AICA RIBOSIDE ANALOGS ON INHIBITION OF PLATELET AGGREGATION IN HUMAN WHOLE BLOOD

The ability of preferred AICA riboside analogs to inhibit platelet aggregation was examined in human whole blood. Whole blood was drawn from healthy donors and collected in 0.1 vol. of sodium citrate to prevent coagulation. Platelet aggregation was measured by the impedance technique using a Whole Blood Aggregometer. The test compounds were incubated in whole blood for 10 minutes at 37° C. and 10 gM adenosine was added 5 minutes before eliciting aggregation. Aggregation was induced by addition of ADP (6–25 µM) at the minimum concentration inducing full aggregation in untreated controls.

The results are shown in Table IX.

TABLE IX

| Series | Compound No. | IC$_{50}$ (µM) |
|---|---|---|
|  | 1 (1-110) | 2700 |
| I | 4 (1-122) | 200 |
|  | 23 (1-343) | 38 |
|  | 28 (1-348) | 180 |
|  | 29 (1-349) | 90 |
|  | 51 (1-466) | 193 |
|  | 52 (1-467) | 480 |
|  | 53 (1-468) | 150 |
|  | 56 (1-487) | 75 |
|  | 59 (1-506) | 70 |
|  | 61 (1-509) | 171 |
|  | 71 (1-562) | 40 |
|  | 72 (1-563) | 300 |
| II | 27 (1-395) | 950 |
|  | 43 (1-432) | 620 |
| IV | 32 (1-262) | 350 |

Example 10

ENHANCED ORAL BIOAVAILABILITY AND HALF-LIFE OF AICA RIBOSIDE ANALOGS

Certain preferred AICA riboside analogs were evaluated for enhanced oral bioavailability in fasted adult beagles. AICA riboside analogs were given as a 10 mg/kg IV bolus via a cephalic leg vein and as a 20 mg/kg solution administered via a stomach tube. Heparinized blood and urine were collected at selected intervals over 24 hours. Each sample was chilled, centrifuged at 4° C. and frozen prior to HPLC analysis.

The results are shown in Table X.

TABLE X

| Series | Compound No. | Absolute Oral Bioavailability % | Half Life (hours) |
|---|---|---|---|
|  | 1 (1-110) | 8 ± 4 (n = 7) | 0.35 |
| I | 53 (1-468) | 32 ± 11 (n = 2) | 5.61 |
| III | 21 (1-227) | 71 ± 13 (n = 2) | 1.30 |

Example 11

FUNCTIONAL BENEFITS OF COMPOUND NO. 53(1-468) IN A PRECLINICAL MODEL OF STABLE ANGINA

The AICA riboside analog (1-468) was evaluated for its ability to prevent cumulative cardiac dysfunction associated with repeated episodes of demand-induced ischemia. Anesthetized male dogs were instrumented to measure regional myocardial wall thickening during right atrial pacing in the presence of a stenosis of the left anterior descending artery (Young & Mullane Am. J. Physiol. in press (1991)). In Table XIA, the effects on wall thickening and arterial pressure of six repeated episodes of pacing in animals treated with a continuous IV infusion of 50 µg/kg/min of the test compound administered post-pace #1 are compared with saline-treated control animals. In Table XIB, the change in heart rate and mean arterial pressure in the post-pace rest period are listed, demonstrating that preservation of wall thickening occurred in the absence of significant hemodynamic effects.

TABLE XIA

| | % of NON-ISCHEMIC WALL THICKENING | |
|---|---|---|
| Pace # | Saline (N = 9) | Compound No. 53 (n = 6) |
| 1 | 41.6 ± 2.6 | 49.5 ± 6.5 |
| 2 | 31.7 ± 4.6 | 46.7 ± 7.0 |
| 3 | 25.8 ± 5.6 | 54.2 ± 9.4* |
| 4 | 18.5 ± 5.5 | 48.1 ± 7.6* |
| 5 | 11.8 ± 5.6 | 47.5 ± 8.2* |
| 6 | 12.4 ± 6.0 | 42.1 ± 7.0* |

*$P < 0.05$ vs. saline

TABLE XIB

| | Post Pace Rest Period (Change from Baseline) | | | | | | |
|---|---|---|---|---|---|---|---|
| | Baseline | 1 | 2 | 3 | 4 | 5 | 6 |
| Mean Arterial Pressure (mm Hg) | | | | | | | |
| Saline | 86 ± 2 | 0 ± 1 | −2 ± 2 | −1 ± 2 | −3 ± 2 | −2 ± 2 | −2 ± 2 |
| Test Compound | 86 ± 5 | −1 ± 3 | −2 ± 3 | −8 ± 3 | −7 ± 3 | −8 ± 3 | −7 ± 3 |
| Heart Rate (beats/min) | | | | | | | |
| Saline | 113 ± 7 | 2 ± 2 | 4 ± 3 | 8 ± 3 | 9 ± 4 | 11 ± 5 | 13 ± 5 |
| Test Compound | 143 ± 6 | 1 ± 2 | −2 ± 4 | −1 ± 3 | 2 ± 4 | 1 ± 4 | 2 ± 4 |

Example 12

EFFECT OF AICA RIBOSIDE ANALOGS (SERIES I) IN AN EXPERIMENTAL STROKE MODEL

The ability of Series I (N-4) substituted AICA riboside analogs to effect hippocampal pyramidal cell survival in a gerbil stroke model was evaluated. In this test, male Mongolian gerbils were anesthetized with 2–3% halothane in $N_2O:O_2$ and the common carotid arteries exposed. Ischemia was then induced by bilateral occlusion of both common carotid arteries for 5 minutes. Seven days following the ischemic insult, brains were removed and processed for histology. The data presented in FIG. 3 shows the effect of pretreatment of the gerbils with 500 mg/kg of the AICA riboside analogs (Compound Nos. 10 (1-186) or 11 (1-226)) or with saline, as a control.

Example A

Preparation Of 5-Amino-(2,3,5-tri-O-acetyl-beta-D-ribofuranosyl)imidazole-4-carboxamide (Compound No. 2 (1-111))

AICA riboside (50 g) was dissolved in pyridine (450 ml) and then cooled in an ice bath. Acetic anhydride (80 ml) was added and the ice bath removed. The reaction mixture was stirred for 3 hrs. TLC on silica gel, eluting with 9:1 methylene chloride:methanol, showed the reaction to be complete. Methanol (5 ml) was added to neutralize unreacted acetic anhydride. The solvents were removed by evaporation under high vacuum (bath temperature less than 40° C). The residue was coevaporated with dimethylformamide (3×150 ml). The residue was crystallized from ethanol using seed crystals. The yield of the triacetate 62 g of white solid; melting point 128°–129° C.

NMR (DMSO-d$_6$) δ ppm 2.05–2.15 (2s, 9H, —CH$_3$), 4.3 (broad s, 3H, 4'-CH, 5'-CH$_2$), 5.3 (m, 1H, 3'-CH) 5.55 (t, 1H, 2'-CH), 5.87 (d, 1H, 1'-CH), 5.9 (broad s, 2H, 5-NH$_2$), 6.7–6.9 (broad d, 2H, 4-NH$_2$), 7.4 (s, 1H, 2-CH).

The preparation this compound is also described in U.S. Pat. No. 3,450,693 to K. Suzuki & I. Kumoshiro (1969); See also Chem. Abs. 71: 816982 (1969).

Example B

Preparation of N$^5$-dimethylaminomethyleneamino-beta-D-ribofuranosylimidazole-4-carboxamide (Compound No. 7 (1-164))

Dissolved 2',3',5'-tri-O-acetyl AICA riboside (10 g) in dimethylformamide (30 ml) and dimethylformamide dimethyl acetal (20 ml). The reaction mixture was allowed to stir overnight. TLC on silica gel, eluting with 9:1 methylene chloride:methanol, showed that the reaction was complete by absence of starting material. The solvent was removed by evaporation under high vacuum (bath temperature less than 40° C.). The residue was dissolved in cyclohexylamine and stirred overnight. The solvent was removed by evaporation under reduced pressure and the residue was crystallized from ethanol. Yield was 4.6 g of white solid, melting point 173°–175° C.

NMR (MeOH-d$_4$), δ ppm 3.0–3.05 (2s, 6H, N(CH$_3$)$_2$), 3.75 (m, 2H, 5'-CH$_2$), 4.0 (g, 1H, 4'-CH), 4.2 (t, 1H, 3'-CH), 4.35 (t, 1H, 2'-CH), 5.8 (d, 1H, 1'-CH), 7.7 (s, 1H, 2-CH), 8.25 (s, 1H, 5-N=CH—N)

Example C

Preparation of 5-Amino-1-beta-D-ribofuranosylimidazole-4-N-(cyclopentyl) carboxamide (Compound No. 10 (1-186))

The literature procedure of P. C. Srivastava, R. W. Mancuso, R. J. Rosseau and R. K. Robins, J. Med. Chem. 17(11), 1207 (1977) was followed to synthesize N-succinimidyl-5-amino-1-(2,3,5-tri-O-acetyl-β-D-ribofuranosyl)imidazole-4-carboxylate ("intermediate No. 4"). Intermediate No. 4 (3.9 g) was dissolved in methylene chloride (60 ml). Cyclopentylamine (0.8 ml) was added and the solution was stirred overnight. TLC on silica, eluting with 9:1 methylene chloride:methanol, showed the reaction was complete by absence of starting material. The solvent mixture was extracted with 5% hydrochloric acid solution (100 ml), saturated sodium bicarbonate solution (100 ml, and water (200 ml). The organic layer was dried over sodium sulfate and evaporated under reduced pressure to give 3.1 g of yellow foam. The acetyl groups were removed by dissolving the 3.1 g of foam in methanol (70 ml) and cooling in an ice bath. Ammonium hydroxide (60 ml) was added and the ice bath was removed. After 2½ hours stirring, TLC or silica gel, eluting with 9:1 methylene chloride:methanol showed all starting material was gone. The solvent was evaporated under reduced pressure to give a residue which was purified on a silica column, eluting with 9:1 and 6: methylene chloride:methanol. Fractions which were alike by TLC were pooled and evaporated under reduced pressure to yield 1.1 g of white foam crystallized from methanol-ethy acetate, melting point 158°–160° C.

NMR (DMSO-d$_6$), δ ppm 1.4–1.9 (m, 8H, —CH$_2$—CH$_2$—), 3.6 (m, 2H, 5'-CH$_2$), 3.9 (d, 1H, NH—CH ) 4.0–4.35 (m, 3H, 2',3',4'-CH), 5.15–5.4 (m, 3H, 2',3',5'-OH) 5.45 (d, 1H, 1'-CH), 5.9 (broad s, 2H, —NH$_2$), 7.1 (d, 1H —NH—), 7.3 (s, 1H, 2—CH).

Example D

Preparation of 5-Amino-1-beta-D-ribofuranosylimidazole-4-N-(cyclopropyl) carboxamide (Compound No. 12 (1-232))

This compound was prepared following the procedur described in Example C except cyclopropylamine (0.5 ml was substituted for cyclopentylamine (0.8 ml). The yield starting with 6.2 g of intermediate No. 4 (the succinate ester) was 2.3 g.

NMR (DMSO-d$_6$) δ ppm 0.5 (m, 4H, CH$_2$—CH$_2$) 2.7 (m, 1H, N—CH), 3.6 (m, 2H, 5'-CH$_2$), 3.8–4.3 (m, 3H, 2',3',4'-CH), 5.15–5.4 (m, 3H, 2',3',5'-OH) 5.45 (d, 1H, 1'-CH), 5.9 (s, 2H, NH$_2$), 7.2 (s, 1H, 2-CH) 7.4 (d, 1H, 4-NH).

Example E

Preparation of 5-Amino-1-beta-D-ribofuranosylimidazole-4-N-(benzyl)carboxamide (Compound No. 11 (1-226))

Inosine (10 g) was suspended in dimethylformamide (100 ml) and dimethylformamidedibenzylacetal (25 ml). The resulting mixture was stirred at 70° C. overnight. TLC on silica, eluting with 6:1 methylene chloride:methanol, showed completion of reaction. Solvent was removed by evaporation at reduced pressure. The remainder was dissolved in ammonium hydroxide (130 ml). The mixture was stirred overnight, then evaporated under reduced pressure. Ethanol (80 ml) was added to the residue and the resulting mixture was warmed. The solid was collected by filtration. Yield of 1-benzylinosine was 10.5 g which was characterized by NMR.

The intermediate, 1-benzylinosine (10.5 g), was dissolved in ethanol (1.0 L) and 3M sodium hydroxide solution (140 ml). This solution was refluxed for 3 hours. TLC on silica showed the reaction was complete. The solvent was removed by evaporation under reduced pressure. The residue was chromatographed on a silica gel column, eluting with 6:1 methylene chloride:methanol. Fractions were collected which were similar by TLC and concentrated until crystals appeared. Yield was 7.4 g of the above-identified compound as a white solid, melting point 178°–179° C.

NMR (DMSO-d$_6$) δ ppm 3.6 (m, 2H, 5'-CH$_2$) 3.85–4.35 (m, 3H, 2',1',3',4'-CH), 4.4 (d, 2H, N—CH$_2$), 5.15–5.4 (m, 3H, 2',3',5'-OH), 5.5 (d, 1H, 1'-CH), 5.9 (broad s, 2H, 5-NH$_2$), 7.2–7.4 (m, 6H, 2-CH, C$_6$H$_5$) 7.95 (t, 1H, NH).

See also E. Shaw, J.A.C.S. 80: 3899 (1958).

Example F

Preparation of 5-Amino-1-β-D-ribofuranosylimidazole-4-carboxylic acid methyl ester (Compound No. 14 (1-260))

5-amino-1-(2,3,5-tri-O-acetyl-β-D-ribofuranosyl)-imidazole-4-carboxylic acid (3.85 g, 10 mmol) was dissolved in 40 ml tetrahydrofuran and cooled to 0° C. An excess of diazomethane in ether was added and the mixture warmed to room temperature. Acetic acid was added to destroy excess diazomethane and the mixture was evaporated to dryness. The residue was purified by chromatography on silica gel, eluting with 7:3 ethyl acetate:hexane. The major product fractions, judged by silica thin layer chromatography (TLC) using the above system, were combined and evaporated to yield 1.2 g of a white foam. This was dissolved in 40 ml of methanol containing 20 mg of sodium methoxide and stirred for 30 minutes. Silica TLC, eluting with 6:1 methylene chloride:methanol, showed no remaining starting material and a new slower-moving product spot. The reaction was neutralized with Dowex 50 (H$^+$) resin and evaporated to yield 0.64 g of the desired product as a white foam. IR (KBr): 1725 cm$^{-1}$ (—CO—OCH$_3$).

NMR (DMSO-d$_6$): δ ppm, 3.65 (s, 3H, CH$_3$), 3.8 (m, 3H, 4'-CH and 5'-CH$_2$), 4.1 (m, 1H, 3'-CH), 4.2 (m, 1H, 2'-CH), 5.5 (d, 1H, 1'-CH), 8.0 (s, 1H, 2-CH).

Example G

Preparation of 5-Amino-5'-sulfamoyl-1-β-D-ribofuranosyl-imidazole-4-carboxamide (Compound No. 15 (1-261))

A. Preparation of 5-Amino-2',3'-isopropylidene-1-β-ribofuranosyl-5-sulfamoylimidazole-4-carboxamide To a solution of 2',3'-isopropylidene-AICA-riboside (2.98 g, 10 mmol) in dry N,N-dimethylformamide (25 ml), sodium hydride (300 mg, 80% dispersion in oil) was added over a period of 10 min. After the evolution of hydrogen gas had ceased, the flask was immersed in an ice bath and the mixture was stirred for 30 min. A solution of sulfamoyl chloride (1.3 g, 11 mmol) in dry tetrahydrofuran (20 ml) was added slowly. TLC of the reaction mixture (silica gel, solvent 9:1 methylene chloride:methanol) indicated presence of some starting material. An additional 200 mg of sulfamoyl chloride in tetrahydrofuran (10 ml) was added and the resulting mixture stirred for one hour. Methanol (1 ml) was added and solvent was evaporated under high vacuum. The residue chromatographed over silica gel, eluting with a mixture of methylene chloride:methanol (9:1). Several fractions were collected. Fractions showing identical TLC patterns were pooled and evaporated to a glassy product. Yield was 1.5 g.

$^1$H-NMR (DMSO-d$_6$) δ ppm, 1.25 and 1.55 (2s, 6H, C(CH$_3$)$_2$), 4.1 (d, 2H, 5'-CH$_2$), 4.25–4.35 (m, 1H, 4'-CH), 4.8–4.9 and 5.1–5.2 (2m, 2H, 2'-CH and 3'-CH), 5.8 (d, 1H, 1'-CH), 5.9 (s, 2H, 5-NH $_2$), 6.65–6.95 (br. d, 2H, CONH$_2$), 7.35 (s, 1H, 2-CH), 7.7 (s, 2H, SO$_2$NH). The NMR data conformed to the structure of 5-amino-2',3'-isopropylidene-1-β-ribofuranosyl-5'-sulfamoylimidazole-4-carboxamide. This intermediate product was used in the following deblocking step without further purification or isolation.

B. Preparation of 5-Amino-5'-sulfamoyl-1-β-D-ribofuranosyl-imidazole-4-carboxamide (Compound No. 15 (1-261))

The compound from the preceeding preparation was dissolved in 60% formic acid (20 ml) and the resulting solution was stirred at room temperature for 48 hours. The solvent was removed by evaporation under high vacuum. The residue was coevaporated with water. The product was crystallized from aqueous ethanol. Yield was 1.0 g of the above-identified product, melting point 174°–175° C.

$^1$H-NMR (DMSO-d$_6$) δ ppm 3.9–4.3(m, 5H, 2'-CH, 3'-CH, 4'-CH and 5'-CH$_2$), 5.4 and 5.5 (2d, 2H, 2'-OH and 3'-OH), 5.5 (d, 1H, 1'-CH), 5.8 (br.s, 2H, 5-NH$_2$), 6.6–6.9 (br.d, 2H, CONH$_2$), 7.3 (s, 1H, 2-CH) and 7.6 (s, 2H, SO$_2$NH$_2$).

Example H

Preparation of 5'-Amino-5'-deoxy-AICA-riboside (Compound No. 21 (1-227))

A. Preparation of 5'-Azido-5'-deoxy-AICA-riboside

A mixture 5'-deoxy-5'-iodo-2',3'-isopropylidene-AICA riboside (8.0 g) (Ref: P. C. Srivastava, A. R. Newman, T. R. Mathews, and R. K. Robins, J. Med. Chem. 18 1237 (1975)), lithium azide (4.0 g), and N,N-dimethylformamide was heated at 80°–90° C. for 5 hours. The mixture was evaporated to dryness and the residue was chromatographed over silica gel column eluting with methylene chloride. The fast moving product-containing fractions were pooled and evaporated to obtain 7.2 g of a product which was subjected to deblocking with 60% formic acid (100 ml) at room temperature for 48 hours. Excess formic acid was removed by evaporation under high vacuum. The residue was coevaporated with water (3×25 ml) to obtain a semi-solid product. This product was crystallized from aqueous ethanol. Yield was 5.0 g. of the above-identified product, melting point 138°–139° C.

$^1$H NMR (DMSO-d$_6$) δ ppm 3.55 (d, 2H, 5'-CH$_2$), 3.95 (br. s, 2H, 3'-CH and 4'-CH), 4.2–4.4 (m, 1H, 2'-CH), 5.35 and 5.50 (2d, 2H, 2'-OH and 3'-OH), 5.55 (d, 1H, 1'-CH), 5.75–5.9 (br. s, 2H, 5-NH$_2$), 6.6–6.9 (br. d, 2H, CONH$_2$) and 7.35 (s, 1H, 2-CH). IR (KBr) cm$^{-1}$: 3400–3000 (br. NH$_2$, CONH$_2$, OH, etc.), 2150 (S, N$_3$) 1640 (CONH$_2$).

B. Preparation of 5'-Amino-5'-deoxy-AICA-riboside

A solution of 5'-azido-5'-deoxy-AICA-riboside (800 mg) (the product of step (A)) in methanol (40 ml) was hydrogenated in a Parr apparatus with palladium on carbon (5%) (100 mg) as the hydrogenation catalyst at 40 psi for 60 min. The catalyst was removed by filtration of the reaction mixture through a celite pad. The clear filtrate was evaporated to dryness. The product was crystallized from boiling ethanol. Yield was 650 mg of the above-identified product, melting point 188°–189° C.

$^1$H-NMR (D$_2$O) δ ppm, 2.7 (d, 2H, 5'-CH$_2$), 3.8–4.4 (3m, 3H, 2'-CH, 3'-CH and 4'-CH), 5.4 (d, 1H, 1'-CH) and 7.3 (s, 1H, 2-CH). IR (KBr) cm$^{-1}$: 3500–3000 (br. OH, NH$_2$, CONH$_2$, etc.), 1640–1645 (br.s. CONH$_2$).

Example I

Preparation of 5-Amino-1-(2-O-methyl-β-D-ribofuranosyl)-imidazole-4-carboxamide (Compound No. 20 (1-188)) and 5-Amino-1-(3-O-methyl-β-D-ribofuranosyl)imidazole-4-carboxamide (Compound No. 22 (1-243))

5-Amino-1-β-D-ribofuranosylimidazole-4-carboxamide (5.2 g, 20 mmol) was dissolved in 40 ml hot dimethylformamide and diluted with 70 ml methanol containing 35 mg tin(II) chloride dihydrate. A solution of 0.1 mol of diazomethane in 200 ml of ether was added in portions over 45 min. After each addition, 20 mg of tin(II) chloride dihydrate was added. The resulting mixture was filtered and evaporated to give a syrup. The syrup was dissolved in 25 ml of methanol and upon cooling yielded crystalline 5-amino-1-(2-O-methyl-β-D-ribofuranosyl)imidazole-4-carboxamide which was collected by filtration and dried. Yield was 1.2 g, melting point 114°–117° C.

$^1$H NMR (DMSO-d$_6$) (for Compound 20): δ ppm, 3.3 (s, 3H, CH$_3$), 3.6 (m, 2H, 5'-CH$_2$), 3.9 (m, 1H, 4'-CH), 4.1 (m, 1H, 2'-CH), 4.2 (m, 1H, 3'-CH), 5.2 (d, 1H, 3'-OH), 5.3 (t, 1H, 5'-OH), 5.6 (d, 1H, 1'-CH), 6.0 (br. s, 2H, 5-NH$_2$), 6.7 (br. d, 2H, 4-CONH$_2$), 7.3 (s, 1H, 2-CH).

The supernatant from the above crystallization was concentrated and applied to a 200 ml column of silica gel. The column was eluted with 10:1 methylene chloride:methanol (1 L), 8:1 methylene chloride:methanol (500 ml) and 5:1 methylene chloride:methanol (500 ml). The 5:1 eluate contained a major product and was evaporated and residue dissolved in 10 ml of methanol. Upon cooling this yielded crystals which were collected and dried. Yield was 1.4 grams. By NMR decoupling and exchange experiments the product was shown to be 5-amino-1-(3-O-methyl-β-D-ribofuranosyl)imidazole-4-carboxamide.

$^1$H NMR (DMSO-d$_6$) (for Compound 18): δ ppm: 3.3 (s, 3H, CH$_3$), 3.6 (m, 2H, 5'-CH$_2$), 3.7 (m, 1H, 4'-CH), 4.0 (m, 1H, 3'-CH), 4.4 (m, 1H, 2'-CH), 5.3 (t, 1H, 5'-OH), 5.4 (2d, 2H, 2'-CH and 1'-CH), 5.9 (br. s, 2H, 5-NH$_2$), 6.7 (br. d, 2H, CO—NH$_2$), 7.7 (s, 1H, 2-CH).

Example J

Preparation of 5-Amino-1-β-D-ribofuranosyl-imidazole-4-N-|(4-nitrophenyl)methyl|carboxamide (Compound No. 23 (1-343))

N-Succinimidyl-5-amino-1-(2,3,5-tri-O-acetyl-β-D-ribofuranosyl-imidazole-4-carboxylate[3] (0.50 g), 4-nitrobenzylamine hydrochloride (210 mg) and triethylamine (0.16 ml) were stirred in chloroform (30 ml) at room temperature overnight. The solution was washed with saturated sodium bicarbonate solution and water, then evaporated under reduced pressure. The resulting yellow tar was chromatographed on silica gel, eluting with 9:1 methylene chloride:methanol. The collected fractions were monitored by TLC. The like fractions were combined and concentrated under reduced pressure to afford a yellow foam (0.38 g). The foam was dissolved in methanol (20 ml) and methanolic sodium methoxide solution was added (0.3 ml of 0.25M solution). The solution was stirred under an argon atmosphere for 15 min. TLC indicated the reaction was complete. The solution was neutralized to pH 6 with ion exchange resin. The resin was filtered and the solution concentrated under high vacuum to yield a yellow foam (0.23 g).

[3]Srivastava, P. C., *J. Med. Chem.* 17: 1207 (1974).

$^1$H NMR (DMSO-d$_6$) δ ppm, 3.6 (m, 2H, 5'-CH$_2$) 3.9–4.3 (m, 3H, 2'-CH, 3'-CH, 4'-CH), 4.5 (d, 2H, —CH$_2$—C$_6$H$_4$—NO$_2$), 5.2–5.4 (br., 3H, 2'-OH, 3'-OH, 5'-OH), 5.5 (d, 1H, 1'-CH), 6.10 (br. s, 2H, 5-NH$_2$, 7.3 (s, 1H, 2-CH), 7.4–8.2 (AB$_q$, 4H, —C$_6$H$_4$—NO$_2$), 8.3 (t, 1H, 4-CONH).

Example K

Preparation of 5-Amino-1-α-D-ribofuranosylimidazole-4-N-|(3-chlorophenyl)methyl|carboxamide (Compound No. 24 (1-354))

This compound was prepared according to the procedures described in Example J for the 4-p-nitrobenzyl derivative, substituting 2-chlorobenzylamine for 4-nitrobenzylamine hydrochloride.

$^1$H NMR (DMSO-d$_6$) δ ppm, 3.6 (m, 2H, 5'-CH$_2$), 3.9–4.3 (m, 3H, 2'-CH, 3'-CH, 4'-CH), 4.4 (d, 2H, —CH$_2$—O—Cl), 5.1–5.4 (br., 3H, 2'-OH, 3'-OH, 5'-OH), 5.5 (d, 1H, 1'-CH), 6.0 (br.s., 2H, 5-NH$_2$), 7.2–7.4 (m, 4H, —C$_6$H$_4$—Cl), 8.0 (t, 1H, 4-CONH).

Example L

Preparation of 5-amino-1-β-D-ribofuranosylimidazole-4-N-|(2,4-dichlorophenyl)methyl|carboxamide (Compound No. 25 (1-360))

This compound was prepared according to the procedures described in Example J for the 4-p-nitrobenzyl derivative, substituting 2,4-dichlorobenzylamine for 4-nitrobenzylamine hydrochloride.

$^1$H NMR (DMSO-d$_6$), δ ppm, 3.6 (m, 2H, 5'-CH$_2$), 3.9–4.3 (m, 3H, 2'-CH, 3'-CH, 4'-CH), 4.4 (d, 2H, —CH$_2$—C$_6$H$_3$—Cl$_2$), 5.2–5.4 (m, 3H, 2'-OH, 3'-OH, 5'-OH), 5.5 (d, 1H, 1'-CH), 6.0 (br. s, 2H, 5-NH2), 7.2–7.6 (m, 3H —C$_6$H$_3$—Cl$_2$), 8.1 (t, 1H, 4-CONH—).

Example M

Preparation of 5-amino-2-thio-1-β-D-ribofuranosyl imidazole-4-carboxamide (Compound No. 27 (1-395-0))

To 10 ml of 80% formic acid was added 400 mg of 5-amino-2-thio-1-(2,3-O-isopropylidene-β-D ribofuranosyl)-imidazole-4-carboxamide.[4] The resulting mixture was stirred for 1 hour at room temperature. Silica TLC, eluting with 4:1 methylene chloride:methanol, showed conversion of staring material to one major product. The mixture was evaporated to dryness, dissolved in 5 ml of methanol and applied to a 50 ml column of silica gel. The column was eluted with methylene chloride:methanol (5:1). The major product, as determined by TLC, was collected and evaporated to dryness. The residue was dissolved in 3 ml of hot methanol and crystallized upon cooling. Yield was 150 mg of the above-identified product, melting point 205°–208° C.

[4]Preparation described in T. Miyoshi, S. Suzaki, A. Yamazaki, *Chem. Pharm. Bull.*, 24 (9): 2089–2093 (1976).

$^1$H NMR (DMSO-d$_6$), δ ppm 3.6 (m, 2H, 5'-CH$_2$), 3.8 (m, 1H, 4'-CH), 4.1 (m, 1H, 3'-CH), 4.5 (m, 1H, 2'-CH), 5.1 (d, 1H, 2' or 3'-OH), 5.2 (d, 1H, 2' or 3'-OH), 5.7 (t, 1H, 5'-OH), 6.3 (d, 1H, 1'-CH), 6.4 (br. s, 2H, 5-NH$_2$), 6.9 (br. s, 2H, 4-CONH$_2$), 11.1 (br. s, 1H, 5'-SH).

Example N

Preparation of 5-amino-1-(5-chloro-5-deoxy-β-D-ribofuranosyl)imidazole-4-carboxamide (Compound No. 26 (1-332))

AICA riboside (1.00 g), triphenylphosphine (3.05 g) and carbon tetrachloride (1.15 ml) were stirred in dimethyl formamide (38 ml) at room temperature for 3 hours. The solution was diluted with methanol (15 ml), then concentrated under reduced pressure. The resulting yellow tar was chromatographed on silica gel, eluting with 4:1 methylene chloride:methanol. The like fractions were combined and concentrated under reduced pressure to afford a purple foam. The presence of triphenylphosphine oxide, as determined by $^1$H NMR, necessitated a second chromotographic step as above. Yield was 0.43 g of a white foam.

$^1$H NMR (DMSO-d$_6$), δ ppm 3.7–3.9 (m, 2H, 5'-CH$_2$), 4.0–4.4 (m, 3H, 2'-CH, 3'-CH, 4'-CH), 5.4–5.5 (m, 2H, 2'-OH, 3'-OH), 5.6 (d, 1H, 1'-CH), 5.9 (br. s, 2H, 5-NH$_2$), 6.7–6.9 (br. d, 2H, 4-CONH$_2$), 7.3 (s, 1H, 2-CH).

Example O

Preparation of 5-amino-1-(2-O-ethyl-β-D-ribofuranosyl)-4-imidazole carboxamide (Compound No. 34 (1-250)) and 5-amino-1-(3-O-ethyl-β-D-ribofuranosyl)-4-imidazole carboxamide (Compound No. 31 (1-251))

A solution of approximately 30 mmol diazoethane in 40 ml of ether was prepared by slow addition of 7 g (44 mmol) of 1-ethyl-3-nitro-1-nitrosoguanidine to a mixture of 8 g of potassium hydroxide, 9 ml water and 60 ml of ether followed by distillation. This was slowly added to a solution of 3.2 g (12 mmol) of 5-amino-1-β-D-ribofuranosylimidazole-4-carboxamide (AICA riboside) in 35 ml dimethylformamide containing 50 mg of tin(II) chloride dihydrate. During the addition approximately 20 ml of methanol was added to maintain solubility. The reaction was filtered to remove a trace precipitate and evaporated to a yellow syrup. Thin layer chromatography on silica gel using methylene chloride/methanol (3:1) showed a major product spot moving faster than AICA riboside. The syrup was chromatographed on silica gel using methylene chloride/methanol (8:1) collecting the major product as determined by TLC. The appropriate fractions were evaporated to a white foam. This was dissolved in 7 ml of methanol. Upon cooling to 4° C. the mixture crystallized to yield 160 mg of 5-amino-1-(2-O-ethyl-β-D-ribofuranosyl) imidazole-4-carboxamide (Compound No. 34 (1-250)) confirmed by NMR decoupling and exchange experiments.

$^1$H NMR (DMSO-d$_6$) (for Compound No. 34) δ ppm, 1.05 (t, 3H, CH$_3$), 3.3–3.6 (m, 4H, 2'-OCH$_2$—, 5'-CH$_2$), 3.9 (m, 1H, 4'-CH), 4.1–4.3 (m, 2H, 2'-CH, 3'-CH), 5.15 (d, 1H, 3-OH), 5.25 (t, 1H, 5'-OH), 5.55 (d, 1H, 1'-CH), 6.0 (br.s, 2H, 5-NH$_2$), 6.6–6.9 (br.d, 2H, 4-CONH$_2$), 7.3 (S, 1H, 7-CH).

The supernatant from the above crystallization was cooled overnight at –12° C. yielding a second crop of crystals, 0.58 g, which by NMR decoupling and exchange experiments was shown to be mostly 5-amino-1-(3-O-ethyl-β-D-ribofuranosyl) imidazole-4-carboxamide (Compound No. 31 (1-251)).

$^1$H NMR (DMSO-d$_6$) (for Compound No. 31): δ ppm, 1.1 (t, 3H, CH$_3$), 3.4–3.7 (m, 4H 3'-OCH$_2$—, 5'-CH$_2$), 3.85 (m, 1H, 4'-CH), 4.0 (m, 1H, 3'-CH) 4.4 (q, 1H, 2-CH), 5.25 (t, 1H, 5'-OH), 5.35 (d, 1H, 2'-OH), 5.45 (d, 1H, 1'-CH), 5.9 (br.s, 2H, 5-NH$_2$), 6.6–6.9 (br.d, 2H, 4-CONH$_2$), 7.3 (s, 1H, 1-CH). The major impurity was identified as the 2'-O-ethyl isomer.

Example P

Preparation of 5-amino-1-(2-O-n-butyl-β-D-ribofuranosyl)imidazole-4-carboxamide and 5-amino-1-(3-O-n-butyl-β-D-ribofuranosyl) imidazole-4-carboxamide (Compound Nos. 32 (1-262) and 33 (1-263))

5-Amino-1-β-D-ribofuranosylimidazole-4-carboxamide (2.50 g, 10.0 mmol) and tin(II) chloride hydrate (35 mg) were dissolved in dimethylformamide (40 ml) and methanol (30 ml). A solution of 0.1 ml of diazobutane[5] in 150 ml of ether was added in portions. Halfway through the addition, more tin (II) chloride hydrate was added (35 mg). Methanol was added, as needed, to ensure the starting material stayed in solution. The mixture was stirred for 1 hr, then concentrated under reduced pressure to give an oil. Analysis of the oil by $^1$H NMR showed mostly N-butylethylcarbamate. The oil was stirred with hexane and decanted to remove the N-butylethylcarbamate. The resulting tar was chromatographed on silica gel using 6:1 methylene chloride:methanol as eluting solvent. The appropriate fractions were combined and concentrated under reduced pressure to give a pink foam. $^1$H NMR analysis showed a mixture of 2' and 3' butyl ethers. HPLC analysis showed a 56:28 mixture. The solid was dissolved in isopropanol (2 ml) and cooled. The resulting solid was filtered and dried to give 63 mg. HPLC analysis showed a 77/18 mixture. $^1$H NMR decoupling and exchange experiments showed the major product to be the 2'-O-n-butyl ether.

[5] Diazobutane was prepared by treatment of 16.5 g of N-nitroso-N-n-butylmethane [Wilds, A. L. and Meeder, A. L., SOC 13 (1948)] in ethyl ether (100 ml) with potassium hydroxide (55 g) in water (60 ml). The ethereal diazobutane was used without distillation.

$^1$H NMR (DMSO-d$_6$) (for Compound No. 32): δ ppm, 0.8–1.5 (m, 7H, —CH$_2$CH$_2$CH$_3$), 3.3–4.2 (m, 7H, 2'-OCH$_2$—, 2'-CH, 3'-CH, 4'-CH, 5'-CH$_2$), 5.1 (d, 1H, 3'-OH), 5.3 (t, 1H, 5'-OH), 5.6 (d, 1H, 1'-CH), 6.0 (br.s, 2H, 5-NH$_2$), 7.6–7.8 (br.d, 2N, 4-CONH$_2$), 7.3 (s, 1H, 2-CH).

The supernatant from the above crystallization was concentrated under reduced pressure to give 125 mg of a pink foam. HPL analysis showed a 14/71 mixture. $^1$H NMR decoupling and exchange experiments showed the major product to be the 3'-O-n-butyl ether.

$^1$H NMR (DMSO-d$_6$) (for Compound No. 33): δ ppm, 0.8–1.6 (m, 7H, —CH$_2$CH$_2$CH$_3$), 3.4–4.4 (m, 7H, 3'-OCH$_2$—, 2'-CH, 3'-CH, 4'-CH, 5'-CH$_2$), 5.2 (t, 1H, 5'-OH), 5.3 (d, 1H, 2'-OH), 5.4 (d, 1H, 1'-CH), 5.9 (br.s, 2H, 5-NH$_2$), 6.6–6.8 (br.d., 2H, 4-CONH$_2$), 7.3 (s, 1N, 7-CH).

Example O

Preparation of 5-amino-1-β-D-ribofuranosylimidazole-4-N-|(3-nitrophenyl)methyl| carboxamide (Compound No. 28 (1-348))

This compound was prepared according to the procedures described in example J for the 4-p-nitrobenzyl derivative, substituting 3-nitrobenzylamine hydrochloride for 4-nitrobenzylamine hydrochloride.

$^1$H NMR (DMSO-d$_6$) δ ppm, 3.6 (m, 2H, 5'-CH$_2$), 3.9–4.3 (m, 3H, 2'-CH, 3'-CH, 4'-CH), 4.4 (d, 2H, —CH$_2$—NO$_2$), 5.2–5.4 (br., 3H, 2'-OH, 3'-OH, 5'-O), 5.5 (d, 1H, 1'-CH), 6.0 (br.s., 2H, 5-NH$_2$), 7.4 (s, 1H, 7-CH), 7.6–8.2 (m, 4H, —C$_6$H$_4$Cl), 8.3 (t, 1H, 4-CONH).

Example R

Preparation of 5-amino-1-β-D-ribofuranosylimidazole-4-N-|(4-Chlorophenyl) methyl|carboxamide (Compound No. 29 (1-349))

This compound was prepared according to the procedures described in Example J for the 4-p-nitrobenzyl derivative, substituting 4-chlorobenzene amide for 4-nitrobenzylamine hydrochloride.

$^1$H NMR (DMSO-d$_6$) δ ppm, 3.6 (m, 2H, 5'-CH$_2$), 3.9–4.3 (m, 3H, 2'-CH, 3'-CH, 4'-CH), 4.4 (d, 2H, —CH$_2$—C$_6$H$_4$—Cl), 5.2–5.4 (br., 3H, 2'-OH, 3'-OH, 5'-OH), 515 (d, 1H, 1'-CH) 5.9 (br.s., 2H, 5-NH$_2$), 7.3–7.4 (m, 5N, —C$_6$H$_4$C$_1$), 7-CH), 8.1 (t, 1H, 4-CONH).

Example S

Preparation of 5-amino-1-β-D-ribofuranosylimidazole-4-N-|(4-methylphenyl) methyl|carboxamide (Compound No. 30 (1-388))

This compound was prepared according to the procedures described in Example J for the 4-p-nitrobenzyl derivative, substituting 4-methylbenzylamine for 4-nitrobenzylamine hydrochloride.

$^1$H NMR (DMSO-d$_6$) δ ppm, 2.2 (s, 3H, —C$_6$H$_4$—CH$_3$), 3.6 (m, 2H, 5'-CH$_2$), 3.9–4.3 (m, 5H, 2'-CH, 3'-CH, 4'-CH, —CH$_2$— —C$_6$H$_4$—CH$_3$), 5.2–5.4 (br., 3H, 2'-OH, 3'-OH, 5'-OH), 5.5 (d, 1H, 1'-CH), 5.9 (br.s., 2H, 5-NH$_2$, 7.1–7.2 (M, 4H, —C$_6$H$_4$—CH$_3$), 7.3 (s, 1H, 7-CH), 7.9 (t, 1H, 4-CONH).

Example T

Preparation of 5-amino-1-β-D-ribofuranosylimidazole-4-N|(3-chlorophenyl)methyl|carboxamide (Compound No. 35 (1-355))

This compound was prepared according to the procedures described in Example J for the 4-p-nitrobenzyl derivative, substituting 3-chlorobenzylamine for 4-nitrobenzylamine hydrochloride.

$^1$H NMR (DMSO-d$_6$) δ ppm, 3.6 (m, 2H, 5'-CH$_2$), 3.9–4.3 (m, 3H, 2'-CH, 3'-CH, 4'-CH), 4.3 (d, 2H, —CH$_2$—C$_6$H$_4$—Cl), 5.1–5.4 (br., 3H, 2'-OH, 3'-OH, 5'-OH), 5.5 (d, 1H, 1'-CH), 6.0 (br.s., 2H, 5-NH$_2$), 7.2–7.4 (m, 4H, —C$_6$H$_4$—Cl), 7.4(s, 1H, 7-CH), 8.1 (t, 1H, 4-CONH).

Example U

Preparation of 5-amino-4-(1-piperidinocarbamoyl)-1-β-D-ribofuranosylimidazole (Compound No. 36 (1-207))

This compound in Example J for the 4-p-nitrobenzyl derivative, substituting piperidine for 4-nitrobenzylamine hydrochloride. The product was crystallized from ethanol to give the above-identified product, m.p. 190°–192° C.

$^1$H NMR (DMSO-d$_6$) δ ppm, 1.4–1.7 (M, GH, 3, 4, 5-CH$_2$ groups of piperidine ring), 3.55 (m, 2H, 5'-CH$_2$), 3.8–3.95 (m, 5H, 2- and 6-CH$_2$ groups of piperidine ring, and 4'-CH), 4.0–4.1 (m, 1H, 3'-CH), 4.25–4.35 (m, 7H, 2-CH) 5.15 (d, 1H, 2' or 3'-OH), 5.2 (t, 1H, 5'-OH).

Example V

Preparation of 5-Amino-1-β-D-ribofuranosyl-imidazole-4-N-|p-methoxybenzyl|carboxamide (Compound No. 39 (1-390))

A mixture of the activated succinate ester (0.5 g) (prepared according to Example J), 4-methoxybenzylamine (0:15 ml) and methylene chloride (20 ml) was stirred overnight. TLC indicated completion of the reaction. The solvent was evaporated an d the residue was chromatographed over a short silica gel column using a mixture of methylene chloride:methanol (9:1). The fractions containing the product were pooled and evaporated. The residue thus obtained was dissolved in methanol (20 ml) and the pH was adjusted to about 10 by adding a sodium methoxide solution. After stirring the reaction mixture for 45 minutes at room temperature, the solution was neutralized with Dowex 50 H+-resin (pH about 6.0). The resin was filtered off, washed with methanol (2×2 ml). The combined filtrate and the washings was evaporated and the residue was crystallized from ethanol. Yield was 100 mg, with a mp of 187°–188° C.

$^1$H NMR (DMSO-d$_6$): δ ppm, 3.55 (m, 2H, 5'-CH$_2$), 37 (s, 3H, —OCH$_3$), 3.7–4.1 (m, 3H, 2'-CH, 3'-CH, and 4'-CH), 4.35–4.2 (dd, 2H, —CH$_2$—N—), 5.1–5.4 (3,m, 3H, 2'-OH, 3'-OH, and 5'-OH), 5.45(d, 1H, 1-CH), 5.9 (br, 2H, NH$_2$), 6.8–7.2 (m, 4H, aromatic-phenyl), 7.3(s, 17H, C$_2$-H), and 7.85 (t, 1H, C—NH).

Example W

Preparation of 5-Amino-1-β-D-ribofuranosylimidazole-4-N(4-dimethylaminobenzyl)-carboxamide hydrochloride (Compound No. 41 (1-396-3))

To a suspension of 4-dimethylaminobenzylamine hydrochloride (245 mg, 2 mmol) in methylene chloride (25 ml) triethylamine (222 mg, 2 mmol) was added and the resulting mixture stirred 45 minutes to it was added the activatec succinate ester prepared according to example J (500 mg) the resulting mixture was stirred at room temperature over night. TLC indicated completion of the reaction. The reaction mixture was evaporated and the residue was chromato graphed through a short silica gel column using a mixture o methylene chloride-methanol (9:1). Fractions showing th major product were pooled and evaporated to dryness. Th residue was dissolved in methanol (15 ml) and the pH wa adjusted to about 10 using a sodium methoxide solution After stirring at room temperature for 45 minutes, th solution was neutralized with Dowex 50-resin. The resi was filtered off and washed with methanol (2×5 ml). Th combined filtrate and the washings were evaporated t dryness. The residue which was in the form of a foam was dissolved in absolute ethanol (10 ml). The pH of the solution was adjusted to about 5 with an ethanolic-HCl solution. Solvent was evaporated to dryness and the residue was treated with anhydrous ether. The amorphous solid that separated was collected by filtration and washed with ether (2×10 ml), and dried under high vacuum to yield 250 mg. The compound obtained was highly hygroscopic; no melting point could be obtained.

$^1$H NMR (D$_2$O) δ ppm, 3.05 (s, 6H, N(CH$_3$)$_2$), 3.6 (m, 2H, 5'-CH), 3.8–4.3 (3m, 3H, 2'-CH, 3'-CH, and 4'-CH), 4.4 (s, 2H, CH$_2$—N—), 5.5 (d, 1H, 1'-CH), 7.3–7.4 (m, 4H, phenyl), and 7.9 (s, 1H, 2-CH).

Example X

Preparation of (R)-5-Amino-1-β-D-ribofuranosylimidazole-4-N-|2-hydroxy-2-(3,4-dihydroxyphenyl)ethyl|carboxamide (Compound 42 (1-431))

This compound was prepared according to the procedure described in Example J substituting (R)-norepinephrine for 4-nitrobenzylamine hydrochloride and dimethylformamide in place of chloroform as the reaction solvent.

$^1$H NMR (DMSO-d$_6$): δ ppm, 3.1–3.3 (m, 2H, —CH$_2$—N), 3.5–3.6 (m, 2H, 5'-CH$_2$), 3.8–3.9 (m, 1H, 4'-CH) 4.0–4.1 (m, 1H, 3'-CH) 4.2–4.3 (m, 1H, 2'-CH), 4.4–4.5 (m, 1H, phenyl-C$\underline{H}$—OH), 5.2–5.2 (m, 1H, 2' or 3'-OH), 5.2–5.3 (t, 1H, 5'-OH) 5.3–5.4 (m, 1H, 2' or 3'-OH), 5.4–5.5 (d, 1H, 1'-CH), 5.9 (br. s, 2H, 5-NH$_2$), 6.5–6.8 (m, 3H, aryl of catechol), 7.1 (t, 1H, 4-CONH), 7.3 (s, 1H, 2-CH), 7.2–7.8 (br. s, 2H, catechol-OH).

Example Y

Preparation of 5-Amino-2-thiophenyl-1-β-D-ribofuranosylimidazole-4-carboxamide (Compound No. 43 (1-432))

5-Amino-2-bromo-1-(2,3-O-isopropylidene-β-D-ribofuranosyl)imidazole-4-carboxamide$^1$ (1.1 g), thiophenol (1.3 g) and triethylamine (0.61 g) were refluxed in a mixture of 25 ml methanol and 3 ml of 1N sodium hydroxide for 18 hours. The reaction mixture was concentrated and the residue mixed with 40 ml of methylene chloride. The methylene chloride mixture was washed with water and saturated sodium bicarbonate and dried over magnesium sulfate. The methylene chloride was evaporated and the residue purified by chromatography on 200 ml of silica gel using a mixture of methylene chloride and methanol (95:5), yielding 0.5 g of 5-amino-2-thiophenyl-1-(2,3-O-isopropylidene-β-D-ribofuranosyl)imidazole-4-carboxamide. Treatment of that compound with 80% formic acid for 3 hours at room temperature to remove the isopropylidene group followed by evaporation and purification by silica chromatography using methylene chloride:methanol (9:1) yielded 250 mg of the title compound as a white foam.

$^1$Miyosi T., Chem. Pharm. Bull. 24: 2089 (1976).

$^1$H NMR (DMSO-d$_6$) δ ppm, 3.3–3.5 (m, 2H, 5'-CH$_2$), 3.8–3.9 (m, 1H, 4'-CH)4.0–4.1(m, 1H, 3'-CH), 4.5 (q, 1H, 2'-CH) 5.1 (d, 1H, 2'- or 3' -OH), 5.3 (d, 1H, 2'- or 3' -OH), 5.7 (t, 1H, 5'-OH), 5.9 (d, 1H, 1'-CH) 7.5 (br. s, 2H, 4-NH$_2$), 6.7 and 7.1 (br s, 2H, CONH$_2$) 7.1–7.5 (m, 5H, phenyl).

Example Z

Preparation of 5-Amino-1-β-D-ribofuranosylimidazole-4-N-(2-endo-norbornyl) carboxamide) (Compound No. 45 (1-438))

A mixture of (±) endo-2-aminonorbornane hydrochloride (240 mg), triethylamine (160 mg) and methylene chloride was stirred at room temperature for 45 minutes under argon. To it was added activated succinate ester (See Example J) (750 mg) and stirred overnight. TLC indicated completion of the reaction. Solvent was evaporated and the residue chromatographed over silica gel column using a mixture of methylene chloride.methanol (9:1). Fractions containing the product were pooled and evaporated. The residue was dissolved in methanol (25 ml) and the pH was adjusted to about 10 with a sodium methoxide solution. After stirring for 45 minutes at room temperature the solution was neutralized with H+ resin (pH approximately 6). The resin was filtered off and washed with methanol. The combined washings and the filtrate was evaporated and the residue kept under high vacuum to obtain a solid glossy product. Yield was 280 mg.

$^1$H NMR (DMSO-d$_6$) δ ppm, 1.1–2.4 (m, 10H, norbonyl), 3.6 (br.M, 2H, 5'-CH$_2$), 3.9 (m, 1H, —N—CH), 4–4.4 (2 m, 3H, 2'-CH, 3'-CH and 4'-CH), 5.05, and 5.35 (2-d, 2H, 2'-OH and 3'-OH), 5.25 (t, 1H, 5'-OH), 5.5 (d, 1H, 1'-CH), 5.9 (br. 2H, NH$_2$) 6.8 (d, 1H, —NH—CO), 7.25 (S, 1H, 2-CH).

Example AA

Preparation of 5-Amino-1-β-D-ribofuranosyl-imidazole-4-N-|(3-iodophenyl)methyl|carboxamide (Compound No. 44 (1-434))

This compound was prepared according to the procedures described in Example J for the 4-p-nitrobenzyl derivative, substituting 3-iodobenzylamine hydrochloride for 4-nitrobenzylamine hydrochloride.

$^1$H NMR (DMSO-d$_6$) δ ppm, 3.6 (m, 2H, 5'-CH$_2$), 3.9–4.3 (m, 3H, 2'-CH, 3'-CH, 4'-CH), 4.3 (d, 2H, —C$\underline{H}_2$—C$_6$H$_4$—I), 5.2–5.4 (m, 3H, 2'-OH, 3'-OH, 5'-OH), 5.5 (d, 1H, 1'-CH), 5.9 (br.s., 2H, 5-NH$_2$), 7.1–7.7 (m, 4H, —C$_6$H$_4$), 7.3 (s, 1H, 2-CH), 8.1 (t, 1H, 4-CONH—)

Example AB

Preparation of 5-Amino-1-(5-iodo-5-deoxy-β-D-ribofuranosyl)imidazole-4-N-|(4-nitrophenyl) methyl|carboxamide (Compound No. 46(1-44

The compound used in this procedure, 5-amino-1-(5-iodo-5-deoxy-2,3-isopropylidene-β-D-ribofuranosyl) imidazole-4-N-|(4-nitrophenyl)methyl|carboxamide, was prepared by the same reaction sequence (stopping at step B) described in Example AH for compound 53 (1-468), substituting the 4-N-p-nitrobenzylamide (compound 23 (1-343)) for the 4-N-p-chlorobenzylamide (compound 29 (1-349)).

5-Amino-1-(5-iodo-5-deoxy-2,3-O-isopropylidene-β-D-ribofuranosyl)imidazole-4-N-|(4-nitrophenyl)methyl| carboxamide (200 mg) was dissolved in 10 ml of 80% formic acid. The solution was stirred at 45° C. for 2 hours. The solvents were evaporated under reduced pressure and the resulting residue co-evaporated twice with water and twice with methanol. The residue was chromatographed on silica gel, using 6/1 methylene chloride/methanol as eluting solvent. The appropriate fractions were combined and concentrated under reduced pressure to yield 60 mg of the above-identified compound as a yellow foam.

$^1$H NMR (DMSO-d$_6$) δ ppm, 3.3–3.6 (m, 2H, 5'-CH$_2$), 3.8–4.4 (m, 3H, 2'-CH, 3'-CH$_4$'-CH), 4.5 (d, 2H, C$\underline{H}_2$—C$_6$H$_4$NO$_2$), 5.4–5.5 (m, 2H, 2'-OH, 3'-OH), 5.6 (d, 2H, 1'-CH), 5.9 (br.s., 2H, 5-NH$_2$), 7.4 (S, 1H, 2-CH), 7.5–8.2 (m, 4H, C$_6$$\underline{H}_4$—NO$_2$), 8.3(4,1H,4-CONH—).

Example AC

Preparation of 5-Amino-1-β-D-ribofuranosylimidazole-4-carboxylic Acid, p-Nitrobenzylthio Ester (Compound No. 47 (1-450))

5-Amino-1(2,3,5-tri-O-acetyl-β-D-ribofuranosyl) imidazole-4-carboxylic acid$^1$ (1.0 g) was dissolved in 8 ml of thionyl chloride under argon with stirring for 10 minutes. The mixture was evaporated under vacuum and the residue was dissolved in 15 ml of tetrahydrofuran containing 2.0 g of p-nitrobenzyl mercaptan. Triethylamine (1.5 ml) was added and the mixture stirred under argon for 20 minutes. The reaction is evaporated to a gum and the residue mixed with 50 ml of methylene chloride and washed with 2×25 ml of water. The methylene chloride phase was dried over magnesium sulfate and evaporated to a syrup which was purified by chromatography on silica gel using a mixture of ethyl acetate and methylene chloride (1:1) yielding 500 mg of 5-amino-1-(2,3,5-tri-O-acetyl-β-D-ribofuranosyl) imidazole-4-carboxylic acid, p-nitrobenzylthio ester. Treatment with sodium methoxide in 30 ml of dry methanol such that a slightly basic pH was maintained until deacetylation was complete (as determined by thin layer chromatography), followed by neutralization with Dowex 50 (H+) and evaporation yielded the desired compound contaminated with a product presumed to be the methyl ester. Purification by chromatography on silica using a mixture of methylene chloride and methanol (9:1) gave 38 mg of the desired compound as a yellow foam.

[1] Srivastava, P. C., *J. Med. Chem.* 17: 1207 (1974).

$^1$H NMR (DMSO-d$_6$) δ ppm, 3.5–3.7 (m, 2H, 5'-CH$_2$), 3.9–4.0 (m, 1H, 4'-CH), 4.2–4.4 (m, 2H, 2'- and 3'-CH), 5.2 (d, 1H, 2'- or 3'-OH), 5.3–5.5 (m, 2H, 5' and 2'- or 3'-OH), 5.6 (d, 1H, 1'-CH), 6.9 (br. s, 2H, 5-NH$_2$), 7.4 (s, 1 h, 2-CH), 7.6 and 8.2 (d, 2H, phenyl).

Example AD

Preparation of 5-Amino-1-β-D-ribofuranosyl-imidazole-4-N-indolinylcarboxamide (Compound No. 48 (1-452))

This compound was prepared according to the procedures described in Example J for the 4-p-nitrobenzyl derivative, substituting indoline for 4-nitrobenzylamine hydrochloride.

$^1$H NMR (DMSO-d$_6$) δ ppm, 3.1 (t, 2H, indolinyl-CH$_2$), 3.6 (m, 2H, 5'-CH$_2$—), 5.2–5.4 (m, 3H, 2'-OH, 3'-OH, 5'-OH), 5.5 (d, 1H, 1'-CH), 6.4 (br.s., 2H, 5-NH$_2$), 6.9–8.1 (m, 4H, indolinyl aromatics), 7.4 (S, 1H, 2-CH).

Example AE

Preparation of (R)-5-Amino-1-β-D-ribofuranosylimidazole 4-N-|1-4-nitrophenyl)ethyl| carboaxamide (Compound No. 49(1-453))

This compound was prepared according to the procedures described in Example J for the 4-p-nitrobenzyl derivative, substituting (R)-4-nitro-α-methylbenzylamine hydrochloride for 4-nitrobenzylamine hydrochloride.

$^1$H NMR (DMSO-d$_6$) δ ppm, 1.5 (d, 3H, α-methyl on N4-benzyl carboxamide), 3.6 (m, 2H, 5'-CH$_2$), 3.9–4.3 (m, 3H, 2'-CH, 3'-CH, 4'-CH), 5.1 (m, 1H, methine proton on N4-benzylcarboxamide), 5.1–5.4(m, 3H, 2'-OH 3'-OH, 5'-OH), 5.5 (d, 1H, 1'-CH), 7.3 (s, 1H, 2-CH), 7.6–8.2 (m, 4H, C$_6$H$_4$—NO$_2$), 8.0 (d, 1H, 4-CONH—).

Example AF

Preparation of (S)-5-Amino-1-β-D-ribofuranosylimidazole-4-N-|(4-nitrophenyl)ethyl| carboxamide (Compound No. 50(1-459))

This compound was prepared according to the procedures described in Example ) for the 4-p-nitrobenzyl derivative, substituting (S)-4-nitro-α-methylbenzylamine hydrochloride for 4-nitrobenzylamine hydrochloride.

$^1$H NMR (DMSO-d$_6$) δ ppm, 1.5 (d, 3H, α-methyl on N4-benzyl carboxamide), 3.6 (m, 2H, 5-CH$_2$), 3.9–4.3 (m, 3H, 2'-CH, 3'-CH, 4'-CH), 5.1 (m, 1H, methine proton on N4-benzylcarboxamide), 5.1–5.4 (m, 3H, 2'-OH, 3'-OH, 5'-OH), 5.5 (d, 1H, 1'-CH' 5.9 (br.s., 2H, 5-NH$_2$), 7.4 (s, 1H, 2-CH), 7.6–8.2 (m, 4H, C$_6$H$_4$NO$_2$) 8.0 (d, 1H, 4-CONH—).

Example AG

Preparation of 5-Amino-1-(5-chloro-5-deoxy-β-D-ribofuranosyl) imidazole-4-N-|4-nitrophenyl) methylethyl|carboxamide (Compound No. 51(1-466))

5-amino-1-β-D-ribofuranosylimidazole-N-|(4-nitrophenyl)methyl|carboxamide, Compound 23 (1-343) (0.5 g), triphenylphosphine (1.00 g), carbon tetrachloride (0.37 ml), and THF (25 ml) were combined and stirred at ambient temperature,under argon, overnight. A white precipitate formed. Dimethylformamide (8 ml) was added and the solution was stirred at ambient temperature, under argon, overnight. The solvent was evaporated under reduced pressure and the resulting oil co-evaporated with methanol (3×20 ml). The resulting viscous oil was chromatographed on silica gel, using 7:1 methylene chloride:methanol as eluting solvent. The appropriate fractions were combined and concentrated in vacuo to give a yellow foam (0.28 g). The foam was crystallized from cold methanol to give yellow crystals (200 mg), mp=174°–176° C.

$^1$H NMR (DMSO-d$_6$) δ ppm 3.7–3.9 (m, 2H, 5'-CH$_2$), 4.0–4.4 (m, 3H, 2'-CH, 3'-CH, 4'-CH), 4.5 (d, 2H, —CH$_2$—C$_6$H$_4$NO$_2$), 5.4–5.6 (m, 2H, 2'-OH, 3'-OH), 5.6 (d, 1H, 1'-CH), 5.9 (br.s., 2H, 5-NH$_2$), 7.4 (s, 1H, 2-CH), 7.5–8.2 (m, 4H, —C$_6$H$_4$NO$_2$), 8.3 (t,1H, 4-CONH—).

Example AH

Preparation of 5-Amino-1-(5-azido-5-deoxy-β-D-ribofuranosyl)imidazole-4-N-|(4-chlorophenyl) methyl|carboxamide (compound 52 (1-467)) and 5-Amino-1-(5-amino-5-deoxy-β-D-ribofuranosyl) imidazole-4-N-|(4-chlorophenyl)methyl| carboxamide Hydrochloride (Compound No. 53 (1-468))

A. Preparation of 5-Amino-1-(2,3-O-isopropylidene-β-D-ribofuranosyl)imidazole-4-N-|(4-chlorophenyl)methyl| carboxamide Compound 29 (1-349), (6.8 g, 17.8 mmole), was dissolved in a mixture of 100 ml DMF, 15 ml acetone and 15 ml 2,2-dimethoxypropane. Hydrogen chloride gas (approximately 1.0 g) was added and the mixture stirred under argon for 4 hours. The mixture was poured into 50 ml of saturated sodium bicarbonate and evaporated under vacuum at 45° C. The residue dissolved in a mixture of 100 ml ethyl acetate and 25 ml water. The ethyl acetate phase was separated and washed with 25 ml of water, dried over magnesium sulfate and concentrated to a foam. TLC (silica gel, 9:1 methylene chloride:methanol)showed a significant faster moving impurity in the product which was identified as the 5'-(2-methoxypropane) mixed ketal of the above-identified compound. This was converted to the above-identified compound by dissolving the foam in 100 ml of methanol and adjusting the pH to 2.5 with ethanolic hydrogen chloride. After 30 minutes the mixture was neutralized with saturated sodium bicarbonate and concentrated to a slurry. This was dissolved in 100 ml of methylene chloride, washed with 25 ml of water. The methylene chloride phase was dried over magnesium sulfate and concentrated to a foam. Drying under vacuum at 40° C. for 18 hours yielded 7.2 g (96%) of the above-identified compound.

B. Preparation of 5-Amino-1-(5-iodo-5-deoxy-2,3-isopropylidene-β-D-ribofuranosyl)imidazole-4-N-|(4-chlorophenyl)methyl|carboxamide A mixture of the product of Step A (25 g, 59 mmole) and methyltriphenoxyphosphonium iodide (76 g, 166 mmole) in 500 ml of methylene chloride was stirred for 30 minutes at room temperature under argon. The resulting solution was extracted with 150 ml of water, 150 ml of 5% sodium thiosulfate, 150 ml of 1N sodium hydroxide, 100 ml of water and dried over magnesium sulfate. The solvent was removed under vacuum and the resulting oil applied to a 1.31 column of flash grade silica gel prepared in 2:1 hexane:ethyl actetate. The column was eluted with the same solvent to remove impurities then 1:1 hexane:ethyl acetate was used to elute the desired product. Appropriate fractions were combined and evaporated to yield 24.4 g of the above-identified compound as a gummy solid. Impure fractions were again subjected to chromatography to yield an additional 2.3 g of the above-identified product. Total yield was 26.7 g (85%).

C. Preparation of 5-amino-1-(5-azido-5-deoxy-2,3-O-isopropylidene-β-D-ribofuranosyl)imidazole-4-N-[(4-chlorophenyl)methyl]carboxamide A mixture of the product of Step B (26.7 g, 50 mmole), lithium azide (14 g, 285 mmole) and 100 mg of 18-crown-6 in 350 ml of DMF was stirred for 8 hours at room temperature under argon. The slurry was concentrated to remove solvent and the residue dissolved in a mixture of 500 ml of ethyl acetate and 100 ml of water. The ethyl acetate phase was separated, washed with water and saturated sodium chloride, and then dried over magnesium sulfate. Evaporation of the solvent yielded 25 g of the above-identified compound as a yellow gum which still contained solvent. This was used in the next step without further purification.

D. Preparation of 5-Amino-1-(5-azido-5-deoxy-β-D-ribofuranosyl)imidazole-4-N-|(4-chlorophenyl)methyl| carboxamide. (Compound No. 52 (1-467))

The product of Step C, as obtained, was dissolved in 150 ml of 80% trifluoracetic acid and warmed to 50° C. for 30 minutes. The solution was evaporated to a syrup at 40° C. under vacuum and the residue evaporated twice from 25 ml of water. The syrupy residue was dissolved in 100 ml of ethyl acetate and gently stirred over 100 ml of saturated sodium bicarbonate. Crystallization began in the ethyl acetate phase and after 1 hour crystals were collected by filtration. These crystals were combined with two additional crops or crystals obtained by concentration of the ethyl acetate phase to yield 15.7 g (77% yield based on the product of Step B). Melting point of an analytical sample was 182°–183° C.

$^1$H NMR (DMSO-d$_6$) δ ppm, 3.6 (M, 2H, 5'-CH$_2$), 4.0–4.3 (m, 3H, 2'-CH, 3'-CH, 4'-CH), 4.3 (d, 2H, —CH$_2$C$_6$H$_4$C$_1$), 5.4–5.5 (m, 2H, 2'-OH, 3'-OH), 5.5 (d, 1H, 1'-CH), 5.9 (br.s., 2H, 5-NH$_2$), 7.3–7.4 (m, 4H, C$_6$H$_4$Cl), 7.4 (s, 1H, 2-CH), 8.1 (t, 1H, 4-CONH—), IR (KBr) cm$^{-1}$, 2110.

E. Preparation of 5-Amino-1-(5-amino-5-deoxy-β-D-ribofuranosyl)imidazole-4-N-|(4-chlorophenyl)methyl| carboxamide Compound 52 (1-467) (6.5 g, 159 mmole) was dissolved in 500 ml of boiling ethanol. After cooling to 40° C. the solution was saturated with argon and 0.5 g of 10% palladium on carbon added. The mixture was stirred under a hydrogen atmosphere for 8 hours. The mixture was saturated with argon and filtered through Celite 505 and concentrated to a syrup which was used in the next step without further purification.

F. Preparation of 5-Amino-1-(5-amino-5-deoxy-β-D-ribofuranosyl)imidazole-4-N-|(4-chlorophenyl)methyl| carboxamide Hydrochloride (Compound No. 53 (1-468))

The product of Step E (theoretically 159 mmole) was dissolved in 100 ml of ethanol and 3.5 ml of 6N hydrochloric acid added (pH to wet pH paper approximately 3). The solution was evaporated to a hard syrup. This syrup was dissolved in 50 ml of hot ethanol and diluted with 150 ml of ethyl ether. The resulting gummy precipitate was stirred sealed for 12 hours and the resulting white precipitate collected by filtration and washed with ether. Drying under vacuum at 40° C. yielded 6.0 g of the above-identified compound (90% yield based on the compound from Step D).

$^1$H NMR (DMSO d$_6$) δ ppm, 3.0–3.2 (m, 2H, 5'-CH$_2$), 4.0–4.4 (M, 3H, 2'-CH, 3'-CH, 4'-CH), 4.4 (d, 2H, —CH$_2$—C$_6$H$_4$Cl), 5.8–6.2 (br., 2H, 2'-OH, 3'-OH), 7.2–7.4 (m, 4H, C$_6$H$_4$Cl), 7.8 (s, 1H, 2-CH), 8.3 (br., 3H, NH$_2$.HCl).

Example AI

Preparation of 5-Amino-1-(5-amino-5-deoxy-β-D-ribofuranosyl)imidazole-4-N-(cyclopentyl) carboxamide Hydrochloride ((Compound No. 37) 1-270))

This compound was prepared by the same reaction sequence described in Example AH for compound 53 (1-468), substituting the 4-N-cyclopentylamide, compound 10 (1-186), of Table XII for the 4-N-p-chlorobenzylamide compound 29 (1-349) of Table XII.

$^1$H NMR(DMSO-d$_6$) δ ppm, 1.4–1.9(m, 9H, cyclopentyl aliphatic protons), 3.0–3.2 (m, 2H, 5'-CH$_2$), 4.0–4.3(m, 3H, 2'-CH, 3'-CH, 4'-CH), 5.5(d, 1H, 1'-CH), 5.9(br.s, 2H, 5-NH$_2$), 7.1(d, 1H, 4-CONH—), 7.4(s, 1H, 2-CH).

Example AJ

Preparation of 5-Amino-1-(5-deoxy-5-methylthio-β-D-ribofuranosyl)imidazole-4-carboxamide (Compound No. 54 (1-483))

The intermediate, 5-amino-1-(5-chloro-5-deoxy-β-D-ribofuranosyl)imidazole-4-carboxamide, was prepared according to the procedures described in Example AI for compound 5$^1$(1-466), substituting 5-amino-1-β-D-ribofuranosylimidazole-4-carboxamide for 5-amino-1-β-D-ribofuranosylimidazole-4-N-|(4-nitrophenylmethyl| carboxamide.

To a 0.1N sodium methoxide/methanol solution, at 0° under argon, was bubbled methyl mercaptan. To the resulting 0.1 N sodium methylthiolate/methanol solution was added 5-amino-1-(5-chloro-5-deoxy-β-D-ribofuranosyl) imidazole-4-carboxamide (0.40 g). The solution was heated of reflux overnight. The solution was cooled and neutralized with Dowex 50 strongly acidic ion exchange resin. The mixture was filtered and concentrated under reduced pressure. The resulting residue was chromatographed on silica gel, using 4:1 methylene chloride:methanol as the eluting solvent. The appropriate fractions were combined, concentrated under reduced pressure, and vacuum dried to give the above-identified compound as a white foam (0.28 g).

$^1$H NMR (DMSO-d$_6$) δ ppm, 2.1(s, 3H, —S—CH$_3$), 3.7–3.9(m, 2H, 5'-CH$_2$), 3.9–4.4(m, 3H, 2'-CH, 3'-CH, 4'-CH), 5.3–5.4 (m, 2H, 2'-OH, 3'-OH), 5.5(d, 1H, 1'-CH), 5.8(br.s., 2H, 5-NH$_2$), 6.6–6.9(br.m, 2H, 4-CONH$_2$), 7.3(s, 1H, 2-CH).

Example AK

Preparation 5-Amino-1-β-D-ribofuranosylimidazole-4-N-(4-bromophenyl)carboxamide (Compound No. 55 (1-484))

5-Amino-1-(2,3,5-tri-O-acetyl-β-D-ribofuranosyl) imidazole-4-carboxylic acid (Srivastava, P. C., et al., J. Med.

Chem. 17 1207. (1974). (0.75 g) and thionyl chloride (7 ml) were stirred at ambient temperature under a drying tube. for 15 minutes. The excess thionyl chloride was evaporated under reduced pressure and the resulting residue co-evaporated with methylene chloride (3×20 ml). The resulting yellow foam was dissolved in methylene chloride (40 ml) and 4-bromoaniline (0.35 g) was added. Triethylamine (approximately 0.75 ml) was added until the solution was basic. The solution was stirred at ambient temperature under a drying tube for 2 hours. The solution was washed with water. dried with magnesium sulfate. and concentrated under reduced pressure to give a yellow foam. The foam was dissolved in methanol (35 ml). A sodium methoxide methanol solution (approximately 0.75 ml of a 0.5N solution) was added and the resulting solution stirred at ambient temperature under a drying tube. for 30 minutes. The solution was neutralized with methanol-washed Dowex 50 (strongly acidic ion-exchange resin). The mixture was filtered and concentrated under reduced pressure to give a pale yellow residue. The residue was crystallized from methanol (15 ml)/methylene chloride (10 ml) to give tan crystals (0.23 g). The crystals were recrystallized to give off-white crystals (90 mg). Mp: 214°–216° C. (decomp).

$^1$H NMR (DMSO-d$_6$) δ ppm. 3.6(m. 2H. 5'-CH$_2$). 3.9–4.3 (m. 3H. 1'-CH. 3'-CH. 4'-CH). 5.2–5.4(m. 3H. 2'-OH. 3'-OH. 5'-OH). 5.5(d. 1H. 1'-CH). 6.2(br.s.. 2H. 5-NH$_2$). 7.4–7.8 (m. 4H. —C$_6$H$_4$Br). 7.4(s. 1H. 2-CH). 9.5(s. 7H. 4-CONH).

Example AL

Preparation of 5-Amino-1-β-D-ribofuranosyl-imidazole-4-N-|(4-bromophenyl)methyl| carboxamide (Compound No. 56 (1-487))

This compound was prepared according to the procedures described in Example J for the 4-p-nitrobenzyl derivative. substituting 4-bromobenzylamine hydrochloride for 4-nitrobenzylamine hydrochloride.

$^1$H NMR(DMSO-d$_6$) δ ppm. 3.5–3.6(m. 2H. 5'-CH$_2$). 3.9–4.3(m. 3H. 2'-CH. 3'-CH. 4'-CH). 4.3 (d. 2H. C H$_2$—C$_6$H$_4$Br). 5.1–5.4 (m. 3H. 2'-OH. 3'-OH. 5'-OH). 5.5 (d. 1H. 1'-CH). 5.9(br.s. 2H. 5-NH$_2$). 7.2–7.5(m. 4H. —C$_6$H$_4$Br). 7.3(s. 4H. 2-CH). 8.0(t. 1H. 4-CONH—).

Example AM

Preparation of 5-Amino -1-β-D-ribofuranosyl-imidazole-4-N-(4-iodophenyl) carboxamide (Compound No. 57 (1-488))

This compound was prepared according to the procedures described in Example AK for the 4-p-bromophenyl derivative. substituting 4-iodoaniline for 4-bromoaniline. The final product was recrystallized from ethanol. Mp: 227°–229° C. H NMR (DMSO-d$_6$) δ ppm. 3.5–3.6(m. 2H. 5'-CH$_2$). 3.9–4.4(m. 3H. 2'-CH. 3'-CH. 4'-CH). 5.2–5.4 (m. 3H. 2'-OH. 3'-OH. 5'-OH). 5.5(d. 1H. 1'-CH). 6.2(br.s.. 2H. 5-NH$_2$). 7.4(s. 1H. 2-CH). 7.6–7.7(m. 4H. —C$_6$H$_4$I). 9.5(s. 1H. 4-CONH).

Example AN

Preparation of 5-Amino-1-β-D-ribofuranosylimidazole-4-N-(4-nitrophenyl) carboxamide (Compound No. 58 (1-489))

This compound was prepared according to the procedures described in Example AK for the 4-p-bromophenyl derivative. substituting 4-nitroaniline for 4-bromoaniline.

The final product was recrystallized from methanol to give a yellow powder.

$^1$H NMR (DMSO-d$_6$) δ ppm. 3.5–3.6(m. 2H. 5'-CH$_2$). 3.9–4.4(m. 3H. 2'-CH. 3'-CH. 4'-CH). 5.2–5.4 (m. 3H. 2'-OH. 3'-OH. 5'-OH). 5.6(d. 1H. 1'-CH). 6.4(br.s.. 2H. 5-NH$_2$). 7.5(s. 1H. 2-CH). 8.1–8.3 (m. 4H. C$_6$H$_4$NO$_2$). 10.1(s. 1H. 4-CONH).

Example AO

Preparation of 5-Amino-1-β-D-ribofuranosyl-imidazole-4-N-|2-(4-nitrophenyl)ethyl carboxamide (Compound No. 59 (1-506))

This compound was prepared according to the procedures described in Example J for the 4-p-nitrobenzyl derivative. substituting 4-nitrophenethylamine hydrochloride for 4-nitrobenzylamine hydrochloride.

$^1$H NMR (DMSO-d$_6$) δ ppm. 2.9–3.0(t. 2H. —CH$_2$—C$_2$H$_4$—NO$_2$). 3.4–3.6 (m. 2H. 5'-CH$_2$). 3.9–4.3 (m. 3H. 2'-CH. 3'-CH. 4'-CH). 4.8–5.4(br.. 3H. 2'-OH. 3'-OH. 5'-OH). 5.5(d. 1H. 1'-CH). 5.9– 6.2(br.. 2H. 5-NH$_2$). 7.5–8.2 (m. 4H. —C$_6$H$_4$NO$_2$). 7.6(s. 1H. 2-CH). 7.7(t. 1H. 4-CONH).

Example AP

Preparation of 5-Amino-4-|1-|4-(4-nitrophenyl)| piperazinocarbamoyl|-1-β-D-ribofuranosylimidazole (Compound No. 60 (1-508))

This compound was prepared according to the procedures described in Example J for the 4-nitrobenzyl derivative. but substituting 1-(4-nitrophenyl)piperazine for 4-nitrobenzylamine hydrochloride. The product as recrystallized from cold methanol and had a mp of 199°–200° C.

$^1$H NMR (DMSO-d$_6$) δ ppm. 3.4–3.6(m. 10H. 3'-CH$_2$. piperazonyl methylenes). 3.9–4.3(m. 3H. 2'-CH. 3'-CH. 4'-CH). 5.2–5.4(m. 3H. 2'-OH. 3'-OH. 5'-OH). 5.5(d. 1H. 1'-CH). 6.3 (br.s.. 2H. 5-NH$_2$). 7.0–8.1(m. 4H. —C$_6$H$_4$NO$_2$). 7.3(s. 1H. 2-CH).

Example AQ

Preparation of 5-Amino-1-(5-deoxy-β-D-ribofuranosyl)imidazole-4N-|(4-chlorophenyl) methyl|carboxamide (Compound No. 61 (1-509))

5-Amino-1-(5-iodo-5-deoxy-2,3-isopropylidene-β-D-ribofuranosyl)imidazole-4-N-|(4-chlorophenyl)methyl carboxamide (see procedures described in Example AH foi preparation of Compound 53 (1-468). step B) (0.64 g) wa: stirred in 30 ml of 50% formic acid overnight. The exces: solvent was evaporated under reduced pressure. The result ing residue was co-evaporated with water (25 ml) an( methanol (25 ml). The resulting yellow foam was chromato graphed on silica gel. using 9:1 methylene chloride:metha nol as eluting solvent. The appropriate fractions were com bined and concentrated under reduced pressure to give 0.4˙ g of 5-amino-1-(5-iodo-5-deoxy-β-D-ribofuranosyl imidazole-4-N-|(4-chlorophenyl)methyl| carboxamide.

5-Amino-1-(5-iodo-5-deoxy-β-O-ribofuranosyl imidazole-4-N-|(4-chlorophenyl)methyl| carboxamid, (0.04 g). palladium on carbon 10% (20 mg). and ethanol (2( ml) were charged to a Parr bottle. The bottle and content were charged with 45 p.s.i. hydrogen. The reaction progres was monitored by HPLC (Waters C18. 55% methanol/45% 0.1N acetic acid. 260 nm. 1.0 ml/min). After 24 hour. ther was 34% starting material. Fresh catalyst was added (20 mg) and the mixture re-charged with hydrogen (45 p.s.i.). The mixture was shaken for an additional 48 hours. The reaction mixture contained 30% starting material. The mixture was filtered through Celite, and concentrated under reduced pressure. The resulting residue was chromatographed on silica gel, using ethyl acetate (400 ml) and 5% methanol in ethyl acetate (200 ml) as the eluting solvent. The appropriate fractions were combined and concentrated under reduced pressure to yield 70 mg of a white foam. HPLC indicated 9% starting material. The material was rechromatographed on silica gel, using ethyl acetate as eluting solvent. All fractions containing less than 3% starting material were combined and concentrated under reduced pressure to yield 36 mg of the above-identified compound as a pink foam.

$^1$H NMR (DMSO-d$_6$) δ ppm. 1.2–1.3(d, 3H, 5'-CH$_3$), 3.7–4.3(m, 3H, 2'-CH, 3'-CH$_2$ 4'-CH), 4.3(d, 2H, C H$_2$—C$_6$H$_4$Cl), 5.1–5.4(m, 3H, 2'-OH, 3'-OH, 1'-CH), 5.8 (br.s., 2H, 5-NH$_2$), 7.2–7.4(m, 5H, C$_6$H$_4$Cl, 2-CH), 8.1(t, 1H, 4-CONH).

Example AR

Preparation of 5-Amino-1-(5-deoxy-5-methylsulfinyl-β-D-ribofuranosyl)imidazole-4-carboxyamide (Compound No. 62 (1-510))

5-Amino-1-(5-deoxy-5-methylthio-β-D-ribofuranosyl) imidazole-4-carboxamide (compound 54 (1-483)) of Example AK (0.40 g) was dissolved in water (20 ml). Hydrogen peroxide, 30 weight percent, (0.42 ml), was added and the solution stirred for 30 minutes. TLC (6/1, methylene chloride/methanol) indicated some starting material present. An additional 1.0 ml of hydrogen peroxide was added and the solution stirred for 15 minutes. TLC indicated no starting material. The solvent was evaporated under reduced pressure to give a yellow foam. The foam was chromatographed on silica gel, using 3/1, methylene chloride/methanol, as eluting solvent. The appropriate fractions were combined and concentrated in vacuo to give 75 mg of the above-identified compound as a yellow foam.

HPLC (Waters C18, 100% 0.1N acetic acid, 1.0 ml/minutes, 260 nm) indicated 2 equimolar products. This is consistent with oxidation of the product to a diaster omeric mixture of sulfoxides.

$^1$H NMR (DMSO-d$_6$) δ ppm. 2.6(s, 3H, CH$_3$S(O)—), 3.0–3.2 (m, 2H, 5'-CH$_2$), 4.0–4.4(m, 3H, 2'-CH, 3'-CH, 4'-CH) 5.4–5.6(m, 3H, 2'-OH, 3'-OH, 1'-CH), 5.9(br.s., 2H, 5-NH$_2$), 6.6–6.9 (br., 2H, 4-CONH$_6$), 7.3(s, 1H, 2-CH).

Example AS

Preparation of 5-Amino-1-β-D-(5-deoxy-5-methylaminoribofuranosyl)imidazole-4-carboxamide (Compound No. 63 (1-517)

5'-Deoxy-5'-iodo-2',3'-O-isopropylidene-AICA riboside (1.00 g) (ref: P. C. Srivastava, A. R. Newman, T. R. Mathews, and T. R. Mathews, and R. K. Robins, J. Med. Chem., 18, 1237 (1975)), methylamine 40% weight in water (3 ml), and methanol (30 ml) were combined and heated at reflux for 18 hours. The reaction gave a mixture of products. The solution was cooled and the solvents evaporated under reduced pressure. The resulting residue was chromatographed on silica gel, using 6/1 methylene chloride/methanol (400 ml) and 3/1 methylene chloride/methanol (300 ml) as the eluting solvent. The fractions containing the slow-eluting component which was desired product were combined and evaporated under reduced pressure to give 0.13 g of 5'-deoxy-5'-methylamino-2',3'-isopropylidene-AICA riboside.

5'-deoxy-5'-methylamine-2',3'-isopropylidene AICA riboside (0.13 g) was heated at 60° C. in 75% formic acid (20 ml) for 1.5 hour. The solution was cooled and the solvent evaporated under reduced pressure to yield a white foam. The foam was dissolved in water (5 ml) and applied to a short column of Dowex 50 strongly acidic ion-exchange resin. The column was washed with water then eluted with 1M NH$_4$OH in 20% methanol/water. The solvent was evaporated under reduced pressure and the resulting residue co-evaporated with methanol (3×20 ml) to yield 75 mg of the above-identified product as an off-white foam.

$^1$H NMR (D$_6$-DMSO-d$_6$) δ ppm. 2.3 (s, 3H, CH$_3$N), 2.5–2.7 (m, 2H, 5'-CH$_2$), 3.3–3.4(br., 1H, MENH), 3.9–4.3 (m, 3H, 2'-CH, 3'-CH, 4'-CH), 5.1–5.4(m, 2H, 2'-OH, 3'-OH), 5.4(d, 1H, 1'-CH), 6.2(br.s., 2H, 5-NH$_2$), 6.6–6.8 (br., 2H, 4-CONH), 7.2(s, 1H, 2-CH).

Example AT

Preparation of 5-Amino-1-β-D-ribofuranosylimidazole-4-N-(2-chlorophenyl) carboxamide (Compound No. 64 (1-519))

This compound was prepared according to the procedures described in Examples AK for compound 55 (1-484) for the 4-p-bromophenyl derivative, substituting 2-chloroaniline for 4-bromaniline. The final product was recrystallized from methylene chloride (20 ml)/methanol (1 ml) to yield 0.25 g of the above-identified product. Mp=131°–135° C.

$^1$H NMR (DMSO-d$_6$) δ ppm. 3.5–3.6(m, 2H, 5'-CH$_2$), 3.9–4.3(m, 3H, 2'-CH, 3'-CH, 4'-CH), 5.2–5.4(m, 3H, 2'-OH, 3'-OH, 5'-OH), 5.5(d, 1H, 1'-CH), 6.2(br.s., 2H, 5-NH$_2$), 7.0–8.4 (m, 5H, C$_6$H$_4$Br, 2'-CH), 9.1(s, 1H, 4-CONH).

Example AU

Preparation of 5-Amino-1-β-D-(5-benzylamino-5-deoxyribofuranosyl)imidazole-4-carboxamide (Compound No. 66(1-531))

5'-deoxy-5'-iodo-2',3'-isopropylidene AICA riboside (1.00 g) (ref: P. C. Srivastava, A. R. Newman, T. R. Mathews, and R. K. Robins, J. Med. Chem. 18: 1237 (1975)), benzylamine (2.0 ml), and methanol (40 ml) were combined and heated at reflux for 24 hours. Then, the procedures described in Example AS for Compound 63 (1-517) were followed to give the above-identified compound.

$^1$H NMR (DMSO-d$_6$) δ ppm. 2.7 (d, 2H, —CH$_2$—C$_6$H$_5$), 3.3–3.4(br., 1H, —NH —CH$_2$C$_6$H$_5$), 3.9–4.3(m, 3H, 2'-CH, 3'-CH, 4'-CH), 5.1–5.4(m, 2H, 2'-OH, 3'-OH), 5.4(d, 1H, 1'-CH), 6.1(br.s., 2H, 5-NH$_2$), 6.6–6.8(br., 2H, 4-CONH$_2$), 7.2–7.4(m, 6H, —C$_6$H$_5$, 2-CH).

Example AV

Preparation of 5-Amino-2-thio-1-β-D-(5-deoxyribofuranosyl)imidazole-4-carboxamide (Compound No. 67 (1-535))

A. Preparation of 5'-Deoxy-2',3'-isopropylidene-2-bromo-AICA Riboside

To a solution of 5'-deoxy-2',3'-isopropylidene-AICA riboside (2.90 g) (ref: P. C. Srivastava, A. R. Newman, T. R. Mathews, and R. K. Robins, J. Med. Chem., 18: 1237

(1975)) in chloroform (100 ml), was added N-bromosuccinimide in small portions over 20 minutes. The solution was stirred at ambient temperature for 30 minutes. The solution was washed with water, twice with brine, and then dried over magnesium sulfate. The solvent was evaporated in vacuo to yield a dark foam. The foam was passed through a column of silca gel, eluting with 9:1 methylene chloride:methanol. The fractions containing product were combined and concentrated under reduced pressure to yield 2.02 g of reddish-brown foam.

B. Preparation of 5'-Deoxy-2-−3'-O-isopropylidene-2-thio AICA Riboside

Potassium sulfate (3.7 g) was heated at reflux in ethanol (20 ml) for 15 minutes. The mixture was filtered. To the filtrate was added 5'-deoxy-2',3'-isopropylidene-2-bromo AICA riboside (from step A). The mixture was heated at 100° C. in a steel bomb for 5.5 hours. The mixture was cooled and filtered. The pH of the filtrate was adjusted to about 5–6 with acetic acid, and the solvent evaporated under reduced pressure. The resulting residue was passed through a column of silica gel, eluting with 7/1, methylene chloride/methanol. The fractions containing the product were combined and concentrated under reduced pressure to give a dark brown foam. The foam was stirred in methylene chloride (50 ml), then filtered to yield a pale purple powder. The powder was stirred in cold methanol, then filtered and vacuum dried to yield 0.52 g of a pale yellow solid. Mp=211–214 (decomposition).

C. Preparation of 5-Amino-2-thio-1-(deoxy-β-D-ribofuranosyl)imidazole-4-carboxamide (Compound 67 (1-535))

5'-deoxy-2',3'-isopropylidene-2-thiol AICA riboside (0.45 g) (from step B) was stirred in 50% formic acid (30 ml) at 50° C. for 1 hour. The solvent was evaporated under reduced pressure. The resulting residue was co-evaporated with methanol (2×20 ml). The resulting solid was warmed in methanol (25 ml), then stirred at room temperature overnight. The mixture was filtered and the filtrate concentrated under reduced pressure to yield a greenish foam. The foam was chromatographed on silica gel, using 5/1, methylene chloride/methanol, as the eluting solvent. The appropriate fractions were combined and concentrated under reduced pressure to give a yellow foam. The foam was crystallized from cold methanol to yield 69 mg. of the above-identified compound mp=201°–203° C., (decomposition).

$^1$H NMR (DMSO-d$_6$) δ ppm 1.3(d, 3H, 5'-CH$_3$), 3.6–4.5 (m, 3H, 2'-CH, 3'-CH, 4'-CH), 5.0–5.2 (m, 2H, 2'-OH, 3'-OH), 5.6(br.s., 2H, 5-NH$_2$), 6.0(d, 1H, 1'-CH), 7.0(br., 2H, 4-CONH), 12.0 (br.s., 1H, —SH).

Example AW

Preparation of N,N'-bis-(5-amino-1-β-D-ribofuranosyl imidazole-4-carbonyl)-1,6-diaminohexane (Compound No. 68 (1-538))

N-succinimidyl-5-amino-1-(2,3,5-tri-O-acetyl-β-D-ribofuranosyl-imidazole-4-carboxylate (2.50 g) (ref: Srivastava, P. C., et al., J. Med. Chem. 17: 1207 (1974)), 1,6-hexane diamine (0.300 g), triethylamine (0.5 ml), and methylene chloride (35 ml) were combined and stirred at room temperature for 18 hours. The title compound was prepared according to the procedures described in Example J. The final product was crystallized from methanol to yield 0.32 g of the above-identified compound. Mp −181°–185° C.

$^1$H NMR data reported as for half the symmetrical dimer.
$^1$H NMR (DMSO-d$_6$) δ ppm. 1.2–1.5(m, 4H, β and δ methylenes of N-hexyldicarboxamide), 3.0–3.2(m, 2H, α methylene of N-hexyl dicarboxamide), 3.5–3.6(m, 2H, 5'-CH$_2$), 3.8–4.3(m, 3H, 2'-H, 3'-CH, 4'-CH), 5.1–5.4(m, 3H, 2'-OH, 3'-OH, 5'-OH), 5.5(d, 1H, 1'-CH), 5.9(br.s., 2H, 5-NH$_2$), 7.3(s, 1H, 2-Ch), 7.4 (t, 1H, 4-CONH).

Example AX

Preparation of N,N'-Bis-(5-Amino-1-β-D-ribofuranosylimidazole-4-carbonyl)-1,4-diaminocyclohexane (Compound No. 69 (1-549))

This compound was prepared according to the procedures described in Example AW for compound 68 (1-538), substituting 1,4-diaminocyclohexane for 1,6-hexanediamine.

$^1$H NMR data are reported as for half the symmetrical dimer. $^1$H NMR (DMSO-d$_6$) δ ppm 1.3–1.8(m, 4H, cyclohexane methylene protons), 3.5–3.7(m, 3H, 5'-CH$_2$, cyclohexane methine), 3.8–4.3(m, 3H, 2'-CH, 3'-CH, 4'-CH), 5.1–5.4(m, 3H, 2'-OH, 3'-OH, 5'-OH), 5.5(d, 1H, 1'-CH), 5.9(br.s., 2H, 5-NH$_2$), 7.1(d, 1H, 4-CONH) 7.3(s, 1H, 2-CH).

Example AY

Preparation of 5-Amino-2-thio-1-(5-amino-5-deoxy-β-D-ribofuranosyl)imidazole-4-carboxamide
(Compound No. 70(1-551))

A. Preparation of 5-Deoxy-5'-iodo-2-bromo-2', 3'-isopropylidene AICA Riboside

2-Bromo-2'3'-isopropylidene AICA riboside (4.50 g) (ref: T. Miyoshi, S. Suzaki, A. Yamazaki, Chem. Pharm. Bull. 29, 9: 2089, (1976) methyltriphenoxyphosphonium iodide (16.2 g), and methylene chloride (125 ml) were combined and stirred at room temperature for 16 hours. The mixture was washed with water, 0.5M NAOH (100 ml), 5% NaS$_2$O$_3$ (150 ml), and brine, then dried over magnesium sulfate. The solvent was evaporated under reduced pressure to give an orange oil. The oil was triturated in cold diethylether. The resulting mixture was filtered to give 3.53 g of a grey powder. The mother liquor was concentrated under reduced pressure to give an orange oil. The oil was applied to a short column of silica gel. The column was washed with methylene chloride, then the product eluted with 9/1, methylene chloride/methanol (250 ml). The appropriate fractions were combined and concentrated under reduced pressure to give an orange tar. The tar was triturated with cold diethyl ether. The mixture was filtered to yield an additional 0.94 g of a gray powder. The combined powder (4.47 g) was chromatographed on silica gel, using 2/1, ethylacetate/hexane, as eluting solvent. The appropriate fractions were combined and concentrated under reduced pressure to yield a yellow foam (4.02 g).

B. Preparation of 5'-Azido-5' deoxy-2-bromo-2',3'-isopropylidene AICA Riboside

5'-deoxy-5'-iodo-2-bromo-2',3'-isopropylidene AICA riboside (4.02 g) lithium azide (1.82 g), and DMF (65 ml) were combined and stirred at ambient temperature for 2 hours. The solvent was evaporated under reduced pressure to give a yellow oil. The oil was dissolved in ethyl acetate (200 ml), washed with water and brine, then dried over magnesium sulfate. The solvent was evaporated under reduced pressure to give a yellow foam (3.01 g).

C. Preparation of 5'-Amino-5'-deoxy-2-bromo-2',3'-isopropylidene AICA Riboside

5'-azido-5'-deoxy-2-bromo-2',3'-isopropylidene AICA riboside (2.00 g), triphenylphosphine (1.83 g), and THF (100 g) were combined and stirred at room temperature for 16 hours. Concentrated NH₄OH (15 ml) was added and the solution heated at reflux for 6 hours. The solution was cooled and the solvent evaporated under reduced pressure. The resulting residue was coevaporated with methanol (2×30 ml). The resulting residue was stirred in cold methanol (25 ml) for 30 minutes. The mixture was filtered to give an off-white powder. The solid was recrystallized from methanol to give a white powder (0.73 g).

D. Preparation of 5-Amino-2-thio-1-(5-amino-5-deoxy-β-D-ribofuranosyl)imidazole-4-carboxamide (Compound No. 70 (1-551))

Potassium sulfide (1.0 g) was heated at reflux in ethanol (10 ml) for 15 minutes. The mixture was filtered and to the filtrate was added 5'-amino-5'-deoxy-2-bromo-2',3'-isopropylidene AICA riboside (0.50 g). The mixture was heated in a steel bomb at 110° C. for 5 hours. The mixture was cooled and filtered. The filtrate was again filtered, then concentrated under reduced pressure to give a yellow tar. The tar was chromatographed on silica gel, using 3/1, methylene chloride/methanol, as eluting solvent. The appropriate fractions were combined and concentrated under reduced pressure to give a yellow glass (0.12 g). The glass was dissolved in 80% of trifluoroacetic acid (8 ml) and stirred at room temperature for 1 hour. The solvent was evaporated under reduced pressure to give a yellow solid. The solid was stirred in diethylether/ethanol (10 ml of 95/5), then filtered and dried to yield a yellow solid (55 mg).

¹H NMR (DMSO-d₆+D₂O) δ ppm. 2.6–2.9(m, 2H, 5'-CH₂—), 3.8–4.5(m, 3H, 2'-CH, 3'-CH, 4'-CH), 6.2(d, 1H, 1'-CH).

Example AZ

Preparation of 5-Amino-1-(5-azido-5-deoxy-β-D-ribofuranosyl)imidazole-4-N-|(4-nitrophenyl)methyl|carboxamide (Compound No. 71 (1-562))

This compound was prepared according to the procedures described in example AH for compound 52 (1-467), substituting compound 23 (1-343) (p-nitrobenzyl derivative), for compound 29 (1-349) (p-chlorobenzyl derivative).

¹H NMR (DMSO-d₆) δ ppm. 3.5–3.7(m, 2H, 5'-CH₂), 3.9–4.4(m, 3H, 2'-CH, 3'-CH, 4'-CH), 4.4–4.5(d, 2H, —CH₂—PhNO₂), 5.4–5.5(m, 2H, 2'-OH, 3'-OH), 5.5(d, 1H, 1'-CH), 5.9(br.s., 2H, 5-NH₂), 7.4(s, 1H, 2-CH), 6.5–8.2 (m, 4H, —C₆H₄NO₂), 8.3(4, 1H, CONH—).

Example BA

Preparation of 5-Amino-1-(5-amino-5-deoxy-β-D-ribofuranosyl)imidazole-4-N-[4-nitrophenyl)methyl] carboxamide (Compound No. 72 (1-563))

This compound was prepared according to the procedures described in Example AH for compared 53 (1-468), substituting the p-nitrobenzyl amide derivative (compound 23 (1-343)) for the p-chlorobenzyl amide derivative (compound 29 (1-349)).

¹H NMR (DMSO+D₂O) δ ppm 2.6–2.8(m, 2H, 5'-CH₂—), 3.8–4.3(m, 3H, 2'-CH, 3'-CH, 4'-CH), 4.4–4.5(m, 2H, —CH₂—C₆H₄NO₂), 5.4(d, 1H, 1'-CH), 7.3(s, 1H, 2-CH), 7.5–8.3(m, 5H, CH₂C₆H₄NO₂, 4-CONH).

Example BB

Preparation of 5-Amino-1-β-D-ribofuranosyl-imidazole-4-N-|(4-(trifluoromethylphenyl)methyl| carboxamide (Compound No. 74 (1-572))

This compound was prepared according to the procedures described in Example J for the p-nitrobenzyl derivative substituting 4-(trifluoromethyl)benzylamine for 4-nitrobenzyl amine hydrochloride. The final product was recrystallized from methylene chloride/methanol. Mp=137–140.

¹H NMR (DMSO-d₆) δ ppm 3.5–3.7 (m, 2H, 5'-CH₂), 3.9–4.4 (m, 3H, 2'-CH, 3'-CH, 4'-CH), 4.4–4.5 (d, 2H, —CH₂—PhCF₃), 5.2–5.5 (m, 3H, 2'-OH, 3'-OH, 5'-OH), 5.5 (d, 1H, 1'-CH), 5.9 (br.s., 2H, 5-NH₂), 7.3 (S, 1H, 2-CH), 7.4–7.7 (m, 4H, —C₆H₄CF₃), 8.2 (t, 1H, 4-CONH).

Example BC

Preparation of 5-Amino-1-β-D-ribofuranosylimidazole-4-N-|(4-sulfamoylphenyl) methyl|carboxamide (Compound No. 75 (1–577))

This compound was prepared according to the procedures described in Example J for the p-nitrobenzyl derivative, substituting 4-(aminomethyl)benzene sulfonamide hydrochloride for 4-nitrobenzylamine hydrochloride.

¹H NMR (DMSO-d₆) δ ppm. 3.5–3.7(m, 2H, 5'-CH₂—), 3.9–4.4(m, 3H, 2'-CH, 3'-CH, 4'-CH), 4.4–4.5(d, 2H, —CH₂—C₆H₄SO₂), 5.2–5.4(m, 3H, 2'-OH, 3'-OH, 5'-OH), 5.5(d, 1H, 1'-CH), 6.0(br.s., 2H, 5-NH₂), 7.3(br.s., 2H, —SO₂NH₂), 7.4(s, 1H, 2-CH), 7.4–7.8(m, 4H, —C₆H₄—), 8.2 (t, 1H, 4-CONH—).

Example BD

Preparation of 5-Amino-1-(5-(4-chlorobenzyl-amino)-5-deoxyβ-D-ribofuranosyl)imidazole-4-carboxamide (Compound No. 76 (1-578))

5'-amino-5'-deoxy-AICA-riboside (0.50 g) (compound No. 21 (1-227)) of Table VIII, 4-chlorobenzyl iodide (0.50 g), potassium carbonate (0.26 g), and DMF (15 ml) were combined and stirred at room temperature for 16 hours. The solvent was evaporated under reduced pressure and the resulting residue stirred in warm ethanol (35 ml). The insolubles were removed by filtration and the filtrate concentrated under reduced pressure. The resulting residue was chromatrographed on silica gel, using 3:1, methylene chloride:methanol, as eluting solvent. The fractions containing the slower moving of the two products were combined and concentrated under reduced pressure to yield a tan foam (0.21 g)

¹H NMR (DMSO-d₆+D₂) δ ppm 2.9–3.0 (m, 2H, 5'-CH₂—), 3.9(s, 2H, —CH₂—C₆H₄), 3.9–4.3(m, 3H, 2'-CH, 3'-CH, 4'-CH), 5.5(d, 1H, 1'-CH), 7.3(s, 1H, 2-CH), 7.4(m, 4H, —C₆H₄Cl).

Example BE

Preparation of 5-Amino-1-(5-deoxy-β-D-ribofuranosyl)imidazole; (Compound No. 77 (1-588))

5'-deoxy AICA riboside (1.00 g) (ref: P. C. Srivastava, A. R. Newman, T. R. Mathews, and R. F. Robins, J. Med. Chem. 18: 1237 (1975) was heated at reflux in N potassium hydroxide (4.0 ml) for 5 hours. The solvent was evaporated under reduced pressure and the resulting residue co-evaporated with ethanol (4×10 ml). The resulting residue was diluted with ethanol (15 ml) and a fine precipitate was filtered. Upon setting for several days, the filtrate gave an additional precipitate. The microscopic solid was collected, and the combined solid material was dissolved in water (20 ml) and neutralized with Dowex 50W strongly acidic ion exchange resin. The solvent was evaporated under reduced pressure to give a dark tar. The tar was dissolved in 80% acetic acid (20 ml) and gently heated (60° C.). The solvent was evaporated under reduced pressure to give a dark tar. The tar was co-evaporated with methanol (2×15 ml). The resulting residue was chromatographed on silica gel, using 3/1, methylene chloride/methanol, as eluting solvent. The appropriate fractions were combined and concentrated under reduced pressure to yield a dark tar. The tar was co-evaporated with toluene (3×20 ml), then vacuum dried to yield a dark brown, hygroscopic foam (110 mg).

$^1$H NMR (D$_2$) δ ppm, 1.3(d, 3H, 5'-CH$_3$), 4.0–4.5(m, 3H, 2'-CH, 3'-CH, 4'-CH), 5.6(d, 1H, 1'-CH), 6.4(s, 1H, 4-CH), 7.7(s, 1H, 2-CH).

Example BF

Preparation of 5-Amino-1-(5-deoxy-5-diethylaminoribo-β,D-furanosyl)imidazole-4-carboxamide (Compound No.65 (1-522)

5-deoxy-5'-iodo-2',3'-isopropylidene AICA riboside (1.00 g) (ref.: P. C. Srivastava, A. R. Newman, T. R. Mathews, and R. K. Robins, J. Med. Chem. 18: 1237, (1975)), diethylamine (2.5 ml of 40 wt % in water), and methanol (30 ml) were combined and heated at reflux for 18 hours. The procedures described in Example AS for compound 63 (1-519) were followed to give the above-identified compound.

$^1$H NMR (DMSO-d$_6$) δ ppm 0.9 (t, 6H, methyl groups on 5'-diethylamine), 2.4–2.7 (m, 6H, 5'-CH$_2$, methylene groups on 5'-diethylamine), 3.3–4.2 (m, 3H, 2'-CH, 3'-CH, 4'-CH), 5.2 (br., 2H, 2'-OH, 3'-OH), 5.4(d, 1H, 1'-CH), 5.9(br.s., 2H, 5-NH$_2$), 5.7–5.9 (br., 2H, 4-CONH$_2$), 7.3(s, 1H, 2-CH).

Example BG

Preparation of 5-Amino-1-β-D-ribofuranosylimidazole-4-N-[3-4-nitrophenyl)propyl]carboxamide (Compound No. 73 (1-566))

This compound was prepared according to the procedures described in Example J for the p-nitrophenyl derivative, substituting 3-(4-nitrophenyl)propylamine (ref: G. W. Hardy, et al., J. Med. Chem. 32: 1108, (1989)) for p-nitrobenzylamine hydrochloride.

$^1$H NMR (DMSO-d$_6$) δ ppm 1.7–3.2 (m, 6H, —CH$_2$CH$_2$—), 3.5–3.6 (m, 2H, 5'-CH$_2$), 3.9–4.3 (m, 3H, 2'-CH, 3'-CH, 4'-CH), 5.2–5.4(m, 3H, 2'-OH, 3'-OH, 5'-OH), 5.5(d, 2H, 1'-CH), 5.9(br.s., 2H, 5-NH$_2$), 7.3 (s, 1H, 2-CH), 7.5–8.2 (m, 5H, —CH$_6$H$_4$NO$_2$, 4-CONH—).

Example BH

Preparation of 5-Amino-1-(5-amino-5-deoxy-2,3-di-O-acetyl-β-D-ribofuranosyl)imidazole-4-N-[(4-chlorophenyl)methyl]carboxamide, (Compound No. 78 (1–599))

A. Preparation of 5-amino-1-(5-azido-5-deoxy-2,3-di-O-acetyl-β-D-ribofuranosyl)imidazole-4-N-[4-chlorophenyl)methyl]carboxamide Compound 52 (example AH), 2.4 g (5.8 mmol), was dissolved in a mixture of 20 ml of diemthylformamide and 20 ml of pyridine. The solution was cooled to 30° C. under argon, and acetic anhydride, 1.5 g, (14 mmol), was added. The mixture was allowed to warm to room temperature over 18 hours and then concentrated to a syrup. The syrup was dissolved in 25 ml of methylene chloride and washed with 3×15 ml of water, dried over magnesium sulfate and evaporated to yield 3.0 grams of a white foam. This was further purified by chromatography on 200 ml of silica gel using a mixture of methylene chloride and methanol (95:5), yielding 2.5 grams of the desired product as a white foam.

B. Preparation of 5-amino-(5-amino-5-deoxy-2,3-di-O acetyl-β-D-ribofuranosyl)imidazole-4-N-[(4-chlorophenyl)methyl]carboxamide (Compound No. 78 (1-599))

The product of step A, 400 mg, was dissolved in 10 ml of ethanol and 50 mg of 10% Pd on carbon was added. The mixture was stirred under a hydrogen atmosphere for 30 minutes, filtered and the filtrate evaporated to yield 300 mg of the desired product as a white foam.

$^1$H NMR (DMSO-d$_6$) δ 2.0 (s, 3H, CH$_3$CO—), 2.1 (s, 3H, CH$_3$CO—), 2.9 (m, 2H, 5'-CH$_2$), 4.1 (m, 1H, 4'-CH), 3.4 (br. s, 2H, 5'-NH$_2$) 4.4 (d, 2H, —CH$_2$—C$_6$H$_4$—Cl), 5.3 (m, 1H, 3'-CH) 5.6 (m, 1H, 3'-CH), 5.8 (d, 1H, 1'-CH), 6.4 (br. s, 2H, 5-NH$_2$), 7.3 (m, 4H, —C$_6$H$_4$—Cl), 7.4 (s, 1H, 2-CH), 8.1 (t, 1H, 4-CONH—).

Example BI

Prodrugs of the invention can also be prepared and administered under appropriate conditions. In a preferred embodiment, the prodrugs of the invention enhance oral bioavailability, and include in particular the carboxylic acid esters of 2' and 3' hydroxyls.

Prodrug esters of the invention can be made by standard acetylation procedures, which may involve protection and deprotection steps. For example, the 5' group of Series III compounds may require protection (e.g., the 5'-benzylamino of Compound 66 can be protected with a benzyloxycarbonyl group.)

Preparation of 5-Amino-1-(5-N-benzylamino-2,3,-di-O-pivaloyl-5-deoxy-β-D-ribofuranosyl)imidazole-4-carboxamide (Prodrug of Compound 66)

1-(5-N-benzylamino-5-deoxy-β-D-ribofuranosyl) imidazole-4-carboxamide tartrate salt (8.8 g, 16.77 mmol) in water (60 mL), potassium carbonate (8.5 g), and tetrahydrofuran (120 mL) was taken in a three-necked round bottom flask fitted with a mechanical stirrer, an addition funnel, and a nitrogen inlet. The flask was cooled in an ice water bath. A solution of benzyl chloroformate (3.4 mL, 20 mmol) in THF (15 mL) was added over a period of 1 5 minutes. The cooling bath was removed and stirring was continued for two hours, at which time t.l.c. (SiO$_2$, 6:1 CH$_2$Cl$_2$-Methanol) indicated complete consumption of the starting material. The reaction mixture was transferred to a separatory funnel and the organic layer was separated. The aqueous layer was washed with ethyl acetate (3×30 ml). The organic layers were combined, dried over anhydrous MgSO$_4$ and evaporated to obtain a syrupy residue. The product was further purified by column chromatography using 9:1 CH$_2$Cl$_2$-Methanol as the eluting system. Fractions containing the product were pooled and evaporated to obtain A. 5-amino-1-(5-N-benzylamino-N-benyoxycarbonyl-5-deoxy-β-D-ribofuranosyl)imidazole-4-carboxamide as a glassy solid. Yield: 5.5 g. Rf=0.5 SiO$_2$, 6:1 CH$_2$Cl$_2$-Methanol.

A solution of compound A (2.0 g, 4.15 mmol) and 4-N,N-dimethylaminopyridine (100 mg) in dry pyridine (20 mL) was cooled in an ice water bath and treated with pivalic anhydride (3.3 mL). The ice bath was removed and the reaction mixture was stirred at room temperature for 16 hours. The t.l.c. (SiO$_2$, 9:1 CH$_2$Cl$_2$-Methanol) indicated complete consumption of the starting material. Methanol (1.5 mL) was added and stirred for an additional half-hour and the volatiles were evaporated under reduced pressure. The residue was dissolved in ethyl acetate (50 mL) and extracted with water (1×50 mL) and sodium bicarbonate solution (1×20 mL). The organic layer was dried over anhydrous $MgSO_4$ and evaporated to obtain a syrupy residue. The product was further purified by column chromatography using 19:1 $CH_2Cl_2$-Methanol as the eluting system. Fractions containing the product were pooled and evaporated to obtain B. 5-amino-1-(5-N-benzylamino-N-benyoxycarbonyl-2, 3-di-O-pivaloyl-5-deoxy-β-D-ribofuranosyl) imidazole-4-carboxamide as a glassy solid. Yield: 5.5 g. Rf=0.6 $SiO_2$, 9:1 $CH_2Cl_2$-Methanol. HNMR. DMSC-$d_6$ δ ppm.

To a solution of compound B (1.1 g) in ethyl acetate (30.0 mL) and acetic acid (6.0 mL) the catalyst $Pd(OH)_2$ on carbon (100 mg) was added and purged with nitrogen. Hydrogenation was carried out using a balloon of hydrogen. Completion of the reaction was evidenced by the absence of starting material on t.l.c. ($SiO_2$, 9:1 $CH_2Cl_2$-Methanol). The catalyst was removed by filtration through a celite pad and washed with ethyl acetate. The filtrate was evaporated under reduced pressure and the residue was redissolved in ethyl acetate (50 mL) and extracted with saturated sodium bicarbonate solution (1×20 mL). The organic layer was dried over anhydrous $MgSO_4$ and evaporated to obtain a residue which was further purified over a silica gel column using 19:1 $CH_2Cl_2$-Methanol as the eluting system. Fractions containing the product were pooled and evaporated to obtain C. 5-amino-1-(5-N-benzylamino-N-benylamino-2,3-di-O-pivaloyl-5-deoxy-β-D-ribofuranosyl)imidazole-4-carboxamide as a glassy solid. Yield: 800 mg. Rf=0.55 $SiO_2$, 9:1 $CH_2Cl_2$-Methanol.

To obtain the corresponding hydrochloride salt of the title compound, the above free base (200 mg) was dissolved in methanol and diluted with 1N aqueous HCL solution. The resulting solution was evaporated under reduced pressure (bath temperature, 30 C.). The residue was dissolved in double distilled water (15 mL) and filtered through a 45µ membrane filter. The filtrate was frozen in a lyophilizing jar and lyophilized repeatedly until a constant weight was obtained. The final product 5-amino-1-(5-N-benzylamino-N-benylamino-2,3-di-O-pivaloyl-5-deoxy-β-D-ribofuranosyl)imidazole-4-carboxamide hydrochloride was obtained as a white solid was dried under high vacuum and stored in the freezer. Yield: 180 mg, m.p. 172°–175° C.

The following prodrugs can be made in a similar manner:

5-amino-1-(5-N-benzylamino-2,3-di-O-acetyl-5-deoxy-β-D-ribofuranosyl)imidazole-4-carboxamide 5-amino-1-(5-N-benzylamino-2,3-di-O-propionyl-5-deoxy-β-D-ribofuranosyl)imidazole-4-carboxamide 5-amino-1-(5-N-benzylamino-2,3-di-O-butyryl-5-deoxy-β-D-ribofuranosyl)imidazole-4-carboxamide 5-amino-1-(5-N-benzylamino-2,3-di-O-isobutyryl-5-deoxy-β-D-ribofuranosyl)imidazole-4-carboxamide 5-amino-1-(5-N-benzylamino-2,3-di-O-pentanoyl-5-deoxy-β-D-ribofuranosyl)imidazole-4-carboxamide 5-amino-1-(5-N-benzylamino-2,3-di-O-benzoyl-5-deoxy-β-D-ribofuranosyl)imidazole-4-carboxamide 5-amino-1-(5-N-benzylamino-2,3-di-O-(4-methylbenzoyl)-5-deoxy-β-D-ribofuranosyl)imidazole-4-carboxamide 5-amino-1-(5-N-benzylamino-2,3-di-O-phenylacetyl-5-deoxy-β-D-ribofuranosyl)imidazole-4-carboxamide 5-amino-1-(5-N-benzylamino-2,3-di-O-palmitoyl-5-deoxy-β-D-ribofuranosyl)imidazole-4-carboxamide 5-amino-1-(5-N-benzylamino-2,3-di-O-oleyl-5-deoxy-β-D-ribofuranosyl)imidazole-4-carboxamide 5-amino-1-(5-N-benzylamino-5-deoxy-β-D-ribofuranosyl)imidazole-4-carboxamide-2',3'-cyclic carbonate.

Example BJ

The oral bioavailability of Compound 66 (1-531) and one of its prodrugs (Example BH) was studied, based on urinary excretion of Compound 66 following its administration, and administration of the prodrug. An IV bolus of Compound 66 was used as the 100% bioavailable control.

Four rats were used for each drug and each route of administration. Food was removed for two hours prior to and two hours after dosing; water was allowed. The first group of rats received an aqueous solution of Compound 66 as a tartate salt (20 mg/kg equivalents of free base) as a bolus via the tail vein. The second group received an aqueous solution of Compound 66 as a tartrate salt (20 mg/kg equivalents of free base) by oral gavage. The third group of rats received a solution of the prodrug, 5-Amino-1-(5-N-benzylamino-2, 3,-di-O-pivaloyl-5-deoxy-β-D-ribofuranosyl)imidazole-4-carboxamide (20 mg/kg equivalents of Compound 66 as a free base) by oral gavage.

The rats were kept in metabolic cages, and urine was collected over the following intervals: −15–0 (control), 0–24, and 24–48 hours. The volume of each collection was recorded and a 5 mL aliquot was frozen at −20° C. The urinary concentrations of Compound 66 were then determined for these IV and oral administrations.

The samples were assayed for intact Compound 66 by HPLC. Each sample was diluted 1:10 with water prior to HPLC analysis, which was performed on a Beckman Ultrasphere $C_{18}$ reverse phase column (4.6×150 mm, 5 micron) eluted isocratically at ambient temperature with a mobile phase of 40% methanol and 20 mM heptane sulfonic acid (sodium salt) at a flow rate of 1.5 ml/min. The eluant was monitored by UV absorbance at 259 nm.

Oral bioavailability was determined by comparing the amount of Compound 66 free base excreted as a percent of dose following IV and oral dosing. Bioavailability was estimated to be approximately 48% for the prodrug and 14% for the tartrate.

TABLE XII

COMPOUNDS OF THE FORMULA

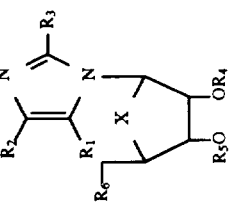

| Compound No. | $R_1$ | $R_2$ | $R_3$ | X | $R_4$ | $R_5$ | $R_6$ |
|---|---|---|---|---|---|---|---|
| 1(1-110) | $-NH_2$ | $-\overset{O}{\underset{\|}{C}}NH_2$ | $-H$ | $-O-$ | $-H$ | $-H$ | $-OH$ |
| 2(1-111) | $-NH_2$ | $-\overset{O}{\underset{\|}{C}}NH_2$ | $-H$ | $-O-$ | $-\overset{O}{\underset{\|}{C}}CH_3$ | $-\overset{O}{\underset{\|}{C}}CH_3$ | $-OCCH_3$ $\overset{\|}{O}$ |
| 3(1-115) | $-NH_2$ | $-CN$ | $-H$ | $-O-$ | $-H$ | $-H$ | $-OH$ |
| 4(1-122) | $-NH_2$ | $\underset{NH_2}{\overset{NOH}{\underset{\|}{C}}}$ | $-H$ | $-O-$ | $-H$ | $-H$ | $-OH$ |
| 5(1-145) | $-NH_2$ | $-\overset{O}{\underset{\|}{C}}NH_2$ | $-H$ | $-CH_2-$ | $-H$ | $-H$ | $-OH$ |
| 6(1-155) | $-NH_2$ | $\underset{NH}{\overset{OCH_2CH_3}{\underset{\|}{C}}}$ | $-H$ | $-O-$ | $-H$ | $-H$ | $-OH$ |
| 7(1-164) | $-N=CHN(CH_3)_2$ | $-\overset{O}{\underset{\|}{C}}NH_2$ | $-H$ | $-O-$ | $-H$ | $-H$ | $-OH$ |
| 8(1-172) | $-NH_2$ | $-\overset{O}{\underset{\|}{C}}NH_2$ | $-H$ | $-O-$ | $-H$ | $-H$ | $-O-\overset{O}{\underset{\|}{P}}-OH$ $\overset{\|}{OH}$ |
| 9(1-177) | $-\overset{O}{\underset{\|}{NHCCH_3}}$ | $-\overset{O}{\underset{\|}{C}}NH_2$ | $-H$ | $-O-$ | $-\overset{O}{\underset{\|}{C}}CH_3$ | $-\overset{O}{\underset{\|}{C}}CH_3$ | $-OCCH_3$ $\overset{\|}{O}$ |

TABLE XII-continued

COMPOUNDS OF THE FORMULA

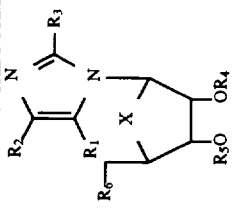

| Compound No. | $R_1$ | $R_2$ | $R_3$ | X | $R_4$ | $R_5$ | $R_6$ |
|---|---|---|---|---|---|---|---|
| 10(1-186) | $-NH_2$ | $-\overset{O}{\underset{\|}{C}}NH-\text{cyclopentyl}$ | $-H$ | $-O-$ | $-H$ | $-H$ | $-OH$ |
| 11(1-226) | $-NH_2$ | $-\overset{O}{\underset{\|}{C}}NH-CH_2-\text{phenyl}$ | $-H$ | $-O-$ | $-H$ | $-H$ | $-OH$ |
| 12(1-232) | $-NH_2$ | $-\overset{O}{\underset{\|}{C}}NH-\text{cyclopropyl}$ | $-H$ | $-O-$ | $-H$ | $-H$ | $-OH$ |
| 13(1-240) | $-NH_2$ | $-\overset{O}{\underset{\|}{C}}NH_2$ | $-Br$ | $-O-$ | $-H$ | $-H$ | $-OH$ |
| 14(1-260) | $-NH_2$ | $-\overset{O}{\underset{\|}{C}}OCH_3$ | $-H$ | $-O-$ | $-H$ | $-H$ | $-OH$ |
| 15(1-261) | $-NH_2$ | $-\overset{O}{\underset{\|}{C}}NH_2$ | $-H$ | $-O-$ | $-H$ | $-H$ | $-OS(O)_2NH_2$ |
| 16(1-273) | $-NH_2$ | $-H$ | $-H$ | $-O-$ | $-H$ | $-H$ | $-OH$ |
| 17(1-295) | $-\overset{O}{\underset{\|}{NHCCH_3}}$ | $-H$ | $-H$ | $-O-$ | $-H$ | $-H$ | $-OH$ |

TABLE XII-continued

COMPOUNDS OF THE FORMULA

| Compound No. | $R_1$ | $R_2$ | $R_3$ | X | $R_4$ | $R_5$ | $R_6$ |
|---|---|---|---|---|---|---|---|
| 18(1-335) | $-NH_2$ | ![C(=NOCH₃)NH₂] | $-H$ | $-O-$ | $-H$ | $-H$ | $-OH$ |
| 19(1-154) | $-NH_2$ | $O=\overset{\|}{C}NH_2$ | $-H$ | $-O-$ | $-H$ | $-H$ | $-H$ |
| 20(1-188) | $-NH_2$ | $O=\overset{\|}{C}NH_2$ | $-H$ | $-O-$ | $-CH_3$ | $-H$ | $-OH$ |
| 21(1-227) | $-NH_2$ | $O=\overset{\|}{C}NH_2$ | $-H$ | $-O-$ | $-H$ | $-H$ | $-NH_2$ |
| 22(1-243) | $-NH_2$ | $O=\overset{\|}{C}NH_2$ | $-H$ | $-O-$ | $-H$ | $-CH_3$ | $-OH$ |
| 23(1-343) | $-NH_2$ | $O=\overset{\|}{C}NHCH_2$-(4-NO₂-C₆H₄) | $-H$ | $-O-$ | $-H$ | $-H$ | $-OH$ |
| 24(1-354) | $-NH_2$ | $O=\overset{\|}{C}NHCH_2$-(2-Cl-C₆H₄) | $-H$ | $-O-$ | $-H$ | $-H$ | $-OH$ |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 25(1-360) | $-NH_2$ | $-\underset{\underset{O}{\|\|}}{C}NHCH_2$—(2,4-dichlorophenyl) | $-H$ | $-O-$ | $-H$ | $-H$ | $-OH$ |
| 26(1-332) | $-NH_2$ | $-\underset{\underset{O}{\|\|}}{C}NH_2$ | $-H$ | $-O-$ | $-H$ | $-H$ | $-Cl$ |
| 27(1-395) | $-NH_2$ | $-\underset{\underset{O}{\|\|}}{C}NH_2$ | $-SH$ | $-O-$ | $-H$ | $-H$ | $-OH$ |
| 28(1-348) | $-NH_2$ | $-\underset{\underset{O}{\|\|}}{C}NH_2$ | $-H$ | $-O-$ | $-H$ | $-H$ | $-OH$ |
| 29(1-349) | $-NH_2$ | $-\underset{\underset{O}{\|\|}}{C}NHCH_2$—(3-nitrophenyl) | $-H$ | $-O-$ | $-H$ | $-H$ | $-OH$ |
| 30(1-388) | $-NH_2$ | $-\underset{\underset{O}{\|\|}}{C}NHCH_2$—(4-chlorophenyl) | $-H$ | $-O-$ | $-H$ | $-H$ | $-OH$ |
| 31(1-251) | $-NH_2$ | $-\underset{\underset{O}{\|\|}}{C}NH_2$—(4-methylphenyl) | $-H$ | $-O-$ | $-H$ | $-CH_2CH_3$ | $-OH$ |

TABLE XII-continued

COMPOUNDS OF THE FORMULA

[Structure: fused bicyclic ring with R₂, R₁, R₃, X, OR₄, R₅O, R₆ substituents]

| Compound No. | R₁ | R₂ | R₃ | X | R₄ | R₅ | R₆ |
|---|---|---|---|---|---|---|---|
| 32(1-262) | $-NH_2$ | $O=C-NH_2$ | $-H$ | $-O-$ | $-(CH_2)_3CH_3$ | $-H$ | $-OH$ |
| 33(1-263) | $-NH_2$ | $O=C-NH_2$ | $-H$ | $-O-$ | $-H$ | $-(CH_2)_3CH_3$ | $-OH$ |
| 34(1-250) | $-NH_2$ | $O=C-NH_2$ | $-H$ | $-O-$ | $-CH_2CH_3$ | $-H$ | $-OH$ |
| 35(1-355) | $-NH_2$ | $O=C-NH-CH_2-$(3-Cl-phenyl) | $-H$ | $-O-$ | $-H$ | $-H$ | $-OH$ |
| 36(1-207) | $-NH_2$ | $O=C-N$(piperidinyl) | $-H$ | $-O-$ | $-H$ | $-H$ | $-OH$ |
| 37(1-270) | $-NH_2$ | $O=C-NH-$cyclopentyl | $-H$ | $-O-$ | $-H$ | $-H$ | $-NH_2$ |
| 38(1-351) | $-N=C(H)-N(CH_3)_2$ | $O=C-CH_2-N_3$ | $-H$ | $-O-$ | $-H$ | $-H$ | $-OH$ |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 39(1-390) | $-NH_2$ | $-\overset{O}{\underset{\|}{C}}-NH-CH_2-$⌬-$OCH_3$ | $-H$ | $-O-$ | $-H$ | $-H$ | $-OH$ |
| 40(1-392) | $-NH_2$ | $-\overset{S}{\underset{\|}{C}}-NH_2$ | $-H$ | $-O-$ | $-H$ | $-H$ | $-OH$ |
| 41(1-396-3) | $-NH_2$ | $-\overset{O}{\underset{\|}{C}}-NH-CH_2-$⌬-$NH^+Cl^-$(CH₃)₂ | $-H$ | $-O-$ | $-H$ | $-H$ | $-OH$ |
| 42(1-431) | $-NH_2$ | $-\overset{O}{\underset{\|}{C}}-NH-CH_2-$⌬(OH)-CH(OH)- | $-H$ | $-O-$ | $-H$ | $-H$ | $-OH$ |
| 43(1-432) | $-NH_2$ | $-\overset{O}{\underset{\|}{C}}-NH_2$ | $-S-$⌬ | $-O-$⌬ | $-H$ | $-H$ | $-OH$ |
| 44(1-434) | $-NH_2$ | $-\overset{O}{\underset{\|}{C}}-NH-CH_2-$⌬-$I$ | $-H$ | $-O-$ | $-H$ | $-H$ | $-OH$ |

TABLE XII-continued

COMPOUNDS OF THE FORMULA

[Structure: R2-C(=N)-... pyrimidine fused ring system with R1, R3, R4, R5O, R6, X, OR4 substituents]

| Compound No. | R1 | R2 | R3 | X | R4 | R5 | R6 |
|---|---|---|---|---|---|---|---|
| 45(1-438) | —NH₂ | O=C—NH—(norbornyl) | —H | —O— | —H | —H | —OH |
| 46(1-445) | —NH₂ | O=C—NH—CH₂—(4-NO₂-C₆H₄) | —H | —O— | —H | —H | —I |
| 47(1-450) | —NH₂ | O=C—S—CH₂—(4-NO₂-C₆H₄) | —H | —O— | —H | —H | —OH |
| 48(1-452) | —NH₂ | O=C—N(indoline) | —H | —O— | —H | —H | —OH |
| 49(1-453) | —NH₂ | O=C—NH—CH(CH₃)—(4-NO₂-C₆H₄) | —H | —O— | —H | —H | —OH |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 50(1-459) | —NH₂ | O=C—NH—C(CH₃)(H)—(4-NO₂-C₆H₄) | —H | —O— | —H | —H | —OH |
| 51(1-466) | —NH₂ | O=C—NH—CH₂—(4-NO₂-C₆H₄) | —H | —O— | —H | —H | —Cl |
| 52(1-459) | —NH₂ | O=C—NH—CH₂—(4-Cl-C₆H₄) | —H | —O— | —H | —H | —N₃ |
| 53(1-468) | —NH₂ | O=C—NH—CH₂—(4-Cl-C₆H₄) | —H | —O— | —H | —H | —NH₃⁺Cl⁻ |
| 54(1-483) | —NH₂ | O=C—NH₂ (4-Br-C₆H₄) | —H | —O— | —H | —H | —S—CH₃ |
| 55(1-484) | —NH₂ | O=C—NH—(4-Br-C₆H₄) | —H | —O— | —H | —H | —OH |
| 56(1-487) | —NH₂ | O=C—NH—CH₂—(4-Br-C₆H₄) | —H | —O— | —H | —H | —OH |

TABLE XII-continued

COMPOUNDS OF THE FORMULA $$\begin{array}{c} R_2 \\ \diagdown \\ R_6 \end{array} \begin{array}{c} N \\ \diagup \\ R_1 \end{array} \begin{array}{c} R_3 \\ \diagup \\ X \end{array} \begin{array}{c} OR_4 \\ \diagup \\ R_5O \end{array}$$

| Compound No. | $R_1$ | $R_2$ | $R_3$ | X | $R_4$ | $R_5$ | $R_6$ |
|---|---|---|---|---|---|---|---|
| 57(1-488) | $-NH_2$ | $-\overset{O}{\underset{\parallel}{C}}-NH-\!\!\left\langle\!\!\bigcirc\!\!\right\rangle\!\!-I$ | $-H$ | $-O-$ | $-H$ | $-H$ | $-OH$ |
| 58(1-489) | $-NH_2$ | $-\overset{O}{\underset{\parallel}{C}}-NH-\!\!\left\langle\!\!\bigcirc\!\!\right\rangle\!\!-NO_2$ | $-H$ | $-O-$ | $-H$ | $-H$ | $-OH$ |
| 59(1-506) | $-NH_2$ | $-\overset{O}{\underset{\parallel}{C}}-NH-CH_2-CH_2-\!\!\left\langle\!\!\bigcirc\!\!\right\rangle\!\!-NO_2$ | $-H$ | $-O-$ | $-H$ | $-H$ | $-OH$ |
| 60(1-508) | $-NH_2$ | $-\overset{O}{\underset{\parallel}{C}}-N\!\!\left\langle\!\!\bigcirc\!\!\right\rangle\!\!N-\!\!\left\langle\!\!\bigcirc\!\!\right\rangle\!\!-NO_2$ | $-H$ | $-O-$ | $-H$ | $-H$ | $-OH$ |
| 61(1-509) | $-NH_2$ | $-\overset{O}{\underset{\parallel}{C}}-NH-CH_2-\!\!\left\langle\!\!\bigcirc\!\!\right\rangle\!\!-Cl$ | $-H$ | $-O-$ | $-H$ | $-H$ | $-OH$ |
| 62(1-510) | $-NH_2$ | $-\overset{O}{\underset{\parallel}{C}}-NH_2$ | $-H$ | $-O-$ | $-H$ | $-H$ | $-\overset{O}{\underset{\parallel}{S}}-CH_3$ |
| 63(1-517) | $-NH_2$ | $-\overset{O}{\underset{\parallel}{C}}-NH_2$ | $-H$ | $-O-$ | $-H$ | $-H$ | $-NH-CH_3$ |

TABLE XII-continued
COMPOUNDS OF THE FORMULA
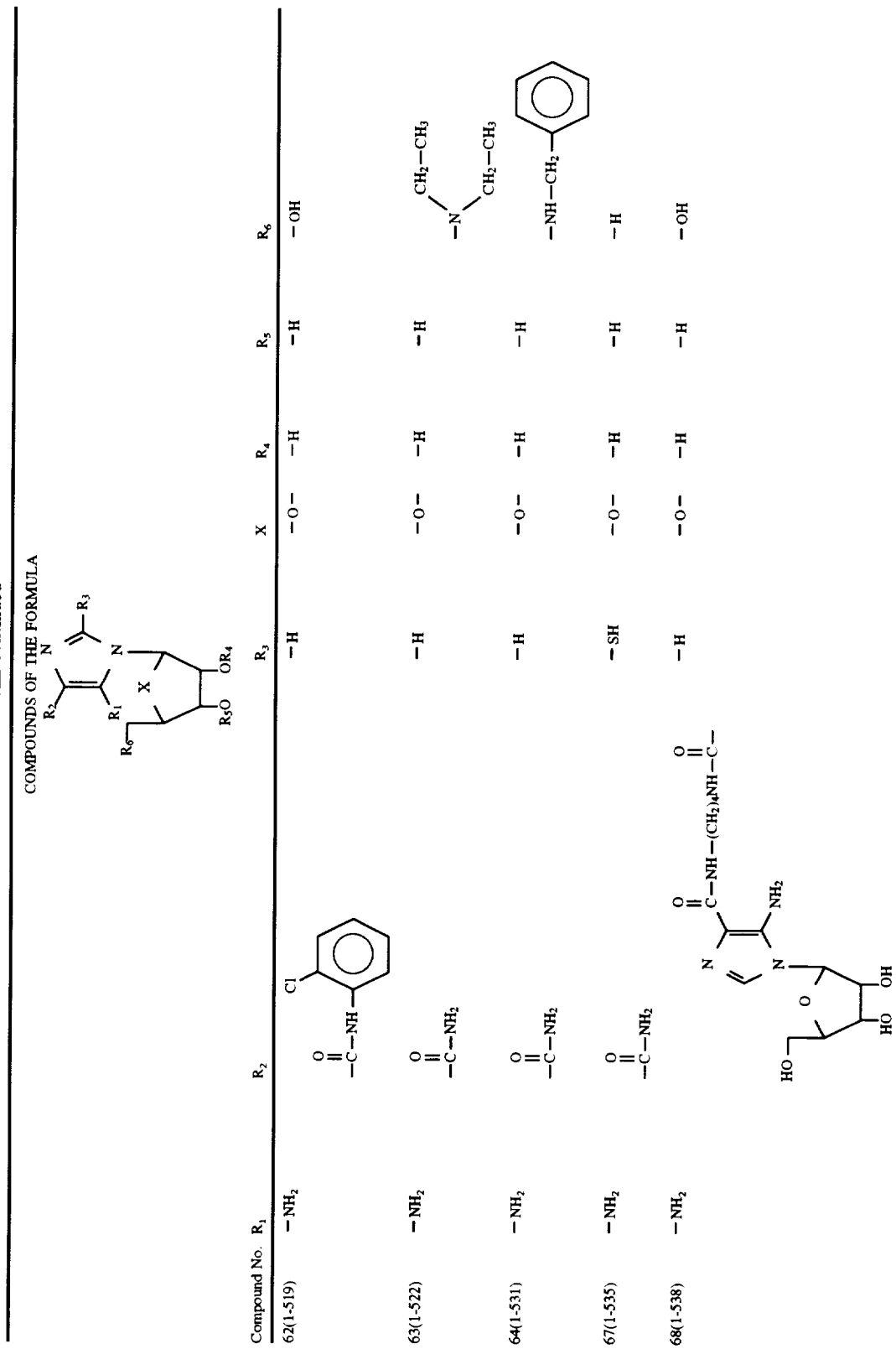
| Compound No. | $R_1$ | $R_2$ | $R_3$ | X | $R_4$ | $R_5$ | $R_6$ |
|---|---|---|---|---|---|---|---|
| 62(1-519) | $-NH_2$ | (2-chlorophenyl)-NH-C(=O)- | $-H$ | $-O-$ | $-H$ | $-H$ | $-OH$ |
| 63(1-522) | $-NH_2$ | $-C(=O)-NH_2$ | $-H$ | $-O-$ | $-H$ | $-H$ | $-N(CH_2-CH_3)(CH_2-CH_3)$ |
| 64(1-531) | $-NH_2$ | $-C(=O)-NH_2$ | $-H$ | $-O-$ | $-H$ | $-H$ | $-NH-CH_2-$phenyl |
| 67(1-535) | $-NH_2$ | $-C(=O)-NH_2$ | $-SH$ | $-O-$ | $-H$ | $-H$ | $-H$ |
| 68(1-538) | $-NH_2$ | [nucleoside amide substituent] | $-H$ | $-O-$ | $-H$ | $-H$ | $-OH$ |

TABLE XII-continued

COMPOUNDS OF THE FORMULA

| Compound No. | $R_1$ | $R_2$ | $R_3$ | X | $R_4$ | $R_5$ | $R_6$ |
|---|---|---|---|---|---|---|---|
| 69(1-549) | $-NH_2$ | (structure) | $-H$ | $-O-$ | $-H$ | $-H$ | $-OH$ |
| 70(1-551) | $-NH_2$ | $O=C-NH_2$ | $-SH$ | $-O-$ | $-H$ | $-H$ | $-NH_2$ |
| 71(1-562) | $-NH_2$ | $O=C-NH-CH_2-$(p-nitrophenyl) | $-H$ | $-O-$ | $-H$ | $-H$ | $-N_3$ |
| 72(1-563) | $-NH_2$ | $O=C-NH-CH_2-$(p-nitrophenyl) | $-H$ | $-O-$ | $-H$ | $-H$ | $-NH_2$ |
| 73(1-566) | $-NH_2$ | $O=C-NH-(CH_2)_3-$(p-nitrophenyl) | $-H$ | $-O-$ | $-H$ | $-H$ | $-OH$ |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 74(1-572) | $-NH_2$ | $-\overset{O}{\underset{\|}{C}}-NH-CH_2-$(4-CF₃-C₆H₄) | $-H$ | $-O-$ | $-H$ | $-H$ | $-OH$ |
| 75(1-577) | $-NH_2$ | $-\overset{O}{\underset{\|}{C}}-NH-CH_2-$(4-S(O)₂-NH₂-C₆H₄) | $-H$ | $-O-$ | $-H$ | $-H$ | $-OH$ |
| 76(1-578) | $-NH_2$ | $-\overset{O}{\underset{\|}{C}}-NH_2$ | $-H$ | $-O-$ | $-H$ | $-H$ | $-NH-CH_2-$(4-Cl-C₆H₄) |
| 77(1-588) | $-NH_2$ | $-H$ | $-H$ | $-O-$ | $-H$ | $-H$ | $-OH$ |
| 78(1-599) | $-NH_2$ | $-\overset{O}{\underset{\|}{C}}-NHCH_2-$(4-Cl-C₆H₄) | $-H$ | $-O-$ | $-\overset{O}{\underset{\|}{C}}-CH_3$ | $-\overset{O}{\underset{\|}{C}}-CH_3$ | $-OH$ |
| 79(1-607) | $-NH_2$ | $-\overset{O}{\underset{\|}{C}}-NH_2$ | $-H$ | $-O-$ | $-H$ | $-H$ | $-OH$ |

TABLE XIII

Physical Characteristics and Preparation

| Compound No. (Table XII) | Physical State | Calculated Elemental Analysis | | | | | Preparation Reference or Source |
|---|---|---|---|---|---|---|---|
| | | % C | % H | % N | % O | | |
| 1(1-110) | White or light pink powder | 41.86 | 5.46 | 21.70 | 30.98 | | Sigma Chemical Co. |
| 2(1-111) | White powder | 46.88 | 5.25 | 14.58 | 33.30 | | Example A |
| 3(1-115) | mp 205.00–206.00° C. | 45.00 | 5.04 | 23.32 | 26.64 | | U.S. Pat. No. 3,450,693; Suzuki et al. |
| 4(1-122) | Foam | 39.56 | 5.53 | 25.63 | 29.28 | | Chem. Pharm. Bull 25:1959 (1977) |
| 5(1-145) | mp 209.00–209.00° C. | 46.87 | 6.29 | 21.86 | 24.97 | | European Patent Appn 0278,501 |
| 6(1-155) | mp 192.00–192.00° C. | 46.15 | 6.34 | 19.57 | 27.94 | | Chem. Pharm. Bull 29(7):1870 (1981) |
| 7(1-164) | White solid, mp 173.5–175° C. | 46.00 | 6.11 | 22.35 | 25.53 | | Example B |
| | | | | | | % P | |
| 8(1-172) | White powder | 30.35 | 4.81 | 15.73 | 40.42 | 8.69 | Sigma Chemical Co. |
| 9(1-177) | White solid | 47.89 | 5.20 | 13.14 | 33.77 | | J. Het. Chem. 9:623 (1972) |
| 10(1-186) | Foam | 51.53 | 6.79 | 17.17 | 24.51 | | Example C |
| 11(1-226) | White solid, mp 178–179° C. | | | | | | Example E |
| 12(1-232) | Off-white solid, mp 206–207° C. | 48.32 | 6.08 | 18.78 | 26.82 | | Example D |
| 13(1-240) | Off-white crystals, mp 158–159° C. | 32.06 | 3.89 | 16.62 | 23.73 | 23.70 | J. Org. Chem. 39:3651 (1974) |
| 14(1-260) | Tan foam | 43.96 | 5.53 | 15.38 | 35.13 | | Example F |
| | | | | | | % S | |
| 15(1-261) | Pink crystals, mp 174.00–174.00° C. | 32.05 | 4.48 | 20.76 | 33.20 | 9.51 | Example G |
| 16(1-273) | Amorphous solid | 44.65 | 6.09 | 17.53 | 29.74 | | Proc. Nat. Acad. Sci. (USA) 85:7174 (1988) |
| 17(1-295) | Light brown foam | 46.69 | 5.88 | 16.33 | 31.10 | | J. Am. Chem. Soc. 112:4891–4897 (1990) |
| 18(1-335) | White solid, mp 148.00–149.00° C. | 41.81 | 5.96 | 24.38 | 27.85 | | Heterocycles 24:2449 (1986) |
| 19(1-154) | mp 207–209° C. | 44.63 | 5.83 | 23.13 | 26.42 | | J. Med. Chem. 18:1237 (1975) |
| 20(1-188) | White crystals, mp 185–186° C. | 44.12 | 5.92 | 20.58 | 29.38 | | Example I |
| 21(1-227) | White crystalline solid, mp 113–115° C. | 42.02 | 5.88 | 27.22 | 24.88 | | Example H |
| 22(1-243) | White crystals, mp 122–125° C. | 44.12 | 5.92 | 20.58 | 29.38 | | Example I |
| 23(1-343) | Yellow foam | 48.86 | 4.87 | 17.80 | 28.47 | | Example J |
| | | | | | | % Cl | |
| 24(1-354) | White foam | 50.20 | 5.00 | 14.64 | 20.90 | 9.26 | Example K |
| 25(1-360) | White foam | 46.06 | 4.35 | 13.43 | 19.17 | 16.99 | Example L |
| 26(1-332) | White foam | 39.07 | 4.74 | 12.81 | 23.13 | 12.81 | Example N |
| | | | | | | % S | |
| 27(1-395) | Yellow crystals, mp 205–208° C. | 33.33 | 4.97 | 17.27 | 24.66 | 19.77 | Example M |
| 28(1-348) | Pale yellow foam | 48.86 | 4.87 | 17.80 | 28.47 | | Example Q |
| | | | | | | % Cl | |
| 29(1-349) | Pale yellow foam | 50.20 | 5.00 | 14.64 | 20.90 | 9.26 | Example R |
| 30(1-388) | Off-white foam | 56.35 | 6.12 | 15.46 | 22.07 | | Example S |
| 31(1-251) | White crystals | 46.15 | 6.34 | 19.57 | 27.94 | | Example O |
| 32(1-262) | Off-white powder | 49.67 | 7.05 | 17.82 | 25.45 | | Example P |
| 33(1-263) | Pink foam | 49.67 | 7.05 | 17.82 | 25.45 | | Example P |
| 34(1-250) | White crystals | 46.15 | 6.34 | 19.57 | 27.94 | | Example O |
| 35(1-355) | White foam | 50.20 | 5.00 | 14.64 | 20.90 | 9.26 | Example T |
| 36(1-207) | White powder | 51.53 | 6.79 | 17.17 | 24.51 | | Example U |
| 37(1-270) | pale yellow powder, mp 135–155° C. | 46.47 | 6.69 | 19.36 | 17.69 | 9.80 | Example AI |
| 38(1-351)+ | off-white powder, mp 92–95° C. | 44.19 | 5.42 | 27.75 | 22.64 | — | |
| 39(1-390) | white crystals, mp 187–188° C. | 53.96 | 5.86 | 14.81 | 25.37 | — | Example V |
| | | | | | | % S | |
| 40 (1-392)+ | mp 126° C. | 39.41 | 5.14 | 20.43 | 23.33 | 11.69 | R. Muramoto, et al. Chem. Pharm. Butt. (Japan) 23:759 (1975). |
| | | | | | | % Cl | |
| 41(1-396-3) | light green solid | 50.53 | 6.12 | 16.37 | 18.70 | 8.29 | Example W |
| 42(1-431) | pink foam | 49.76 | 5.40 | 13.65 | 31.19 | — | Example X |
| | | | | | | % S | |
| 43(1-432) | white powder | 49.17 | 4.95 | 15.29 | 21.83 | 8.75 | Example Y |

TABLE XIII-continued

Physical Characteristics and Preparation

| Compound No. (Table XII) | Physical State | Calculated Elemental Analysis % C | % H | % N | % O | | Preparation Reference or Source |
|---|---|---|---|---|---|---|---|
| 44(1-434) | white foam | 40.52 | 4.04 | 11.81 | 16.87 | % I 26.76 | Example AA |
| 45(1-438) | white foam | 54.54 | 6.86 | 15.90 | 22.70 | — | Example Z |
| 46(1-445) | yellow foam | 38.19 | 3.61 | 13.92 | 19.08 | % I 25.22 | Example AB |
| 47(1-450) | yellow foam | 46.83 | 4.42 | 13.65 | 27.29 | % S 7.81 | Example AC |
| 48(1-452) | tan solid, mp 189–193° C. | 56.66 | 5.59 | 15.55 | 22.20 | — | Example AD |
| 49(1-453) | pale yellow flakes | 50.12 | 5.20 | 17.19 | 27.49 | — | Example AE |
| 50(1-459) | yellow foam | 50.12 | 5.20 | 17.19 | 27.49 | — | Example AF |
| 51(1-466) | yellow crystals, mp 174–176° C. | 46.67 | 4.41 | 17.01 | 23.31 | % Cl 8.61 | Example AG |
| 52(1-467) | pale yellow foam | 47.12 | 4.45 | 24.04 | 15.69 | % Cl 8.69 | Example AH |
| 53(1-468) | off-white powder | 45.94 | 5.06 | 16.74 | 15.30 | % Cl 16.95 | Example AH |
| 54(1-483) | white foam | 41.66 | 5.59 | 19.43 | 22.20 | % S 11.12 | Example AJ |
| 55(1-484) | off-white crystals, mp 214–216° C. | 43.60 | 4.15 | 13.56 | 19.36 | % Br 19.34 | Example AK |
| 56(1-487) | white foam | 44.98 | 4.48 | 13.11 | 18.72 | % Br 18.70 | Example AL |
| 57(1-488) | off-white crystals, | 39.15 | 3.72 | 12.17 | 17.38 | % I 27.57 | Example AM |
| 58(1-489) | yellow powder mp 227–229° C. | 47.50 | 4.52 | 18.46 | 29.52 | — | Example AN |
| 59(1-506) | yellow foam | 50.12 | 5.20 | 17.19 | 27.49 | — | Example AO |
| 60(1-508) | yellow/orange solid, mp 199–200° C. | 50.89 | 5.39 | 18.74 | 24.97 | — | Example AP |
| 61(1-509) | pink foam | 52.39 | 5.22 | 15.27 | 17.45 | % Cl 9.67 | Example AQ |
| 62(1-510) | pale yellow foam | 39.47 | 5.30 | 18.41 | 26.29 | % S 10.54 | Example AR |
| 63(1-517) | off-white foam | 44.28 | 6.32 | 25.82 | 23.59 | — | Example AS |
| 64(1-519) | brown crystals, mp 131–135° C. | 48.86 | 4.65 | 15.19 | 21.69 | % Cl 9.61 | Example AT |
| 65(1-522) | brown foam | 49.83 | 7.40 | 22.35 | 20.42 | — | Example BF |
| 66(1-531) | off-white foam | 55.32 | 6.09 | 20.16 | 18.42 | — | Example AU |
| 67(1-535) | yellow crystals, mp 201–203° C. | 39.41 | 5.14 | 20.43 | 23.33 | % S 11.69 | Example AV |
| 68(1-538) | pale reddish powder, mp 181–185° C. | 48.16 | 6.40 | 18.72 | 26.73 | — | Example AW |
| 69(1-549) | white powder | 48.32 | 6.08 | 18.78 | 26.82 | — | Example AX |
| 70(1-551) | pale orange powder | 37.36 | 5.23 | 24.21 | 22.12 | % S 11.08 | Example AY |
| 71(1-562) | yellow foam | 45.93 | 4.34 | 26.78 | 22.95 | — | Example AZ |
| 72(1-563) | yellow foam | 48.98 | 5.14 | 21.42 | 24.47 | — | Example BA |
| 73(1-566) | yellow foam | 51.30 | 5.50 | 16.62 | 26.58 | — | Example BG |
| 74(1-572) | off-white powder, mp 137–140° C. | 49.09 | 4.60 | 13.46 | 19.21 | % F 13.69 | Example BB |
| 75(1-577) | off-white foam | 44.96 | 4.95 | 16.38 | 26.20 | % S 7.50 | Example BC |
| 76(1-578) | tan foam | 50.33 | 5.28 | 18.34 | 16.76 | % Cl 9.29 | Example BD |
| 77(1-588) | brown foam | 48.23 | 6.58 | 21.09 | 24.09 | — | Example BE |
| 78(1-599) | white foam | 51.56 | 5.19 | 15.03 | 20.60 | % Cl 7.61 | Example BH |
| 79(1-607) | white foam | 39.41 | 5.14 | 20.43 | 23.33 | % S 11.69 | |

We claim:

1. A compound of the formula:

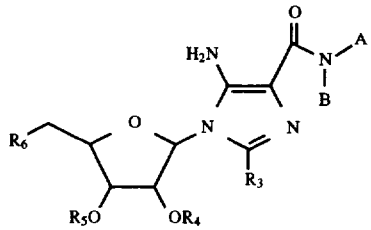

wherein

A is selected from the group consisting of hydrogen, aryl, alkyl, aralkyl, a cycloalkyl or bicycloalkyl ring of from 3 to 8 carbons, and the group

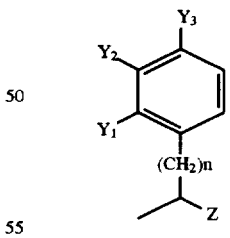

wherein n is 0 to 3 and $Y_1$, $Y_2$ and $Y_3$ are each independently selected from hydrogen, halogen, lower alkyl, hydroxy, lower alkoxy, methoxy, lower perhaloalkyl, dialkylamino, lower dialkylaminoalkyl, nitro, sulfonamide, and trifluoromethyl, and Z is selected from hydrogen and lower alkyl;

B is hydrogen or lower alkyl;

$R_3$ is selected from hydrogen, halogen, and S—W, where W is hydrogen, alkyl, phenyl or substituted phenyl;

$R_4$ and $R_5$ are each selected from hydrogen, acyl and lower alkyl or together form a cyclic carbonate; and $R_6$ is selected from, hydroxy, phosphate ester, $-OSO_2NH_2$, sulfhydryl, halogen, $-OCOV$, $-SV$, $-SOV$, $N_3$ and $NVV'$, where V and V' are independently selected from hydrogen, aryl, lower alkyl, $-CH_2-\phi$ and substituted $-CH_2-\phi$, and pharmaceutically acceptable salts thereof, provided that when A is hydrogen, para-iodophenyl, or $-CH_2-\phi$, B is hydrogen, $R_3$ is hydrogen, halogen, or sulfhydryl, and $R_4$ and $R_5$ are hydrogen acyl, or together form a cyclic carbonate, then $R_6$ is not OH, halogen, phosphate ester, or $-O$-acyl.

2. A compound of the formula:

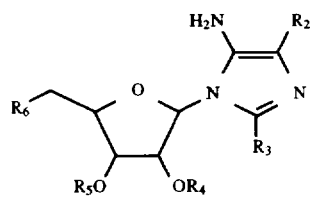

wherein $R_2$ is selected from the group consisting of hydrogen, $-CN$ and the group

where

T is selected from oxygen, sulfur, NOH, NH, and $NO(CH_2)_nCH_3$ where n is from 0 to 2) and U is selected from lower alkoxy, amino, a 3 to 6 member heterocyclic ring optionally fused to a 3 to 6 member aryl ring, and the group

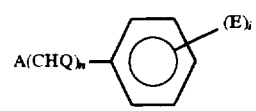

wherein

A is one of NH and S, n is from 0 to 3, i is from 0 to 2, Q is one of hydrogen and hydroxy, and E represents a nitro or hydroxy group, provided that where U is amino, T is not one of sulfur, NOH, NH, and $NOCH_3$; where T is amino, U is not lower alkoxy; and where A is amino and n is 1, Q is not hydroxy;

$R_3$ is selected from hydrogen, halogen, and $S-W$, where W is phenyl, or substituted phenyl, or hydrogen when T is not oxygen and U is not amino;

$R_4$ and $R_5$ are each independently selected from hydrogen, $-COCH_3$ and lower alkyl, or together form a cyclic carbonate; and $R_6$ is selected from, hydroxy, phosphate ester, $-OSO_2NH_2$, sulfhydryl, halogen, $-OCOCH_3$, $-SCH_3$, $-SOCH_3$, $NH_2$ and $N_3$;

and pharmaceutically acceptable salts thereof;

provided that when $R_2$ is $CONH_2$, $CONH$-para-iodophenyl, hydrogen, CN, or $CONHCH_2-\phi$ and $R_3$ is hydrogen or halogen, and $R_4$ and $R_5$ are hydrogen, acyl, or together form a cyclic carbonate, then $R_6$ is not halogen, phosphate ester, OH, or $-O$-acyl.

3. A compound of the formula:

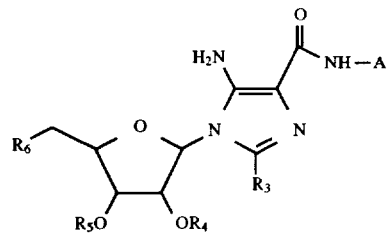

wherein

A is selected from the group consisting of hydrogen, lower alkyl, a ring of from 3 to 6 carbons, and the group

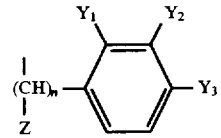

wherein $Y_1$, $Y_2$ and $Y_3$ are each independently selected from hydrogen, halogen, lower alkyl, alkoxy, nitro, dialkylamino, sulfonamide, trifluoromethyl, Z is selected from hydrogen and lower alkyl, and n is 0 or 1;

$R_4$ and $R_5$ are each independently selected from hydrogen, $-COCH_3$ and lower alkyl or together form a cyclic carbonate; and $R_6$ is selected from $-OH$ and $-NH_2$, and pharmaceutically acceptable salts thereof;

provided that when A is hydrogen, para-iodophenyl or $-CH_2-\phi$ and $R_6$ is OH, then $R_4$ and $R_5$ are not hydrogen or $COCH_3$ and do not together form a cyclic carbonate.

4. A compound of the formula:

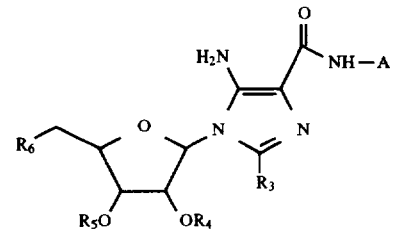

wherein

A is selected from the group consisting of hydrogen, lower alkyl, a ring of from 3 to 6 carbons, and the group

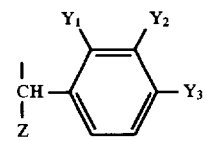

wherein $Y_1$, $Y_2$ and $Y_3$ are each independently selected from hydrogen, halogen, lower alkyl, alkoxy, nitro sulfonamide, trifluoromethyl, and dialkylaminoalkyl and Z is selected from hydrogen and lower alkyl;

$R_3$ is selected from halogen, sulfhydryl and $-S-W$ wherein W is alkyl, phenyl or substituted phenyl;

81

R₄ and R₅ are hydrogen; and

R₆ is hydroxy;

and pharmaceutically acceptable salts thereof.

5. A compound of the formula:

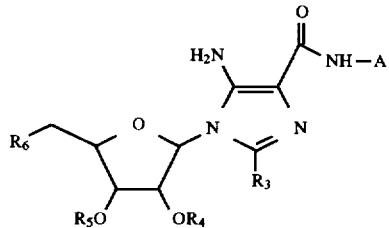

wherein

A is selected from the group consisting of lower alkyl, a ring of from 3 to 6 carbons, and the group

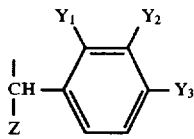

wherein

Y₁, Y₂ and Y₃ are each independently selected from hydrogen, halogen, lower alkyl, alkoxy, nitro, sulfonamide, trifluoromethyl, and dialkylaminoalkyl, and Z is selected from hydrogen and lower alkyl;

R₃ is hydrogen;

R₄ and R₅ are hydrogen or together form a cyclic carbonate; and

R₆ is amino;

and pharmaceutically acceptable salts thereof.

6. A compound of the formula:

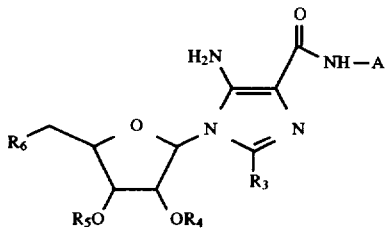

wherein

A is selected from the group consisting of hydrogen, lower alkyl, a ring of from 3 to 6 carbons, and the group

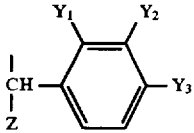

wherein

Y₁, Y₂ and Y₃ are each independently selected from hydrogen, halogen, lower alkyl, alkoxy, nitro, sulfonamide, trifluoromethyl, and dialkylaminoalkyl, and Z is selected from hydrogen and lower alkyl;

R₃ is hydrogen;

R₄ is hydrogen or lower alkyl;

R₅ is hydrogen or lower alkyl; and

82

R₆ is hydroxy;

and pharmaceutically acceptable salts thereof, provided that when A is hydrogen, R₁ and R₅ are not both hydrogen.

7. A compound of claim 1, selected from the group consisting of 5-amino-1-β-D-ribofuranosylimidazole-4-N-(cyclopentyl) carboxamide, 5-amino-1-β-D-ribofuranosylimidazole-4-N-(cyclopropyl) carboxamide, 5-amino-5'-sulfamoyl-1-β-D-ribofuranosylimidazole-4-carboxamide, 5-amino-1-(2-O-methyl-β-D-ribofuranosyl)imidazole-4-carboxamide, 5-amino-1-(3-O-methyl-β-D-ribofuranosyl)imidazole-4-carboxamide, 5-amino-1-β-D-ribofuranosylimidazole-4-N-|(4-nitrophenyl)methyl|carboxamide, 5-amino-1-β-D-ribofuranosylimidazole-4-N-|(5-chlorophenyl)methyl|carboxamide, 5-amino-1-β-D-ribofuranosylimidazole-4-N-|(2,4-dichlorophenyl)methyl|carboxamide, 5-amino-1-(5-chloro-5-deoxy-β-D-ribofuranosyl) imidazole-4-carboxamide, 5-amino-1-β-D-ribofuranosylimidazole-4-N-|(3-nitrophenyl)methyl|carboxamide, 5-amino-1-β-D-ribofuranosylimidazole-4-N-|(4-chlorophenyl)methyl|carboxamide, 5-amino-1-β-D-ribofuranosylimidazole-4-N-|(4-methylphenyl)methyl|carboxamide, 5-amino-1-(3-O-ethyl-β-D-ribofuranosyl-4-imidazole-carboxamide, 5-amino-1-(2-O-n-butyl-β-D-ribofuranosylimidazole-4-carboxamide, 5-amino-1-(3-O-n-butyl-β-D-ribofuranosylimidazole-4-carboxamide, 5-amino-1-(3-O-ethyl-β-D-ribofuranosyl-4-imidazole-carboxamide, 5-amino-1-β-D-ribofuranosylimidazole-4-N-|(3-chlorophenyl)methyl|carboxamide, 5-amino-1-(5-amino-5-deoxy-1-β-D-ribofuranosyl) imidazole-4-(N-cyclopentyl) carboxamide, 5-amino-1-β-D-ribofuranosylimidazole-4-N-|4-methoxybenzyl|carboxamide, 5-amino-1-β-D-ribofuranosylimidazole-4-N-(4-dimethylaminobenzyl)carboxamide, 5-amino-2-thiophenyl-1-β-D-ribofuranosylimidazole-4-carboxamide, 5-amino-1-β-D-ribofuranosylimidazole-4-N-|(3-iodophenyl)methyl|carboxamide, 5-amino-1-β-D-ribofuranosylimidazole-4-N-(2-endo-norbornyl)carboxamide, 5-amino-1-(5-iodo-5-deoxy-β-D-ribofuranosyl)imidazole-4-N-|(4-nitrophenyl)methyl|carboxamide, 5-amino-1-β-D-ribofuranosylimidazole-4-N-|(1-(4-nitrophenyl)ethyl|carboxamide, 5-amino-1-β-D-ribofuranosylimidazole-4-N-|1-(4-nitrophenyl)ethyl|carboxamide, 5-amino-1-(5-chloro-5-deoxy-β-D-ribofuranosyl) imidazole-4-N-|(4-nitrophenyl)methyl|carboxamide, 5-amino-1-(5-amino-5-deoxy-β-D-ribofuranosyl) imidazole-4-N-|(4-chlorophenyl)methyl|carboxamide, 5-amino-1-(5-deoxy-5-methylthio-β-D-ribofuranosyl) imidazole-4-carboxamide, 5-amino-1-β-D-ribofuranosylimidazole-4-N-(4-bromophenyl)carboxamide, 5-amino-1-β-D-ribofuranosylimidazole-4-N-|(4-bromophenyl)methyl|carboxamide, 5-amino-1-β-D-ribofuranosylimidazole-4-N-(4-nitrophenyl)carboxamide, 5-amino-1-(5-deoxy-β-D-ribofuranosyl)imidazole-4-N-|(4-chlorophenyl)methyl|carboxamide,
5-amino-1-(5-deoxy-5-methylsulfinyl-β-D-ribofuranosyl) imidazole-4-carboxamide,
5-amino-1-β-D-(5-deoxy-5-methylamino-1-β-D-ribofuranosyl)imidazole-4-carboxamide,
5-amino-1-β-D-ribofuranosylimidazole-4-N-(2-chlorophenyl)carboxamide,
5-amino-1-(5-deoxy-5-diethylaminoribo-β-D-furanosyl) imidazole-4-carboxamide,
5-amino-1-β-D-(5-benzylamino-5-deoxy-1-β-D-ribofuranosyl)imidazole-4-carboxamide,
5-amino-2-thio-1-β-D-(5-deoxy-1-β-D-ribofuranosyl) imidazole-4-carboxamide,
5-amino-2-thio-1-(5-amino-5-deoxy-β-D-ribofuranosyl) imidazole-4-carboxamide,
5-amino-1-(5-amino-5-deoxy-β-D-ribofuranosyl) imidazole-4-N-|4-nitrophenyl)methyl|carboxamide,
5-amino-1-β-D-ribofuranosylimidazole-4-N-|3-(4-nitrophenyl)propyl|carboxamide,
5-amino-1-β-D-ribofuranosyl)imidazole-4-N-|(4-trifluoromethylphenyl)methyl|carboxamide,
5-amino-1-β-D-ribofuranosyl)imidazole-4-N-|(4-sulfamoylphenyl)methyl|carboxamide,
5-amino-1-(5-(4-chlorobenzyl-amino-5-deoxy-β-D-ribofuranosyl)imidazole-4-carboxamide,
5-amino-(5-amino-5-deoxy-2,3-di-O-acetyl-β-D-ribofuranosyl)imidazole-4-N-|(4-chlorophenyl)methyl| carboxamide, and
5-amino-1-(5-deoxy-5-sulfhydryl-1-β-D-ribofuranosyl) imidazole-4-carboxamide.

8. A compound of claim 2, selected from the group consisting of:
5-amino-4-(1-piperidiniocarbamoyl)-1-β-D-ribofuranosylimidazole,
5-amino-1-β-D-ribofuranosylimidazole-4-N-|2-hydroxy-2-(3,4-dihydroxyphenyl)ethyl|carboxamide,
5-amino-1-β-D-ribofuranosylimidazole-4-carboxylic acid, p-nitrobenzylthio ester,
5-amino-1-β-D-ribofuranosylimidazole-4-N-|(1-(4-nitrophenyl)ethyl|carboxamide,
5-amino-1-β-D-ribofuranosylimidazole-4-N-|(1-(4-nitrophenyl)ethyl|carboxamide,
5-amino-1-β-D-ribofuranosylimidazole-4-N-|(1-(3-nitrophenyl)methyl|carboxamide,
5-amino-1-β-D-ribofuranosylimidazole-4-N-|2-(4-nitrophenyl)ethyl|carboxamide, and
5-amino-4-|1-(4-nitrophenyl)|piperazino-4-carbamoyl|-1-β-D-ribofuranosylimidazole.

9. A compound of claim 3, selected from the group consisting of:
5-amino-1-β-D-ribofuranosylimidazole-4-N-(cyclopentyl) carboxamide,
5-amino-1-β-D-ribofuranosylimidazole-4-N-(cyclopropyl) carboxamide,
5-amino-1-(2-O-methyl-β-D-ribofuranosyl)imidazole-4-carboxamide,
5-amino-1-(3-O-methyl-β-D-ribofuranosyl)imidazole-4-carboxamide,
5-amino-1-β-D-ribofuranosylimidazole-4-N-|4-nitrophenyl)methyl|carboxamide,
5-amino-1-β-D-ribofuranosylimidazole-4-N-|(3-chlorophenyl)methyl|carboxamide,
5-amino-1-β-D-ribofuranosylimidazole-4-N-|(2,4-dichlorophenyl)methyl|carboxamide,
5-amino-1-β-D-ribofuranosylimidazole-4-N-|(3-nitrophenyl)methyl|carboxamide,
5-amino-1-β-D-ribofuranosylimidazole-4-N-|(4-chlorophenyl)methyl|carboxamide,
5-amino-1-β-D-ribofuranosylimidazole-4-N-|(4-methylphenyl)methyl|carboxamide,
5-amino-1-(3-O-ethyl-β-D-ribofuranosyl)imidazole-4-carboxamide,
5-amino-1-(2-O-n-butyl-β-D-ribofuranosyl)imidazole-4-carboxamide,
5-amino-1-(3-O-n-butyl-β-D-ribofuranosyl)imidazole-4-carboxamide,
5-amino-1-(3-O-ethyl-β-D-ribofuranosyl)imidazole-4-carboxamide,
5-amino-1-β-D-ribofuranosylimidazole-4-N-|(3-chlorophenyl)methyl|carboxamide,
5-amino-1-(5-amino-5-deoxy-1-β-D-ribofuranosyl) imidazole-4-(N-cyclopentyl) carboxamide,
5-amino-1-β-D-ribofuranosylimidazole-4-N-|4-methoxybenzyl|carboxamide,
5-amino-1-β-D-ribofuranosylimidazole-4-N-(4-dimethylaminobenzyl)carboxamide,
5-amino-1-β-D-ribofuranosylimidazole-4-N-|(3-iodophenyl)methyl|carboxamide,
5-amino-1-β-D-ribofuranosylimidazole-4-N-(2-endo-norbornyl)carboxamide,
5-amino-1-β-D-ribofuranosylimidazole-4-N-|-1-4-nitrophenyl)ethyl|carboxamide,
5-amino-1-β-D-ribofuranosylimidazole-4-N-|2-(4-nitrophenyl)ethyl|carboxamide,
5-amino-1-(5-amino-5-deoxy-β-D-ribofuranosyl) imidazole-4-N-|(4-chlorophenyl)methyl|carboxamide,
5-amino-1-β-D-ribofuranosylimidazole-4-N-(4-bromophenyl)carboxamide,
5-amino-1-β-D-ribofuranosylimidazole-4-N-|(4-bromophenyl)methyl|carboxamide,
5-amino-1-β-D-ribofuranosylimidazole-4-N-(4-nitrophenyl)carboxamide,
5-amino-1-β-D-ribofuranosyl)imidazole-4-N-(2-chlorophenyl)carboxamide,
5-amino-1-(5-amino-5-deoxy-β-D-ribofuranosyl) imidazole-4-N-|4-nitrophenyl)methyl|carboxamide,
5-amino-1-β-D-ribofuranosylimidazole-4-N-|4-(trifluoromethylphenyl)methyl|carboxamide,
5-amino-1-β-D-ribofuranosylimidazole-4-N-|(4-sulfamoylphenyl)methyl|carboxamide, and
5-amino-(5-amino-5-deoxy-2,3-di-O-acetyl-β-D-ribofuranosyl)imidazole-4-N-|(4-chlorophenyl)methyl| carboxamide.

10. A compound of claim 5, selected from the group consisting of:
5-amino-1-(5-amino-5-deoxy-1-β-D-ribofuranosyl) imidazole-4-(N-cyclopentyl) carboxamide,
5-amino-1-(5-amino-5-deoxy-β-D-ribofuranosyl) imidazole-4-N-|(4-chlorophenyl)methyl|carboxamide, and
5-amino-1-(5-amino-5-deoxy-β-D-ribofuranosyl) imidazole-4-N-|(4-nitrophenyl)methyl|carboxamide.

11. A compound of claim 10, selected from the group consisting of:
5-amino-1-(2-O-methyl-β-D-ribofuranosyl)imidazole-4-carboxamide,
5-amino-1-(2-O-n-butyl-β-D-ribofuranosyl)imidazole-4-carboxamide, and
5-amino-1-(3-O-ethyl-β-D-ribofuranosyl)imidazole-4-carboxamide.

12. A compound of claim 11, where $R_4$ and $R_5$ are both acyl or together form a cyclic carbonate.

13. A compound of claim 12, where $R_4$ and $R_5$ are independently $COR_7$, where each $R_7$ has from 1 to 10 carbons and is one of aryl, aralkyl, and alkyl.

14. A compound of claim 12, where A, B, and $R_3$ are hydrogen, $R_6$ is benzylamino, and $R_4$ and $R_5$ together form a cyclic carbonate.

15. A compound of claim 12, where A, B, and $R_3$ are hydrogen, $R_6$ is benzylamino, and $R_4$ and $R_5$ are independently $COR_7$, where each $R_7$ has from 1 to 10 carbons and is one of aryl, aralkyl, and alkyl.

16. A compound according to claim 15, wherein $R_4$ and $R_5$ are both $(CH_3)_3CCO-$.

* * * * *

UNITED STATES PATENT AND TRADEMARK OFFICE
CERTIFICATE OF CORRECTION

PATENT NO. : 5,777,100
DATED : Jul. 7, 1998
INVENTOR(S) : David A. Bullough, Harry E. Gruber, Ernest K. Metzker, Kevin M. Mullane, Bheemarao G. Ugarkar, Clinton E. Browne It is certified that error appears in the above-indentified patent and that said Letters Patent is hereby corrected as shown below:

Title page, column 1, in section "[75] Inventors:", after "Escondido" and before ";" please insert --, all of Calif.--

Title page, column 1, in section "[75] Inventors:", after "Clinton E. Browne," please delete "Vista, all of Calif." and add --Gainesville, Florida--

Title page, Item [63], and column 1, line 5, before "Continuation of", please add --Continuation-in-part of Ser. No. 08/286,383, Aug. 4, 1994, abandoned, which is a--

Signed and Sealed this

Thirtieth Day of March, 1999

Attest:

Q. TODD DICKINSON

*Attesting Officer*  *Acting Commissioner of Patents and Trademarks*